(12) United States Patent
Li

(10) Patent No.: US 10,316,087 B2
(45) Date of Patent: Jun. 11, 2019

(54) SOLUBLE AND STABLE HETERODIMERIC TCR

(71) Applicant: GUANGDONG XIANGXUE LIFE SCIENCES, LTD., Guangzhou (CN)

(72) Inventor: Yi Li, Guangzhou (CN)

(73) Assignee: GUANGDONG XIANGXUE LIFE SCIENCES, LTD., Guangzhou (CN)

( * ) Notice: Subject to any disclaimer, the term of this patent is extended or adjusted under 35 U.S.C. 154(b) by 0 days.

(21) Appl. No.: 15/573,692

(22) PCT Filed: Mar. 29, 2016

(86) PCT No.: PCT/CN2016/077680
§ 371 (c)(1),
(2) Date: Nov. 13, 2017

(87) PCT Pub. No.: WO2016/184258
PCT Pub. Date: Nov. 24, 2016

(65) Prior Publication Data
US 2018/0201682 A1     Jul. 19, 2018

(30) Foreign Application Priority Data
May 20, 2015   (CN) .......................... 2015 1 0260322

(51) Int. Cl.
| C07K 14/725 | (2006.01) |
| A61K 38/17 | (2006.01) |
| C07K 16/28 | (2006.01) |
| C12P 21/02 | (2006.01) |
| G01N 33/68 | (2006.01) |

(52) U.S. Cl.
CPC ........ *C07K 16/2809* (2013.01); *A61K 38/177* (2013.01); *C07K 14/7051* (2013.01); *C12P 21/02* (2013.01); *G01N 33/68* (2013.01)

(58) Field of Classification Search
None
See application file for complete search history.

(56) References Cited

U.S. PATENT DOCUMENTS

2014/0112925 A1*  4/2014  Voss .................. C07K 16/00
                                                    424/135.1

FOREIGN PATENT DOCUMENTS

| CN | 100528897 C | 8/2009 |
| WO | 2000/06733 A2 | 2/2000 |
| WO | WO2006/037960 | * 4/2006 |

OTHER PUBLICATIONS

International Search Report in PCT/CN2016/077680, dated Jul. 5, 2016, 4 pages.
Tai et al., "Application of T Cell Receptor Gene Modification in Adoptive Immunotherapy," Drug Evaluation Research, vol. 34, No. 2, Apr. 30, 2011, 5 pages.
Thomas et al., "Targeting the Wilms Tumor Antigen 1 by TCR Gene Transfer: TCR Variants Improve Tetramer Binding but Not the Function of Gene Modified Human T Cells," The Journal of immunology, 2007, 179: 5803-5810.

* cited by examiner

Primary Examiner — Rebecca E Prouty
(74) Attorney, Agent, or Firm — Kilpatrick Townsend & Stockton LLP

(57) ABSTRACT

Disclosed are a heterodimeric TCR containing artificial interchain disulfide bond between the variable region of α chain and the constant region of β chain, a preparing method therefor and a use thereof.

17 Claims, 26 Drawing Sheets
Specification includes a Sequence Listing.

AQEVTQIPAALSVPEGENLVLNCSFTDSAIYNLQWFRQD<u>C</u>GKGLTSLLLIQSSQ
REQTSGRLNASLDKSSGRSTLYIAASQPGDSATYLCAVRPTSGGSYIPTFGRGTSLIV
HPY (SEQ ID NO: 1)

Fig. 1a

GVTQTPKFQVLKTGQSMTLQCAQDMNHEYMSWYRQDPGMGLRLIHYSVGA
GITDQGEVPNGYNVSRSTTEDFPLRLLSAAPSQTSVYFCASSYVGNTGELFFGEGSR
LTVLEDLKNVFPPEVAVFEPSEAEISHTQKATLVCLATGFYPDHVELSWWVNGKEV
HSGVSTD<u>C</u>QPLKEQPALNDSRYALSSRLRVSATFWQNPRNHFRCQVQFYGLSENDE
WTQDRAKPVTQIVSAEAWGRAD (SEQ ID NO: 2)

Fig. 1b

GCACAAGAAGTTACTCAAATTCCGGCGGCGCTGAGCGTTCCGGAAGGTGA
AAACCTGGTGCTGAACTGCAGCTTTACCGATAGCGCGATCTATAACCTGCAGTG
GTTTCGTCAAGATTGCGGTAAAGGTCTGACCAGCCTGCTGCTGATTCAGAGCAG
CCAGCGTGAACAGACCAGCGGTCGTCTGAATGCGAGCCTGGATAAAAGCAGCG
GTCGTAGCACCCTGTATATTGCGGCGAGCCAGCCGGGTGATAGCGCAACCTATC
TGTGTGCGGTTCGTCCGACCAGCGGTGGTAGCTATATTCCGACCTTTGGTCGTGG
CACCAGCCTGATTGTGCATCCGTATTAA (SEQ ID NO: 3)

Fig. 2a

GGCGTCACACAAACCCCGAAATTTCAGGTGCTGAAAACGGGTCAGAGCAT
GACCCTGCAGTGTGCGCAGGATATGAACCACGAATACATGAGCTGGTATCGTCA
AGATCCGGGTATGGGTCTGCGTCTGATCCATTATAGCGTGGGTGCGGGCATTAC
CGATCAGGGTGAAGTGCCGAACGGTTATAATGTTAGCCGTAGCACCACCGAAG
ATTTTCCGCTGCGTCTGCTGAGCGCGGCGCCGAGCCAGACCAGCGTTTATTTTTG
CGCGAGCAGCTATGTTGGTAACACCGGCGAACTGTTTTTTGGTGAAGGCAGCCG
TCTGACCGTTCTGGAAGATCTGAAAAACGTGTTCCGCCGGAAGTTGCGGTTTTT
GAACCGAGCGAAGCGGAAATTAGCCATACCCAGAAAGCGACCCTGGTTTGTCT
GGCGACCGGTTTTTATCCGGATCATGTGGAACTGTCTTGGTGGGTGAACGGCAA
AGAAGTGCATAGCGGTGTTTCTACCGATTGCCAGCCGCTGAAAGAACAGCCGGC
GCTGAATGATAGCCGTTATGCGCTGTCTAGCCGTCTGCGTGTTAGCGCGACCTTT
TGGCAAAATCCGCGTAACCATTTTCGTTGCCAGGTGCAGTTTTATGGCCTGAGC
GAAAACGATGAATGGACCCAGGATCGTGCGAAGCCGGTTACCCAGATTGTTAG
CGCGGAAGCCTGGGGCCGCGCAGATTAA (SEQ ID NO: 4)

Fig. 2b

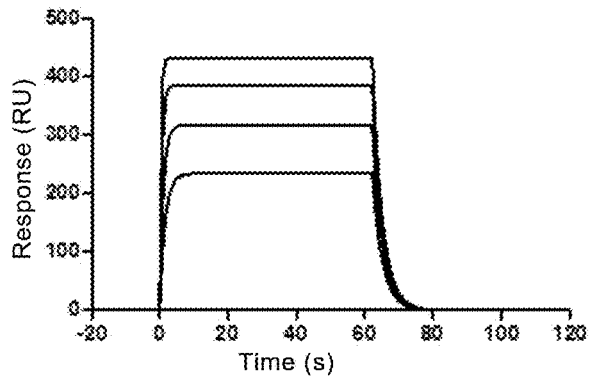

Fig. 6

GQLLEQSPQFLSIQEGENLTVYCNSSSVFSSLQWYRQE<u>C</u>GEGPVLLVTV
VTGGEVKKLKRLTFQFGDARKDSSLHITAAQPGDTGLYLCAGAGSQGNLIFG
KGTKLSVKPN (SEQ ID NO: 5)

Fig. 7a

VDGGITQSPKYLFRKEGQNVTLSCEQNLNHDAMYWYRQDPGQGLRLIY
YSQIVNDFQKGDIAEGYSVSREKKESFPLTVTSAQKNPTAFYLCASSSRSSYE
QYFGPGTRLTVTEDLKNVFPPEVAVFEPSEAEISHTQKATLVCLATGFYPDHV
ELSWWVNGKEVHSGVSTD<u>C</u>QPLKEQPALNDSRYALSSRLRVSATFWQNPRN
HFRCQVQFYGLSENDEWTQDRAKPVTQIVSAEAWGRAD (SEQ ID NO: 6)

Fig. 7b

GGCCAACTGCTGGAACAATCCCCGCAATTCCTGAGTATTCAAGAAGG
CGAAAATCTGACGGTCTACTGTAATTCATCATCGGTCTTTAGCTCTCTGCA
GTGGTATCGTCAAGAATGCGGTGAAGGTCCGGTCCTGCTGGTGACCGTGG
TTACGGGCGGTGAAGTGAAAAAGCTGAAACGTCTGACCTTTCAGTTCGGC
GATGCGCGCAAGGACAGTTCCCTGCATATTACCGCAGCACAGCCGGGTGA
TACGGGTCTGTACCTGTGCGCAGGCGCTGGTAGCCAAGGTAACCTGATTT
TTGGCAAGGGTACGAAGCTGAGCGTTAAACCGAAC (SEQ ID NO: 7)

Fig. 8a

GTGGACGGCGGCATTACCCAAAGCCCGAAGTACCTGTTTCGCAAGG
AAGGCCAAAATGTGACCCTGTCGTGTGAACAAAATCTGAACCATGATGCG
ATGTATTGGTACCGTCAGGACCCGGGTCAAGGTCTGCGTCTGATTTATTA
CAGCCAGATCGTGAATGATTTTCAAAAAGGCGACATTGCAGAAGGTTATA
GCGTGAGCCGTGAAAGAAAGAATCTTTTCCGCTGACCGTCACGTCCGCT
CAGAAGAACCCGACCGCGTTCTACCTGTGCGCGAGCAGCAGCCGTAGCA
GCTATGAACAATACTTTGGTCCGGGTACGCGTCTGACCGTCACGGAAGAT
CTGAAAAACGTGTTTCCGCCGGAAGTTGCGGTTTTTGAACCGAGCGAAGC
GGAAATTAGCCATACCCAGAAAGCGACCTGGTTTGTCTGGCGACCGGTT
TTTATCCGGATCATGTGGAACTGTCTTGGTGGGTGAACGGCAAAGAAGTG
CATAGCGGTGTTTCTACCGATTGCCAGCCGCTGAAAGAACAGCCGGCGCT
GAATGATAGCCGTTATGCGCTGTCTAGCCGTCTGCGTGTTAGCGCGACCT
TTTGGCAAAATCCGCGTAACCATTTTCGTTGCCAGGTGCAGTTTTATGGCC
TGAGCGAAAACGATGAATGGACCCAGGATCGTGCGAAGCCGGTTACCCA
GATTGTTAGCGCGGAAGCCTGGGGCCGCGCAGAT (SEQ ID NO: 8)

Fig. 8b

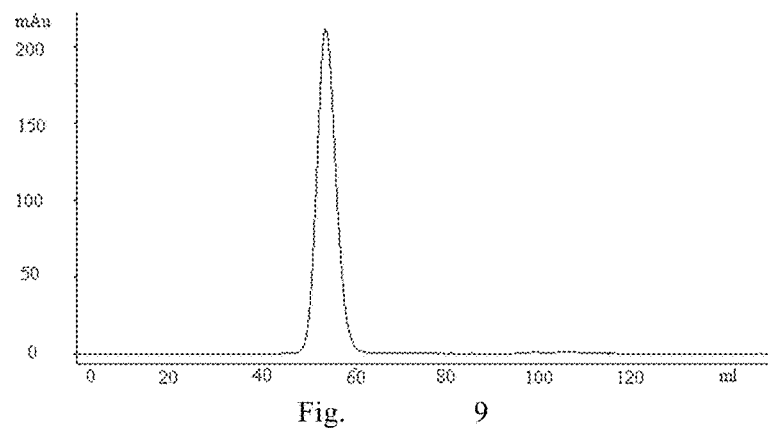

Fig. 9

GKTTQPNSMESNEEEPVHLPCNHSTISGTDYIHWYRQLCSQGPEYVIHGLTSN
VNNRMASLAIAEDRKSSTLILHRATLRDAAVYYCILPLAGGTSYGKLTFGQGTILTV
HPN (SEQ ID NO: 9)

Fig. 13a

GVSQSPRYKVAKRGQDVALRCDPISGHVSLFWYQQALGQGPEFLTYFQNEAQ
LDKSGLPSDRFFAERPEGSVSTLKIQRTQQEDSAVYLCASSLGQAYEQYFGPGTRLT
VTEDLKNVFPPEVAVFEPSEAEISHTQKATLVCLATGFYPDHVELSWWVNGKEVHS
GVSTDCQPLKEQPALNDSRYALSSRLRVSATFWQNPRNHFRCQVQFYGLSENDEW
TQDRAKPVTQIVSAEAWGRAD (SEQ ID NO: 10)

Fig. 13b

GGCAAAACCACCCAGCCGAACTCAATGGAAAGCAACGAAGAAGAACCGG
TCCACCTGCCGTGTAATCACAGCACCATCTCAGGCACCGATTATATTCATTGGTA
CCGTCAGCTGTGCAGCCAAGGTCCGGAATATGTGATCCACGGTCTGACCAGTAA
CGTTAACAATCGTATGGCATCCCTGGCAATTGCTGAAGATCGCAAAAGCTCTAC
CCTGATCCTGCATCGTGCAACGCTGCGTGACGCAGCCGTTTATTACTGCATTCTG
CCGCTGGCCGGCGGTACCAGCTACGGCAAGCTGACGTTTGGCCAGGGTACCATT
CTGACGGTCCACCCGAAC (SEQ ID NO: 11)

Fig. 14a

GGCGTGTCCCAAAGCCCGCGTTACAAAGTTGCCAAGCGTGGTCAAGATGT
TGCTCTGCGTTGCGATCCGATTAGTGGTCATGTTAGCCTGTTTTGGTATCAGCAA
GCGCTGGGCCAGGGTCCGGAATTTCTGACCTACTTCCAGAACGAAGCACAACTG
GATAAATCAGGCCTGCCGTCGGACCGTTTCTTTGCTAACGCCCGGAAGGTAGT
GTTTCCACCCTGAAGATTCAGCGTACGCAGCAAGAAGATTCTGCGGTCTATCTG
TGCGCCAGCTCTCTGGGCCAGGCGTATGAACAATACTTTGGTCCGGGTACGCGT
CTGACCGTCACGGAAGATCTGAAAAACGTGTTCCGCCGGAAGTTGCGGTTTTT
GAACCGAGCGAAGCGGAAATTAGCCATACCCAGAAAGCGACCCTGGTTTGTCT
GGCGACCGGTTTTATCCGGATCATGTGGAACTGTCTTGGTGGGTGAACGGCAA
AGAAGTGCATAGCGGTGTTTCTACCGATTGCCAGCCGCTGAAAGAACAGCCGGC
GCTGAATGATAGCCGTTATGCGCTGTCTAGCCGTCTGCGTGTTAGCGCGACCTTT
TGGCAAAATCCGCGTAACCATTTCGTTGCCAGGTGCAGTTTTATGGCCTGAGC
GAAAACGATGAATGGACCCAGGATCGTGCGAAGCCGGTTACCCAGATTGTTAG
CGCGGAAGCCTGGGGCCGCGCAGAT (SEQ ID NO: 12)

Fig. 14b

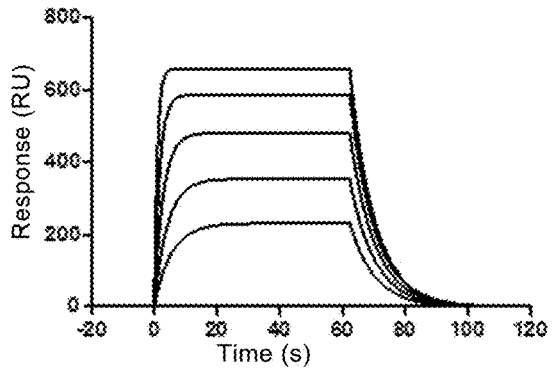

Fig. 18

(LC13 TRAV46 and TRBC60)3D
AQEVTQIPAALSVPEGENLVLNCSFTDSAIYNLQWFRQDCGKGLTSLLLI
QSSQREQTSGRLNASLDKSSGRSTLYIAASQPGDSATYLCAVRPTSGGSYIPT
FGRGTSLIVHPYIQNPDPAVYQLRDSKSSDKSVCLFTDFDSQTNVSQSKDSDV
YITDKTVLDMRSMDFKSNSAVAWSNKSDFACANAFNNSIIPEDTFFPSPESS
 (SEQ ID NO: 13)

Fig. 19

GCACAAGAAGTTACTCAAATTCCGGCGGCGCTGAGCGTTCCGGAAG
GTGAAAACCTGGTGCTGAACTGCAGCTTTACCGATAGCGCGATCTATAAC
CTGCAGTGGTTTCGTCAAGATTGCGGTAAAGGTCTGACCAGCCTGCTGCT
GATTCAGAGCAGCCAGCGTGAACAGACCAGCGGTCGTCTGAATGCGAGC
CTGGATAAAAGCAGCGGTCGTAGCACCCTGTATATTGCGGCGAGCCAGCC
GGGTGATAGCGCAACCTATCTGTGTGCGGTTCGTCCGACCAGCGGTGGTA
GCTATATTCCGACCTTTGGTCGTGGCACCAGCCTGATTGTGCATCCGTATA
TCCAGAATCCGGATCCGGCCGTTTATCAGCTGCGTGATAGCAAAAGCAGC
GATAAAAGCGTGTGCCTGTTCACCGATTTTGATAGCCAGACCAACGTGAG
CCAGAGCAAAGATAGCGATGTGTACATCACCGATAAAACCGTGCTGGAT
ATGCGCAGCATGGATTTCAAAAGCAATAGCGCGGTTGCGTGGAGCAACA
AAAGCGATTTTGCGTGCGCGAACGCGTTTAACAACAGCATCATCCCGGAA
GATACGTTCTTCCCCAGCCCAGAAAGTTCC
 (SEQ ID NO: 14)

Fig. 20

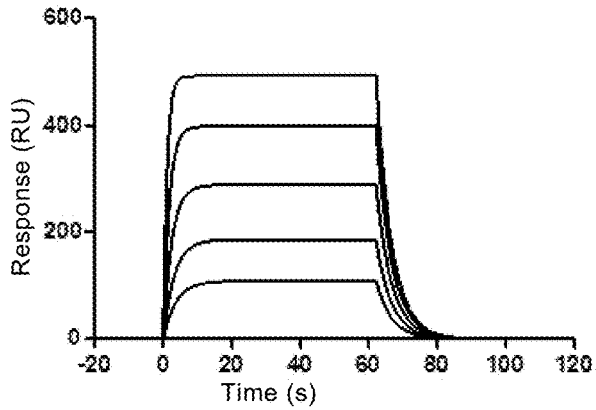

Fig. 24

GQLLEQSPQFLSIQEGENLTVYCNSSSVFSSLQWYRQECGEGPVLLVTVVTGG
EVKKLKRLTFQFGDARKDSSLHITAAQPGDTGLYLCAGAGSQGNLIFGKGTKLSVK
PNIQNPDPAVYQLRDSKSSDKSVCLFTDFDSQTNVSQSKDSDVYITDKTVLDMRSM
DFKSNSAVAWSNKSDFACANAFNNSIIPEDTFFPSPESS (SEQ ID NO: 15)

Fig. 25

GGCCAACTGCTGGAACAATCCCCGCAATTCCTGAGTATTCAAGAAGGCGA
AAATCTGACGGTCTACTGTAATTCATCATCGGTCTTTAGCTCTCTGCAGTGGTAT
CGTCAAGAATGCGGTGAAGGTCCGGTCCTGCTGGTGACCGTGGTTACGGGCGGT
GAAGTGAAAAAGCTGAAACGTCTGACCTTTCAGTTCGGCGATGCGCGCAAGGA
CAGTTCCCTGCATATTACCGCAGCACAGCCGGGTGATACGGGTCTGTACCTGTG
CGCAGGCGCTGGTAGCCAAGGTAACCTGATTTTTGGCAAGGGTACGAAGCTGA
GCGTTAAACCGAACATCCAGAATCCGGATCCGGCCGTTTATCAGCTGCGTGATA
GCAAAAGCAGCGATAAAGCGTGTGCCTGTTCACCGATTTTGATAGCCAGACCA
ACGTGAGCCAGAGCAAAGATAGCGATGTGTACATCACCGATAAAACCGTGCTG
GATATGCGCAGCATGGATTTCAAAAGCAATAGCGCGGTTGCGTGGAGCAACAA
AAGCGATTTTGCGTGCGCGAACGCGTTTAACAACAGCATCATCCCGGAAGATAC
GTTCTTCCCCAGCCCAGAAAGTTCC (SEQ ID NO: 16)

Fig. 26

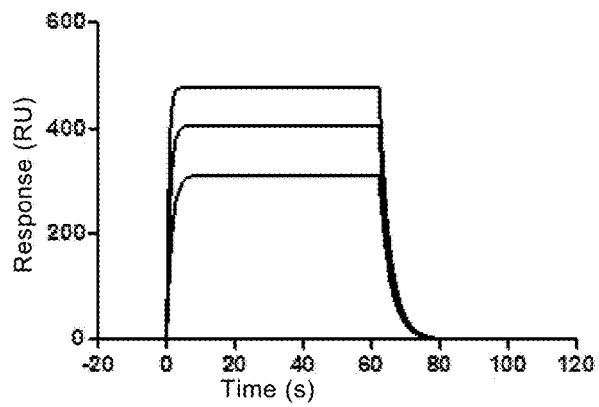

Fig. 30

GKTTQPNSMESNEEEPVHLPCNHSTISGTDYIHWYRQLCSQGPEYVIHGLTSN
VNNRMASLAIAEDRKSSTLILHRATLRDAAVYYCILPLAGGTSYGKLTFGQGTILTV
HPNIQNPDPAVYQLRDSKSSDKSVCLFTDFDSQTNVSQSKDSDVYITDKTVLDMRS
MDFKSNSAVAWSNKSDFACANAFNNSIIPEDTFFPSPESS (SEQ ID NO: 17)

Fig. 31

GGCAAAACCACCCAGCCGAACTCAATGGAAAGCAACGAAGAAGAACCGG
TCCACCTGCCGTGTAATCACAGCACCATCTCAGGCACCGATTATATTCATTGGTA
CCGTCAGCTGTGCAGCCAAGGTCCGGAATATGTGATCCACGGTCTGACCAGTAA
CGTTAACAATCGTATGGCATCCCTGGCAATTGCTGAAGATCGCAAAAGCTCTAC
CCTGATCCTGCATCGTGCAACGCTGCGTGACGCAGCCGTTTATTACTGCATTCTG
CCGCTGGCCGGCGGTACCAGCTACGGCAAGCTGACGTTTGGCCAGGGTACCATT
CTGACGGTCCACCCGAACATCCAGAATCCGGATCCGGCCGTTTATCAGCTGCGT
GATAGCAAAAGCAGCGATAAAGCGTGTGCCTGTTCACCGATTTTGATAGCCAG
ACCAACGTGAGCCAGAGCAAAGATAGCGATGTGTACATCACCGATAAAACCGT
GCTGGATATGCGCAGCATGGATTTCAAAAGCAATAGCGCGGTTGCGTGGAGCA
ACAAAAGCGATTTTGCGTGCGCGAACGCGTTTAACAACAGCATCATCCCGGAAG
ATACGTTCTTCCCCAGCCCAGAAAGTTCC (SEQ ID NO: 18)

Fig. 32

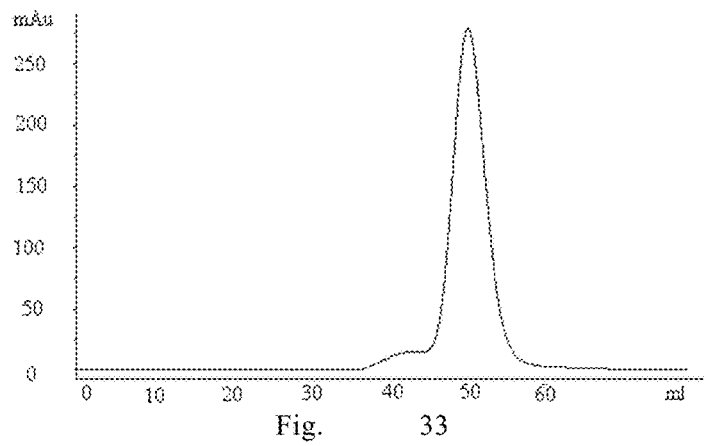
Fig. 33
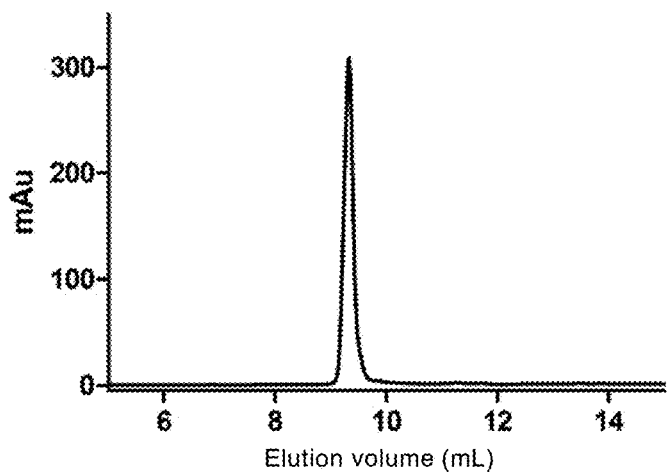
Fig. 34
EDLNKVFPPEVAVFEPSEAEISHTQKATLVCLATGFFPDHVELSWWVNG
KEVHSGVSTDPQPLKEQPALNDSRYCLSSRLRVSATFWQNPRNHFRCQVQFY
GLSENDEWTQDRAKPVTQIVSAEAWGRA (SEQ ID NO.:44)
Fig. 35a
EDLKNVFPPEVAVFEPSEAEISHTQKATLVCLATGFYPDHVELSWWVN
GKEVHSGVSTDPQPLKEQPALNDSRYCLSSRLRVSATFWQNPRNHFRCQVQF
YGLSENDEWTQDRAKPVTQIVSAEAWGRA (SEQ ID NO.:45)
Fig. 35b

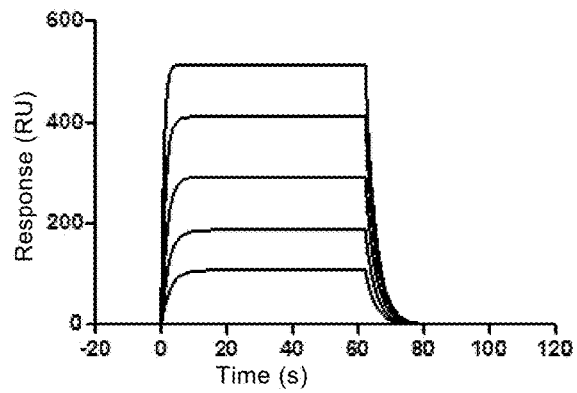

Fig. 36

AQEVTQIPAALSVPEGENLVLNCSFTDSAIYNLQWFRQDP<u>C</u>KGLTSLLLIQSSQ
REQTSGRLNASLDKSSGRSTLYIAASQPGDSATYLCAVRPTSGGSYIPTFGRGTSLIV
HPY (SEQ ID NO: 19)

Fig. 37a

GVTQTPKFQVLKTGQSMTLQCAQDMNHEYMSWYRQDPGMGLRLIHYSVGA
GITDQGEVPNGYNVSRSTTEDFPLRLLSAAPSQTSVYFCASSYVGNTGELFFGEGSR
LTVLEDLKNVFPPEVAVFEPSEAEISHTQKATLVCLATGFYPDHVELSWWVNGKEV
HSGVSTDP<u>C</u>PLKEQPALNDSRYALSSRLRVSATFWQNPRNHFRCQVQFYGLSENDE
WTQDRAKPVTQIVSAEAWGRAD (SEQ ID NO: 20)

Fig. 37b

GCACAAGAAGTTACTCAAATTCCGGCGGCGCTGAGCGTTCCGGAAGGTGA
AAACCTGGTGCTGAACTGCAGCTTTACCGATAGCGCGATCTATAACCTGCAGTG
GTTTCGTCAAGATCCGTGCAAAGGTCTGACCAGCCTGCTGCTGATTCAGAGCAG
CCAGCGTGAACAGACCAGCGGTCGTCTGAATGCGAGCCTGGATAAAAGCAGCG
GTCGTAGCACCCTGTATATTGCGGCGAGCCAGCCGGGTGATAGCGCAACCTATC
TGTGTGCGGTTCGTCCGACCAGCGGTGGTAGCTATATTCCGACCTTTGGTCGTGG
CACCAGCCTGATTGTGCATCCGTAT (SEQ ID NO: 21)

Fig. 38a

GGCGTCACACAAACCCCGAAATTTCAGGTGCTGAAAACGGGTCAGAGCAT
GACCCTGCAGTGTGCGCAGGATATGAACCACGAATACATGAGCTGGTATCGTCA
AGATCCGGGTATGGGTCTGCGTCTGATCCATTATAGCGTGGGTGCGGGCATTAC
CGATCAGGGTGAAGTGCCGAACGGTTATAATGTTAGCCGTAGCACCACCGAAG
ATTTTCCGCTGCGTCTGCTGAGCGCGGCGCCGAGCCAGACCAGCGTTTATTTTG
CGCGAGCAGCTATGTTGGTAACACCGGCGAACTGTTTTTTGGTGAAGGCAGCCG
TCTGACCGTTCTGGAAGATCTGAAAAACGTGTTTCCGCCGGAAGTTGCGGTTTTT
GAACCGAGCGAAGCGGAAATTAGCCATACCCAGAAAGCGACCCTGGTTTGTCT
GGCGACCGGTTTTTATCCGGATCATGTGGAACTGTCTTGGTGGGTGAACGGCAA
AGAAGTGCATAGCGGTGTTTCTACCGATCCGTGCCCGCTGAAAGAACAGCCGGC
GCTGAATGATAGCCGTTATGCGCTGTCTAGCCGTCTGCGTGTTAGCGCGACCTTT
TGGCAAAATCCGCGTAACCATTTTCGTTGCCAGGTGCAGTTTTATGGCCTGAGC
GAAAACGATGAATGGACCCAGGATCGTGCGAAGCCGGTTACCCAGATTGTTAG
CGCGGAAGCCTGGGGCCGCGCAGAT (SEQ ID NO: 22)

Fig. 38b

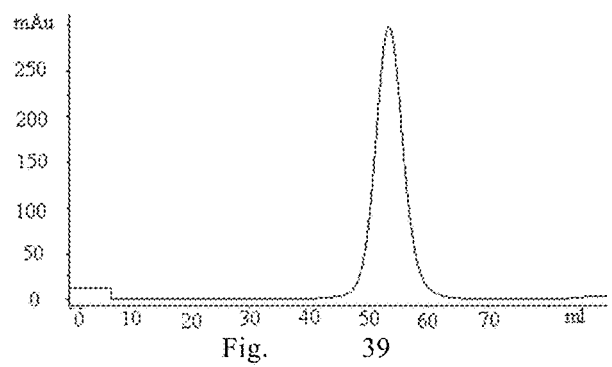

Fig. 39

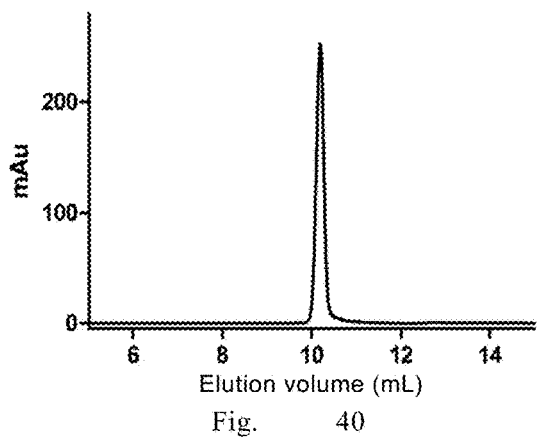

Fig. 40

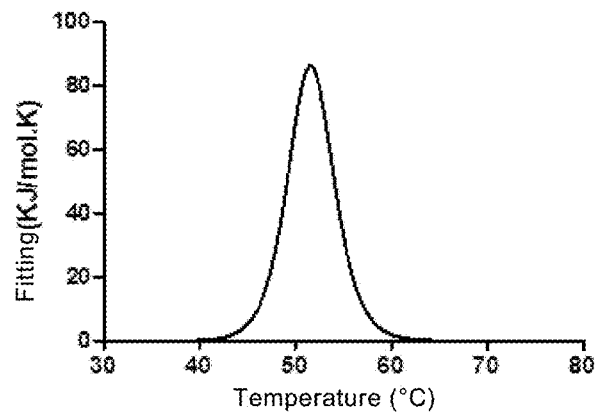
Fig. 41
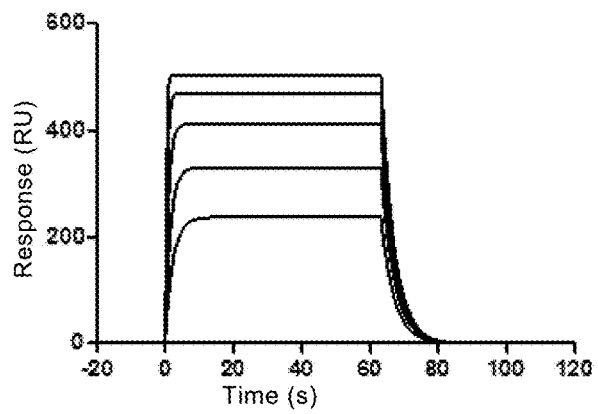
Fig. 42
AQEVTQIPAALSVPEGENLVLNCSFTDSAIYNLQWFRQDP<u>C</u>KGLTSLLLIQSSQ
REQTSGRLNASLDKSSGRSTLYIAASQPGDSATYLCAVRPTSGGSYIPTFGRGTSLIV
HPYIQNPDPAVYQLRDSKSSDKSVCLFTDFDSQTNVSQSKDSDVYITDKTVLDMRS
MDFKSNSAVAWSNKSDFACANAFNNSIIPEDTFFPSPESS (SEQ ID NO: 23)
Fig. 43

ATGGCACAAGAAGTTACTCAAATTCCGGCGGCGCTGAGCGTTCCGGAAGG
TGAAAACCTGGTGCTGAACTGCAGCTTTACCGATAGCGCGATCTATAACCTGCA
GTGGTTTCGTCAAGATCCGTGCAAAGGTCTGACCAGCCTGCTGCTGATTCAGAG
CAGCCAGCGTGAACAGACCAGCGGTCGTCTGAATGCGAGCCTGGATAAAAGCA
GCGGTCGTAGCACCCTGTATATTGCGGCGAGCCAGCCGGGTGATAGCGCAACCT
ATCTGTGTGCGGTTCGTCCGACCAGCGGTGGTAGCTATATTCCGACCTTTGGTCG
TGGCACCAGCCTGATTGTGCATCCGTATATCCAGAATCCGGATCCGGCCGTTTA
TCAGCTGCGTGATAGCAAAAGCAGCGATAAAAGCGTGTGCCTGTTCACCGATTT
TGATAGCCAGACCAACGTGAGCCAGAGCAAAGATAGCGATGTGTACATCACCG
ATAAAACCGTGCTGGATATGCGCAGCATGGATTTCAAAAGCAATAGCGCGGTTG
CGTGGAGCAACAAAAGCGATTTTGCGTGCGCGAACGCGTTTAACAACAGCATC
ATCCCGGAAGATACGTTCTTCCCCAGCCCAGAAAGTTCC (SEQ ID NO: 24)

Fig. 44

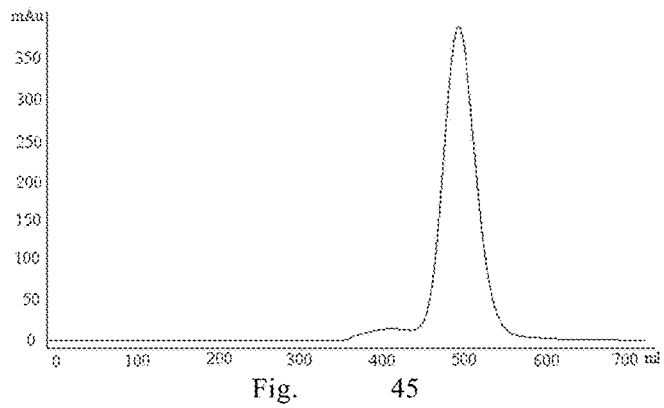

Fig. 45

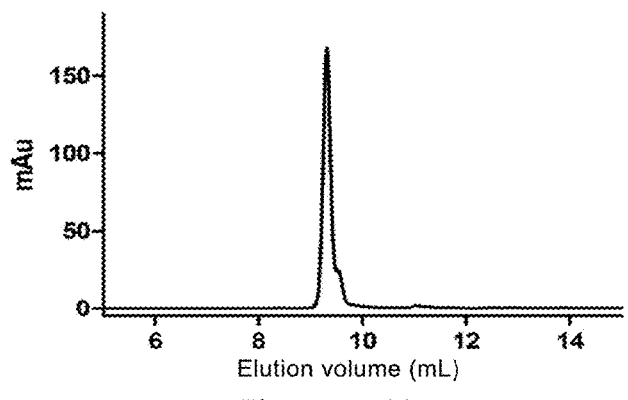

Fig. 46

SOLUBLE AND STABLE HETERODIMERIC TCR

CROSS-REFERENCE TO RELATED APPLICATIONS

The present application is a § 371 National Phase Application of PCT/CN2016/077680, filed Mar. 29, 2016, which application claims priority to CN 201510260322.4, filed May 20, 2015, the disclosures of which are hereby incorporated by reference in their entireties for all purposes.

REFERENCE TO SUBMISSION OF A SEQUENCE LISTING AS A TEXT FILE

The Sequence Listing written in file SUBSEQ_096410-003100US-1067524_SubSequenceListing.TXT created on Jan. 3, 2018, 37,488 bytes, machine format IBM-PC, MS-Windows operating system, is hereby incorporated by reference in its entirety for all purposes.

TECHNICAL FIELD

The present invention relates to field of biomedicine, and in particular to a soluble T cell receptor, and preparation method and uses thereof.

BACKGROUND

There are only two types of molecules that can recognize antigens in a specific manner. One is immunoglobulin or antibody and the other is T cell receptor (TCR), which is α/β or γ/δ heterodimeric glycoprotein on cell membrane. TCR heterodimers consist of α and β chains in 95% T cells, while in 5% T cells, TCR consists of γ and δ chains. Natural αβ hetero-dimeric TCRs have α-chain and β-chain, and α-chain and β-chain form subunit of αβ heterodimeric TCR. Generally, α and β chains of TCR are considered to have two "domains", that is, TCRα chain variable domain (Vα) and TCRα chain constant domain (Cα), and TCRβ chain variable domain (Vβ) and TCRβ chain constant domain (Cβ).

TCR is the only receptor for presenting specific peptide antigens in Major Histocompatibility Complex (MHC). The exogenous or endogenous peptides may be the only sign of abnormality in a cell. In the immune system, once antigen-specific TCRs bind with pMHC complexes, it causes direct physical contact of a T-cell and an antigen presenting cell (APC). Then, the interaction of other membrane molecules in T cell and APC occurs and the subsequent cell signaling and other physiological responses are initiated so that a range of different antigen-specific T cells exert immune effects on their targets. Therefore, TCR is essential for the cellular immune function of the immune system.

Just like an immunoglobulin (antibody) which can be used as an antigen recognition molecule, TCR can be developed for diagnostic and therapeutic applications. There are many applications for soluble TCRs, which can be not only used in study of interaction of TCR-pMHC but also as a diagnostic tool for detecting infection or as a marker for autoimmune disease. Similarly, soluble TCRs can be used to deliver a therapeutic agent, such as a cytotoxic compound or an immunostimulatory compound, to cells presenting specific antigens or to inhibit T cells (e.g., the T cells which react with autoimmune peptide antigens). Furthermore, soluble TCRs can bind to other molecules (e.g., anti-CD3 antibodies) and re-direct T cells, so as to target and kill cells which present specific antigens.

Naturally occurring TCR is a membrane protein which is stabilized by its transmembrane region. For obtaining a soluble TCR protein, it is very difficult to obtain a soluble and stable TCR maintaining the ability to bind to its original ligand (i.e., pMHC) (Shin, et al., (1993) science 259: 1901). Instability and low protein yield are major obstacles for using TCRs or fragments thereof in the development of therapeutic or diagnostic agents. Some literatures describe a truncated form of TCR that only contains extracellular region or extracellular and cytoplasmic regions. Although such TCRs can be recognized by TCR-specific antibodies, the yield is low and when at a low concentration, can not identify MHC-peptide complex, indicating that it is easily denatured, and not stable enough. A skilled person in the art is making effort to develop soluble, stable T cell receptors.

SUMMARY OF THE INVENTION

The object of the present invention is to provide a soluble and stable heterodimeric TCR, and uses thereof.

In the first aspect of the invention, a αβ heterodimeric TCR is provided, wherein an artificial interchain disulfide bond is contained between α chain variable region and β chain constant region of the TCR.

In another preferred embodiment, the artificial interchain disulfide bonds of the TCR are located between FR2 of α chain variable region and constant region of β chain.

In another preferred embodiment, a cysteine residue that forms the artificial interchain disulfide bond of the TCR substitutes for an amino acid residue at position 46 or 47 of TRAV.

In another preferred embodiment, a cysteine residue that forms the artificial interchain disulfide bond of the TCR substitutes for an amino acid residue at position 60 or 61 of TRBC1*01 or TRBC2*01 exon 1.

In another preferred embodiment, cysteine residues that form the artificial interchain disulfide bond of the TCR substitute for:

an amino acid residue at position 46 of TRAV and an amino acid residue at position 60 of TRBC1*01 or TRBC2*01 exon 1;

an amino acid residue at position 47 of TRAV and an amino acid residue at position 61 of TRBC1*01 or TRBC2*01 exon 1;

an amino acid residue at position 46 of TRAV and an amino acid residue at position 61 of TRBC1*01 or TRBC2*01 exon 1; or an amino acid residue at position 47 of TRAV and an amino acid residue at position 60 of TRBC1*01 or TRBC2*01 exon 1.

In another preferred embodiment, the TCR is soluble.

In another preferred embodiment, the TCR comprises α chain variable domain and β chain variable domain as well as all or part of β chain constant domains other than its transmembrane domain, however it does not comprise α chain constant domain, and α chain variable domain and β chain of the TCR form a heterodimer.

In another preferred embodiment, the cysteine residue in β chain constant domain for forming a natural interchain disulfide bond is replaced with another amino acid; preferably Ala or Ser.

In another preferred embodiment, the β chain constant domain of the TCR is truncated at C-terminus, thereby removing cysteine residues for forming natural interchain disulfide bonds.

In another preferred embodiment, the TCR comprises: (i) all or part of the TCR α chain other than its transmembrane domain, and (ii) all or part of the TCR β chain other than its transmembrane domain, wherein both of (i) and (ii) comprise variable domain and at least a portion of constant domains of TCR chain.

In another preferred embodiment, there is no natural interchain disulfide bond between α and β chain constant domain of the TCR.

In another preferred embodiment, α chain and/or β chain constant region of the TCR are truncated at C-terminus, thereby removing cysteine residues for forming natural interchain disulfide bonds.

In another preferred embodiment, the cysteine residue in α chain and/or β chain constant region of the TCR for forming a natural interchain disulfide bond is substituted with another residue.

In another preferred embodiment, there is an artificial interchain disulfide bond between α chain constant region and β chain constant region of the TCR.

In another preferred embodiment, cysteine residues that form the artificial interchain disulfide bond between α chain constant region and β chain constant region of the TCR substitute for:

48T of TRAC1*01 exon 1 and 57S of TRBC1*01 or TRBC2*01 exon 1;
45T of TRAC1*01 exon 1 and 77S of TRBC1*01 or TRBC2*01 exon 1;
10Y of TRAC1*01 exon 1 and 17S of TRBC1*01 or TRBC2*01 exon 1;
45T of TRAC1*01 exon 1 and 59D of TRBC1*01 or TRBC2*01 exon 1;
15S of TRAC1*01 exon 1 and 15E of TRBC1*01 or TRBC2*01 exon 1;
53R of TRAC1*01 exon 1 and 54S of TRBC1*01 or TRBC2*01 exon 1;
89P of TRAC1*01 exon 1 and 19A of TRBC1*01 or TRBC2*01 exon 1; or
10Y of TRAC1*01 exon 1 and 20E of TRBC1*01 or TRBC2*01 exon 1.

In another preferred embodiment, a conjugate is bound with C- or N-terminus of the TCR α chain and/or β chain.

In a preferred embodiment, the conjugate bound with the TCR is selected from a group consisting of: a detectable marker; a therapeutic agent; a PK modifying moiety and a combination thereof.

In another preferred embodiment, the therapeutic agent bound with the TCR is anti-CD3 antibody which is linked at C- or N-terminus of α and/or β chains of the TCR.

In another preferred embodiment, Tm value of the TCR is ≥45° C.; preferably, ≥50° C.; more preferably, ≥52° C.; most preferably, ≥55° C.

In the second aspect of the invention, a nucleic acid molecule is provided, comprising a nucleic acid sequence encoding α chain and/or β chain of the TCR according to the first aspect of the invention, or its complementary sequence.

In the third aspect of the invention, a vector is provided, comprising a nucleic acid molecule according to the second aspect of the invention.

In the fourth aspect of the invention, a host cell or a genetically engineered cell is provided, which comprises the vector according to the third aspect of the invention or in which the exogenous nucleic acid molecule according to the second aspect of the invention is integrated in chromosome.

In the fifth aspect of the invention, an isolated cell is provided, which expresses the TCR according to the first aspect of the invention In the sixth aspect of the invention, a method for preparing the T-cell receptor according to the first aspect of the invention is provided, which comprises:

(i) culturing the host cell according to the fourth aspect of the invention, thereby expressing α chain and/or β chain of the T-cell receptor of the first aspect of the invention;

(ii) isolating or purifying the α chain and/or chain; and (iii) refolding the α chain and/or β chain, thereby obtaining the T-cell receptor.

In the seventh aspect of the invention, a T-cell receptor complex is provided, comprising one or more TCR molecules of the first aspect of the invention.

In the eighth aspect of the invention, use of the TCR of the first aspect of the invention is provided for manufacture of a medicine for treating tumor, viral infection or autoimmune disease or a reagent for detecting MHC-peptide complexes.

In the ninth aspect of the invention, a pharmaceutical composition is provided comprising a pharmaceutically acceptable carrier and a safe and effective dosage of the TCR of the first aspect of the invention, the cell of the fifth aspect of the invention, or the TCR complex of the seventh aspect of the invention.

In the tenth aspect of the invention, a method for treating a disease is provided, comprising administering the TCR of the first aspect of the invention, the cell of the fifth aspect of the invention, or the TCR complex of the seventh aspect of the invention, or the pharmaceutical composition of the ninth aspect of the invention to a subject in need thereof.

Preferably, the disease includes tumor, autoimmune disease or viral infection.

It should be understood that in the present invention, the technical features specifically described above and below (such as the examples) can be combined with each other, thereby constituting a new or preferred technical solution, which needs not be specified one by one.

DESCRIPTION OF DRAWINGS

FIG. 1a and FIG. 1b are α chain variable domain amino acid sequence and β chain amino acid sequence of three-domain 1G4TCR molecule, respectively, wherein an artificial interchain disulfide bond is formed at position 46 of TRAV and position 60 of TRBC1*01 or TRBC2*01 exon 1.

FIGS. 2a and 2b respectively show the nucleotide sequences corresponding to the amino acid sequences in FIGS. 1a and 1b.

FIG. 6 shows binding curves of 1G4TCR molecule obtained from TCR α chain variable domain and β chain as shown in FIGS. 1a and 1b at different concentrations with its corresponding antigen, after refolding and protein purification.

FIG. 7a and FIG. 7b are α chain variable domain amino acid sequence and β chain amino acid sequence of three-domain JM22TCR molecule, respectively, wherein an artificial interchain disulfide bond is formed at position 46 of TRAV and position 60 of TRBC1*01 or TRBC2*01 exon 1.

FIGS. 8a and 8b respectively show the nucleotide sequences corresponding to the amino acid sequences in FIGS. 7a and 7b.

FIG. 9 shows an elution curve of gel filtration column of TCR α chain variable domain and β chain as shown in FIGS. 1a and 1b after refolding.

FIG. 13a and FIG. 13b are α chain variable domain amino acid sequence and β chain amino acid sequence of three-domain LC13TCR molecule, respectively, wherein an artificial interchain disulfide bond is formed at position 46 of TRAV and position 60 of TRBC1*01 or TRBC2*01 exon 1.

FIGS. 14a and 14b respectively show the nucleotide sequences corresponding to the amino acid sequences in FIGS. 13a and 13b.

FIG. 18 shows binding curves of LC13TCR molecule obtained from TCR α chain variable domain and β chain as shown in FIGS. 13a and 13b at different concentrations with its corresponding antigen, after refolding and protein purification.

FIG. 19 is α chain amino acid sequence of four-domain 1G4 molecule, wherein an artificial interchain disulfide bond is formed at position 46 of TRAV and position 60 of TRBC1*01 or TRBC2*01 exon 1.

FIG. 20 shows the nucleotide sequences corresponding to the amino acid sequences in FIG. 19.

FIG. 24 shows binding curves of 1G4TCR molecule at different concentrations with its corresponding antigen, wherein the molecule is obtained from α chain and β chain of four-domain TCR after refolding and protein purification, and an artificial interchain disulfide bond is formed at position 46 of TRAV and position 60 of TRBC1*01 or TRBC2*01 exon 1.

FIG. 25 is α chain amino acid sequence of four-domain JM22 molecule, wherein an artificial interchain disulfide bond is formed at position 46 of TRAV and position 60 of TRBC1*01 or TRBC2*01 exon 1.

FIG. 26 shows the nucleotide sequences corresponding to the amino acid sequences in FIG. 25.

FIG. 30 shows binding curves of JM22TCR molecule at different concentrations with its corresponding antigen, wherein the molecule is obtained from α chain and β chain of four-domain TCR after refolding and protein purification, and an artificial interchain disulfide bond is formed at position 46 of TRAV and position 60 of TRBC1*01 or TRBC2*01 exon 1.

FIG. 31 is α chain amino acid sequence of four-domain LC13 molecule, wherein an artificial interchain disulfide bond is formed at position 46 of TRAV and position 60 of TRBC1*01 or TRBC2*01 exon 1.

FIG. 32 shows the nucleotide sequences corresponding to the amino acid sequences in FIG. 31.

FIG. 33 shows an elution curve of gel filtration column of α chain and chain of four-domain LC13TCR after refolding, wherein an artificial interchain disulfide bond is formed at position 46 of TRAV and position 60 of TRBC1*01 or TRBC2*01 exon 1.

FIG. 34 shows a SEC spectrum of α chain and chain of four-domain LC13TCR after refolding and protein purification, wherein an artificial interchain disulfide bond is formed at position 46 of TRAV and position 60 of TRBC1*01 or TRBC2*01 exon 1.

FIGS. 35a and 35b are amino acid sequences of TRBC1*01 and TRBC2*01 listed in IMGT, respectively.

FIG. 36 shows binding curves of LC13TCR molecule at different concentrations with its corresponding antigen, wherein the molecule is obtained from α chain and β chain of four-domain TCR after refolding and protein purification, and an artificial interchain disulfide bond is formed at position 46 of TRAV and position 60 of TRBC1*01 or TRBC2*01 exon 1.

FIG. 37a and FIG. 37b are α chain variable domain amino acid sequence and β chain amino acid sequence of three-domain 1G4TCR molecule, respectively, wherein an artificial interchain disulfide bond is formed at position 47 of TRAV and position 61 of TRBC1*01 or TRBC2*01 exon 1.

FIGS. 38a and 38b respectively show the nucleotide sequences corresponding to the amino acid sequences in FIGS. 37a and 37b.

FIG. 39 shows an elution curve of gel filtration column of TCR α chain variable domain and β chain as shown in FIGS. 37a and 37b after refolding.

FIG. 40 shows a SEC spectrum of TCR α chain variable domain and β chain as shown in FIGS. 37a and 37b after refolding and protein purification.

FIG. 41 shows a DSC thermogram of TCR α chain variable domain and β chain as shown in FIGS. 37a and 37b after refolding and protein purification.

FIG. 42 shows binding curves of TCR molecule obtained from TCR α chain variable domain and β chain as shown in FIGS. 37a and 37b at different concentrations with its corresponding antigen, after refolding and protein purification.

FIG. 43 is α chain amino acid sequence of four-domain 1G4TCR molecule, wherein an artificial interchain disulfide bond is formed at position 47 of TRAV and position 61 of TRBC1*01 or TRBC2*01 exon 1.

FIG. 44 shows the nucleotide sequences corresponding to the amino acid sequences in FIG. 43.

FIG. 45 shows an elution curve of gel filtration column of α chain and β chain of four-domain TCR after refolding, wherein an artificial interchain disulfide bond is formed at position 47 of TRAV and position 61 of TRBC1*01 or TRBC2*01 exon 1.

FIG. 46 shows a SEC spectrum of α chain and β chain of four-domain TCR after refolding and protein purification, wherein an artificial interchain disulfide bond is formed at position 47 of TRAV and position 61 of TRBC1*01 or TRBC2*01 exon 1.

MODES FOR CARRYING OUT THE INVENTION

Figure 3:
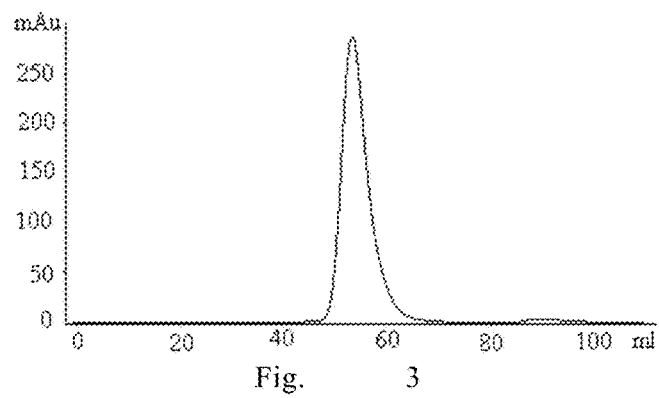
FIG. 3 shows an elution curve of gel filtration column of TCR α chain variable domain and β chain as shown in FIGS. 1a and 1b after refolding.

Through extensive and intensive researches, the inventors have unexpectedly obtained a soluble and stable T cell receptor. In particular, the present invention provides a αβ heterodimer, and a covalent artificial interchain disulfide bond is present between α chain variable region and chain constant region of the TCR of the present invention. Especially, for the TCR of the present invention, the artificial interchain disulfide bond is present between FR2 of α chain and constant region of β chain. Uses of the TCR and preparing methods therefor are also provided in the present invention.

Before describing the present invention, it is to be understood that the present invention is not limited to the described particular method and experiment conditions, as such method and condition may be varied. It is also to be understood that the term used herein is for the purpose of describing particular embodiments only, and is not intended to be in anyway of a limitation, and the scope of the invention will be limited solely by the appended claims.

Unless otherwise defined, all technical and scientific terms used herein have the same meaning as commonly understood by a skilled person in the art to which the present invention belongs.

Although any methods and materials similar or equivalent to those described in this disclosure may be used in the practice or testing of the present invention, the preferred methods and materials are exemplified herein.

Terms

T Cell Receptor

Natural αβ heterodimeric TCRs have α and β chains, and α and β chains form two subunits of αβ heterodimeric TCRs. Each of α and β chains of TCR is generally considered as having two "domains", i.e., TCR α chain variable domain (Vα) and TCR α chain constant domain (Cα), TCR β chain variable domain (Vβ) and TCR β chain constant domain (Cβ). A set of disulfide bonds exist between Cα and Cβ chains of membrane-proximal region of TCR, named as "natural interchain disulfide bonds" in the present invention. In the present invention, an artificially introduced interchain covalent disulfide bond, the position of which is different from that of natural interchain disulfide bond is named as "artificial interchain disulfide bond". In the present invention, terms "polypeptide of the present invention", "TCR of the present invention" and "T cell receptor of the present invention" can be used interchangeably to refer to a heterodimeric TCR containing the artificial interchain disulfide bond of the present invention between α chain variable region and β chain constant region.

Generally, each of TCR α and β chains comprises a variable region, a linker region, and a constant region, and β chain typically also comprises a short, diversity region between the variable region and the linker region, however, the diversity region is often deemed as a part of the linker region. Each of α and β chains of a TCR are generally deemed as having two "domains", i.e., variable domain and constant domain. The variable domain consists of variable region and linker region. And the constant domain also comprises transmembrane region and cytoplasmic region which is very short.

Nomenclature of the TCR of the present invention employs the nomenclature for TCR in International Immunogenetics Information System (IMGT). That is, in this system, "TRAC*01" indicates α chain constant region of a TCR, wherein "TR" indicates a T cell receptor gene, "A" indicates α chain gene, C indicates constant region, and "01" indicates allele 1. Similarly, "TRBC1*01" or "TRBC2*01" indicates β chain constant domain. There are two possible constant region genes "C1" and "C2" in β chain.

Sequences of TRAC*01 and TRBC1*01 or TRBC2*01 given in IMGT are well-known and available to a skilled person in the art, which can be found, for example, in IMGT public database (http://www.imgt.org/).

"TRAV" represents α chain variable region of a TCR, wherein "TR" represents T cell receptor gene, "A" represents α chain gene and V represents variable region. Similarly, "TRBV" represents β chain variable region of a TCR. Each variable region comprises three framework regions (FRs) and three CDRs (complement determining regions), CDR1, CDR2 and CDR3 which are chimeric in the backbone. CDR regions, in particular CDR3, determine the diversity of a TCR and the binding of TCR to pMHC complexes. 3 skeletal structures are FR1, position numbers of which is 1-26 in IMGT; FR2, position number of which is 39-55 in IMGT; and FR3, position number of which is 66-104 in IMGT, respectively. Skeletal structures of different TCR molecules are very similar (K. Christopher Garcia, et al., Annu. Rev. Immunol. 1999.17: 369-397), and the skeletal structures of TCR variable region given in IMGT and the position numbers in IMGT are well-known and available to a skilled person in the art, which can be found, for example, in IMGT public database (http://www.imgt.org/).

For convenience of description, positions of the TRAC*01 and TRBC1*01 or TRBC2*01 amino acid sequences in the present invention are sequentially numbered following the order from N-terminus to C-terminus. For example, in TRBC1*01 or TRBC2*01, the 60th amino acid is P (proline) following the order from N-terminus to C-terminus, which may be described as 60P of TRBC1*01 or TRBC2*01 exon 1 in the present invention, and can also be expressed as the amino acid at position 60 of TRBC1*01 or TRBC2*01 exon 1. For another example, in TRBC1*01 or TRBC2*01, the 61th amino acid is Q (glutamine) following the order from N-terminus to C-terminus, which may be described as 61Q of TRBC1*01 or TRBC2*01 exon 1 in the present invention, and can also be expressed as the amino acid at position 61 of TRBC1*01 or TRBC2*01 exon 1, and so on. The amino acid sequences of TRBC1*01 and TRBC2*01 from N-terminal to C-terminal are shown in FIGS. 35a and 35b, respectively. In the present invention, positions of the amino acid sequences of variable regions TRAV and TRBV are numbered according to the position listed in IMGT. For example, if the position number of an amino acid in TRAV listed in IMGT is 46, it is described herein as an amino acid at position 46 of TRAV, and so on. Summing up, the position of an amino acid in TRAV mentioned in the present invention is numbered according to the position of the amino acid sequence listed in IMGT, and the position of an amino acid in TRBC1*01 or TRBC2*01 is numbered following the order from N terminus to C terminus. It should be noted that the position numbers of the amino acid sequences listed in the IMGT are not completely the same as the position numbers of the amino acid sequences following the order from N-terminus to C-terminus.

There is a unique constant region TRAC*01 in α chain of TCR, and two constant regions in β chain are only slightly different. 4N, 5K and 37F are present in TRBC1*01 exon 1, while 4K, 5N and 37Y in TRBC2*01 exon 1. Therefore, there is substantially no difference whether the constant region of β chain in a TCR molecule is TRBC1*01 or TRBC2*01.

Stability

The term "stability" refers to any aspect regarding protein stability, including renaturability, expression ability, protein renaturation yield, thermal stability and resistance to unfolding and the like; preferably, protein renaturation yield and thermal stability.

Three-Domain TCR

The term "three-domain TCR" means that the TCR comprises α chain variable domain and β chain variable domain as well as all or part of β chain constant domain other than its transmembrane domain, however it does not comprise α chain constant domain, α chain variable domain and β chain form a heterodimer, and the α chain variable region and β chain constant region of the TCR are connected by an artificial interchain disulfide bond.

Four-Domain TCR

The term "four-domain TCR" means that the TCR comprises: (i) all or part of the TCR α chain other than its transmembrane domain, and (ii) all or part of the TCR β chain other than its transmembrane domain, wherein both of (i) and (ii) comprise variable domain and at least a portion of constant domains of TCR chain, α chain and β chain form a heterodimer, and an artificial interchain disulfide bond links α chain variable region and β chain constant region of the TCR.

DETAILED DESCRIPTION OF THE PRESENT INVENTION

In the present invention, a soluble and stable heterodimeric T-cell receptor was obtained by introducing a covalent artificial interchain disulfide bond between α chain variable region and β chain constant region of TCR. In particular, for the TCR of the present invention, the artificial interchain disulfide bond is present between FR2 of α chain variable region (TRAV) and β chain constant region. More specifically, the position that forms an artificial interchain disulfide bond may be present between an amino acid residue at position 46 or 47 of TRAV and a suitable position in β chain constant region. Similarly, the position that forms an artificial interchain disulfide bond may be present between an amino acid residue at position 60 or 61 of TRBC1*01 or TRBC2*01 exon 1 and a suitable position in α chain variable region.

In a preferred embodiment, cysteine residues that form an artificial interchain disulfide bond of the TCR of the present invention substitute for:

an amino acid residue at position 46 of TRAV and an amino acid residue at position 60 of TRBC1*01 or TRBC2*01 exon 1;

an amino acid residue at position 47 of TRAV and an amino acid residue at position 61 of TRBC1*01 or TRBC2*01 exon 1;

an amino acid residue at position 46 of TRAV and an amino acid residue at position 61 of TRBC1*01 or TRBC2*01 exon 1; or an amino acid residue at position 47 of TRAV and an amino acid residue at position 60 of TRBC1*01 or TRBC2*01 exon 1.

Preferably, an amino acid residue at position 46 of TRAV can be D, A, P, T, S, C, L, H, Y or K; and an amino acid residue at position 47 of TRAV can be G, N, S, R, W, A or K.

In a preferred embodiment of the present invention, the TCR of the present invention is a three-domain TCR, that is, the TCR comprises α chain variable domain and β chain variable domain as well as all or part of β chain constant domains other than its transmembrane domain, however it does not comprise α chain constant domain, α chain variable domain and β chain form a heterodimer, and the α chain variable region and β chain constant region of the TCR are connected by an artificial interchain disulfide bond.

Preferably, the β chain of the three-domain TCR of the invention comprises all of constant domains other than the transmembrane domain (i.e., comprises extracellular and cytoplasmic domains). In this case, the cysteine residue forming a natural interchain disulfide bond in β chain is preferably mutated to other amino acid residues which do not participate in the formation of disulfide bonds, preferably alanine or serine.

More preferably, the β chain of the three-domain TCR of the present invention comprises part of constant domains other than the transmembrane domain. In such case, the cysteine residue forming a natural interchain disulfide bond in β chain is preferably mutated to other amino acid residues which do not participate in the formation of disulfide bonds, preferably alanine or serine. Alternatively, β chain constant domain of the TCR is truncated at C-terminus, thereby removing cysteine residues for forming natural interchain disulfide bonds. Preferably, it can be truncated at 1, 2, 3, 4, 5, 6, 7, 8, 9 or 10 or more amino acids from the cysteine residue forming a natural interchain disulfide bond, thereby removing cysteines that form a natural interchain disulfide bond.

In another preferred embodiment of the present invention, the TCR of the present invention is a four-domain TCR, that is, the TCR comprises: (i) all or part of the TCR α chain other than its transmembrane domain, and (ii) all or part of the TCR β chain other than its transmembrane domain, wherein both of (i) and (ii) comprise variable domain and at least a portion of constant domains of TCR chain, α chain and β chain form a heterodimer, and an artificial interchain disulfide bond links α chain variable region and β chain constant region of the TCR.

Preferably, the four-domain TCR of the present invention does not comprise a natural interchain disulfide bond. In one aspect, α and/or β chain of the four-domain TCR of the present invention may comprise all of constant domains other than the transmembrane domain (i.e., comprise extracellular and cytoplasmic domains). In such case, the cysteine residue in each chain forming a natural interchain disulfide bond is preferably mutated to other amino acid residues which do not participate in the formation of disulfide bonds, preferably alanine or serine. On the other hand, α and/or β chain of the four-domain TCR of the present invention may comprise part of constant domains other than the transmembrane domain. In such case, the cysteine residue in each chain forming a natural interchain disulfide bond is preferably mutated to other amino acid residues which do not participate in the formation of disulfide bonds, preferably alanine or serine. More preferably, constant domains of TCR α and/or β chain are truncated at C-terminus, thereby removing cysteine residues for forming natural interchain disulfide bonds. Preferably, it can be truncated at 1, 2, 3, 4, 5, 6, 7, 8, 9 or 10 or more amino acids from the cysteine residue forming a natural interchain disulfide bond, thereby removing cysteines that form a natural interchain disulfide bond. It should be noted, however, that the TCR of the present invention may also comprise natural interchain disulfide bonds.

The four-domain TCR of the present invention may comprise an artificial interchain disulfide bond between α and β chain constant domains, and cysteine residues that form the artificial interchain disulfide bond as said above substitute for:

48T of TRAC1*01 exon 1 and 57S of TRBC1*01 or TRBC2*01 exon 1;

45T of TRAC1*01 exon 1 and 77S of TRBC1*01 or TRBC2*01 exon 1;

10Y of TRAC1*01 exon 1 and 17S of TRBC1*01 or TRBC2*01 exon 1;

45T of TRAC1*01 exon 1 and 59D of TRBC1*01 or TRBC2*01 exon 1;

15S of TRAC1*01 exon 1 and 15E of TRBC1*01 or TRBC2*01 exon 1;

53R of TRAC1*01 exon 1 and 54S of TRBC1*01 or TRBC2*01 exon 1;

89P of TRAC1*01 exon 1 and 19A of TRBC1*01 or TRBC2*01 exon 1; or 10Y of TRAC1*01 exon 1 and 20E of TRBC1*01 or TRBC2*01 exon 1.

It should be noted that, in some cases, only one TCR chain has a cysteine for forming a natural interchain disulfide bond, which is used to link the TCR molecule having an artificial interchain disulfide bond of the present invention with other molecules. When β chain of TCR comprises a free unpaired cysteine residue, it is preferred in the present invention that said cysteine is mutated into another amino acid, such as Ser or Ala.

It is to be understood that constant domain of TCR is not directly involved in the binding of TCR to pMHC and that the truncation of a certain number of amino acid residues at the C-terminus will not substantially affect the function of TCR. Therefore, each chain of the TCR of the invention may be further shortened. The binding affinity (inversely proportional to dissociation equilibrium constant KD) of the TCR of invention with its corresponding antigen can be determined by any suitable method. In a preferred embodiment of the invention, the binding of TCR with its corresponding pMHC is measured by forteBIO Oke, as described in Example 4 of the invention.

An appropriate amount of mutation can be introduced in the TCR chain of the present invention without affecting its antigen specificity and functionality. Other mutations include, but are not limited to, deletion, insertion, and substitution of 1 to 6 amino acids (usually 1 to 5, preferably 1 to 3, more preferably 1 to 2, preferably 1); adding one or more (usually 5 or less, preferably 3 or less, and more preferably 2 or less) amino acids at C-terminus and/or N-terminus. For example, in the art, substitution with a functionally similar amino acid usually does not alter the function of protein. The addition of one or more amino acids at C-terminus and/or N-terminus usually does not alter the structure and function of protein.

A soluble and stable T cell receptor of the present invention can be obtained by introducing an artificial interchain disulfide bond between α chain variable region and β chain constant region of a TCR. Moreover, in the present invention, suitable sites in α chain variable region and β chain constant region are identified which can be mutated into Cys to form an artificial interchain disulfide bond. Not only the TCR of the present invention may comprise human TCRs, but also a soluble and stable TCR from other species can be obtained by a skilled person according to the information provided in the present invention.

Although α chain variable region and/or β chain constant region of a TCR from other species may be not 100% identical with corresponding part of human TCR chains, a skilled person in the art can identify the equivalent part in the corresponding TCR so as to obtain a cysteine residue to be mutated. For example, ClustalW available at the website of European Institute of Bioinformatics can be used to compare TCR chains from other species with the corresponding part of human TCR to obtain the corresponding site.

The present invention includes a soluble and stable human αβ heterodimeric TCR comprising an artificial interchain disulfide bond, as well as αβTCRs from other mammal linked with an artificial interchain disulfide bond. Such mammals include, but are not limited to, goat, sheep, pig, mouse and rat.

It should be understood, amino acid names used herein are internationally accepted single alphabetical identity and its corresponding abbreviations of amino acid name with three English letters. They are Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y), and Val (V).

The present invention further includes the active fragments, derivatives and analogs of the polypeptide of the present invention. The polypeptide fragments, derivatives or analogs of the present invention may be (i) a polypeptide with one or more conservative or non-conservative amino acid residues (preferably the conservative amino acid residues) being substituted, or (ii) a polypeptide having substituted group(s) in one or more amino acid residues, or (iii) a polypeptide formed by fusion of TCR of the present invention with another compound (such as the compound that prolongs the half life of the polypeptide, such as polyethylene glycol), or (iv) a polypeptide with additional amino acid sequence fused to said polypeptide sequence, such as fusion proteins formed by fusion with leader sequence, secretion sequence or tag sequence, such as 6His. According to the teaching of present invention, these fragments, derivatives and analogs are within the scope commonly known by the skilled person.

A class of preferred active derivatives refers to polypeptides formed by replacing at most 5, preferably at most 3, more preferably at most 2, and most preferably 1 amino acid of the amino acid sequence of the polypeptide of the present invention with an amino acid having similar or analogous property. These conservative variant polypeptides are preferably formed by carrying out the amino acid replacement according to Table A.

TABLE A

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |

TABLE A-continued

| Initial residue | Representative substitution | Preferred substitution |
|---|---|---|
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides the analogues of TCR of the present invention. These analogues differ from TCR of the present invention in amino acid sequence or modifications that do not affect the sequence, or by both. Also included are analogues which include residues other than those naturally occurring L-amino acids (e.g., D-amino acids) or non-naturally occurring or synthetic amino acids (e.g., β- or γ-amino acids). It is understood that the polypeptides of the present invention are not limited to the representative polypeptides listed hereinabove.

Modifications (which do not normally alter the primary sequence) include in vivo or in vitro chemical derivation of polypeptides, e.g., acetylation, or carboxylation. Glycosylation is also included in modification, e.g., the polypeptides produced by glycosylation modification during its synthesis and processing or in the further processing steps. These modifications can be achieved by exposing the polypeptide to enzymes for glycosylation (e.g., mammalian glycosylating or deglycosylating enzymes). Also included are sequences that have phosphorylated amino acid residues, e.g., phosphotyrosine, phosphoserine, phosphothronine, as well as sequences that have been modified to improve their resistance to proteolytic degradation or to optimize solubility properties.

The polypeptides of the present invention can be used in a form of pharmaceutically or physiologically acceptable salt derived from acid or base. Such salts include, but are not limited to, the salts formed with the following acids: hydrochloric acid, hydrobromic acid, sulfuric acid, citric acid, tartaric acid, phosphoric acid, lactic acid, pyruvic acid, acetic acid, succinic acid, oxalic acid, fumaric acid, maleic acid, oxaloacetic acid, methanesulfonic acid, ethyl-sulfonic acid, benzene sulfonic acid, or isethionic acid. Also included are salts formed with alkali metals or alkaline earth metals (such as sodium, potassium, calcium or magnesium), and esters, carbamate or other conventional "prodrug" forms.

Polypeptides of the present invention can be provided in form of multivalent complexes. Multivalent TCR complex of the present invention comprises two, three, four or more TCR molecules linked with another molecule.

The present invention also relates to a polynucleotide encoding the TCR of the invention.

The full-length nucleotide sequence of the present invention, or a fragment thereof can usually be obtained by but not limited to the PCR amplification, recombination or synthetic methods. At present, the DNA sequences encoding polypeptides of the present invention (or fragments thereof, or derivatives thereof) can be obtained completely by chemical synthesis. Then the DNA sequences can be introduced into various existing DNA molecules (for example vectors) and cells known in the art.

The present invention also includes a vector containing the polynucleotide of the present invention, and a host cell genetically engineered by using the vector or the coding sequence of the present invention.

Encoding Sequence

The present invention further relates to polynucleotides encoding the TCR of the present invention, including polynucleotides encoding α chain and/or β chain of the TCR of the present invention.

The polynucleotides of the present invention can be in a form of DNA or RNA. DNA may be the coding strand or non-coding strand. For example, the coding sequence encoding the mature polypeptide can be identical with the coding sequence indicated in SEQ ID NO: 3, 4, 7, 8, 11, 12, 14, 16, 18, 21, 22 or 24, or can be a degenerate variant thereof. As used herein, "degenerate variant" refers to a nucleic acid sequence which encodes the protein having the amino acid sequence of SEQ ID NO: 1, 2, 5, 6, 9, 10, 13, 15, 17, 19, 20 or 23, while is different from the above corresponding coding sequence.

The full-length nucleotide sequence of the present invention, or a fragment thereof can usually be obtained by but not limited to the PCR amplification, recombination or synthetic methods. At present, the DNA sequences encoding polypeptides of the present invention (or fragments thereof, or derivatives thereof) can be obtained completely by chemical synthesis. Then the DNA sequences can be introduced into various existing DNA molecules (for example vectors) and cells known in the art.

The present invention also includes a vector containing the polynucleotide of the present invention, and a host cell engineered by the vector or the coding sequence of the present invention.

Preparation Method

The introduction of a Cys residue for forming an artificial interchain disulfide bond can be carried out by using any suitable methods including, but not limited to, those based on polymerase chain reaction (PCR), restriction enzyme based cloning or linkage independent cloning (LIC). These methods are detailed in many of the standard molecular biology texts. For further details regarding polymerase chain reaction (PCR) mutagenesis and restriction enzyme based cloning, see Sambrook & Russell, (2001) Molecular Cloning-A laboratory Manual ($3^{rd}$ Ed) CSHL press. More information on the procedure of LIC can be found in Rashtchian, (1995) Curr Opin Biotechnol 6 (1): 30-6.

The polypeptide of the present invention can be a recombinant or synthetic polypeptide. The polypeptide of the present invention can be a chemically synthesized or recombinant polypeptide. Accordingly, the polypeptide of the present invention can be artificially synthesized via a conventional method, or can be produced via a recombinant method.

With the conventional recombinant DNA technique, the polynucleotide of the present invention can be used to express or produce recombinant polypeptides of the present invention. Generally, the method comprises the following steps:

(1) Transforming or transfecting a suitable host cell with a polynucleotide or variant thereof encoding TCR polypeptide of the present invention or a recombinant expression vector containing said polynucleotide;

(2) Culturing the host cell in a suitable culture medium;

(3) Isolating and purifying the TCR polypeptide of the present invention from the culture medium or the cell.

Preferably, the soluble and stable TCR of the invention can be obtained by expressing it in bacteria such as in *E. coli* as an inclusion body and performing in vitro refolding.

Pharmaceutical Composition and Methods of Administration

The TCRs of the present invention and T cells transfected with TCRs of the present invention may be provided in a pharmaceutical composition together with a pharmaceutically acceptable carrier. The TCRs, multivalent TCR complexes and cells of the present invention will usually be supplied as part of sterile pharmaceutical composition which will normally comprises a pharmaceutically acceptable carrier. The pharmaceutical composition can be in any appropriate forms (depending upon the desired method of administering to a patient). It can be provided in unit dosage form, will generally be provided in a sealed container, and can be provided as part of a kit. The kit (although not necessarily) normally includes instructions for use. It may include a plurality of said unit dosage forms.

The TCRs of the present invention may be used alone, or be associated, preferably in a covalent manner with a conjugate. The conjugate comprises a detectable label, a therapeutic agent, a PK (protein kinase) modifying moiety, or a combination of any of the above.

Detectable markers for diagnostic purpose include, but are not limited to, fluorescent or luminescent labels, radio-labels, MRI (magnetic resonance imaging), or CT (computerized tomography) contrast agents, or enzymes capable of producing detectable products.

Therapeutic agents that can be associated with or coupled with the TCRs of the present invention include, but are not limited to: 1. Radioactive nuclide (Koppe, et al, 2005, *Cancer metastasis reviews* 24, 539); 2. Biological toxin (Chaudhary et al, 1989, Nature, 339, 394; Epel et al, 2002, *Cancer immunology and immunotherapy* 51, 565); 3. Cytokine (Gillies, et al, 1992, *PNAS*, 89, 1428; Card, et al, 2004, *Cancer immunology and immunotherapy* 53, 345; Halin, et al, 2003, *Cancer research* 63, 3202); 4. Antibody Fc fragment (Mosquera et al, 2005, *The journal of immunology* 174, 4381); 5. Antibody scFv (Zhu, et al, 1995, *International journal of cancer* 62, 319); 6. Gold nano-particle/nano-rod (Lapotko, et al, 2005, *Cancer letters* 239, 36; Huang, et al, 2006, *Journal of the American chemical society* 128, 2115); 7. Virus particles (Peng, et al, 2004, Gene therapy, 11, 1234); 8. Liposome (Mamot, et al, 2005, *Cancer research* 65, 11631); 9. Magnetic nano-particles; 10. Prodrug activating enzymes (such as DT-diaphorase (DTD) or Biphenyl hydrolase-like protein (BPHL)); 11. Chemotherapeutic agent (e.g., cisplatin), and the like.

The antibody or fragments thereof bound to (preferably, in a covalent manner) the TCR of the invention comprises an anti-T cell or an NK-cell determining antibody such as an anti-CD3 or anti-CD28 or anti-CD16 antibody, preferably anti-CD3 antibody. The binding of antibody or fragments thereof with TCR is capable of directing effector cells to better target a cell of interest.

The pharmaceutical composition can further comprise a pharmaceutically acceptable carrier. The term "pharmaceutically acceptable carrier" refers to a carrier for using in administering the therapeutic agents. The term refers to such medical carriers that they themselves do not induce antibody deleterious to the subject having been administered the composition, and they do not have excessive toxicity after administration. These carriers are well known by the skilled person in the art. The detailed discussion about the pharmaceutically acceptable excipient can be found in Remington's Pharmaceutical Sciences (Mack Pub. Co., N.J., 1991). Such carriers include, but are not limited to, saline, buffer solution, glucose, water, glycerin, ethanol, adjuvant or a combination thereof.

The pharmaceutically acceptable carrier in the therapeutic composition can comprise liquid, such as water, saline, glycerin, and ethanol. Further, these carriers can contain auxiliary substance(s), such as wetting agent or emulsifying agent, pH buffering substance, etc.

Typically, the therapeutic composition can be formulated into an injectable formulation, such as a liquid solution or suspension; or it may be in a solid form that is suitable to be formulated into a solution or suspension or liquid carrier before injection.

Once formulated, the composition of the present invention can be administered via conventional routes which include, but are not limited to, administering intra-ocularly, intramuscularly, intravenously, subcutaneously, intracutaneously or topically. The subject to be prevented or treated may be an animal, especially a human.

When the pharmaceutical composition of the present invention is used in the actual treatment, the dosage form of the pharmaceutical composition can be varied according to the uses. Preferably, as an example, the dosage form may include injection, oral formulation, etc.

The pharmaceutical composition can be formulated by mixing, diluting or dissolving according to the conventional methods. And, occasionally, suitable medical additives, such as excipients, disintegrating agents, adhesives, lubricants, diluting agents, buffering agents, isotonicities, preservatives, wetting agents, emulsifying agents, dispersing agents, stabilizing agents, and solubility promoters, may be added. Formulation can be carried out in a conventional manner according to the dosage form.

The pharmaceutical composition of the present invention can further be administered in a form of sustained release formulation. For example, the peptide of the present invention can be incorporated into the pill or microcapsule in which a sustained release polymer is used as carrier, and then the pill or microcapsule is implanted into the tissue to be treated by operation. Examples of the slow release polymer include ethylene-ethylene acetate copolymer, poly-hydroxymethylacrylate, polyacrylamide, polyvinylpyrrolidone, methyl cellulose, polymer of lactic acid, lactic acid-glycolic acid copolymer, etc. Preferable examples include the biodegradable polymers, such as polymer of lactic acid, and lactic acid-glycolic acid copolymer.

When the pharmaceutical composition of the present invention is used in the actual treatment, the dose of the peptide the present invention or a pharmaceutically acceptable salt thereof, as an active ingredient, can be suitably determined according to the body weight, age, sex, symptom of each patient.

Use of TCR of the Present Invention

The TCR of the present invention can be used as a drug or a diagnostic agent. The features which are suitable for use as a drug or a diagnostic agent can be obtained by modifications or other improvements. Such drugs or diagnostic agents may be used for treatment or diagnosis of various diseases, including but not limited to cancer (such as renal cancer, ovarian cancer, head and neck cancer, testicular cancer, lung cancer, gastric cancer, cervical cancer, bladder cancer, prostatic carcinomas or melanomas), autoimmune disease, viral infection disease, graft rejection and graft-versus-host disease.

Drug localization or targeted drug delivery can be realized based on specificity of the TCR of invention, thereby enhancing therapeutic or diagnostic effects of various diseases.

For cancer, the localization in the vicinity of tumors or metastasis can enhance the effect of toxins or immunostimulants. In autoimmune diseases, immunoreaction to normal cells or tissues can be inhibited specifically, or immunosuppressive drugs can be released slowly to get more local effect over a longer time-span while minimally affecting the overall immuno-capacity of the subject. In the prevention of transplant rejection, the effect of immunosuppression can be optimized in the same way. For viral diseases for which medicines exist, for example HIV, SIV, EBV, CMV, HCV, HBV, it is beneficial that the medicine is released or plays activation function in vicinity of infected cells.

TCRs of the invention can be used to modulate T cell activation by binding to specific pMHC and thereby inhibiting T cell activation. This approach may apply to autoimmune diseases involving T cell-mediated inflammation and/or tissue damage, for example type I diabetes.

TCRs of the invention can also be used for delivering cytotoxic agents to tumor cells, or can be transformed into T cells, thus rendering them a capability of damaging tumor cells presenting HLA complexes so that they can be administrated to a patient in a treatment process termed adoptive immunotherapy.

TCRs of invention can also be used as a therapeutic agent. TCRs of invention can be labeled with a detectable label, for example a label which is suitable for diagnostic purpose, for detecting binding of a MHC-peptide to a TCR of the invention which is specific for the MHC-peptide. A fluorescently-labeled multimeric TCR is suitable for use in FACS analysis to detect antigen presenting cells carrying a peptide to which the TCR is specific.

In addition, the soluble TCRs of the present invention can also bind with other molecules, preferably anti-CD3 antibodies to re-direct T cells, so that the T cells can target and kill target cells presenting specific antigens.

Industrial Applicability

The soluble and stable TCRs of the present invention are useful not only in the study of the interaction between TCR and pMHC (peptide-major histocompatibility complex) but also in diagnosis and treatment of diseases.

Main Advantages of the Present Invention Comprise:

(1) Soluble and stable T-Cell Receptor is obtained in the present invention, and the TCR of the present invention can be well renatured, refolded, and purified and can specifically bind to its original ligand.

(2) The T-Cell Receptor of the present invention has a higher Tm value.

(3) By using the T-Cell Receptor of the present invention, refolding yield of a protein can be increased, it is easy for large-scale production, and production cost can be reduced.

The present invention will be further illustrated below with reference to the specific examples. It should be understood that these examples are only to illustrate the invention, not to limit the scope of the invention. The experimental methods with no specific conditions described in the following examples are generally performed under the conventional conditions (e.g., the conditions described by Sambrook and Russell et al., Molecular Cloning-A Laboratory Manual (3$^{rd}$ Ed) CSHL Press), or according to the manufacture's instructions. Unless indicated otherwise, parts and percentage are calculated by weight. The experimental materials used in the examples of the invention are commercially available, unless indicated otherwise.

Example 1 Primers Design and PCR Mutations of 1G4 Molecule with a Formed Artificial Interchain Disulfide Bond at Position 46 of TRAV and Position 60 of TRBC1*01 or TRBC2*01 Exon 1

The amino acid at position 46 of TRAV of TCR molecule 1G4 (against antigen short peptide HLA-A2/SLLMWITQC (SEQ ID NO: 25), NY-ESO-1 tumor-specific antigen) was mutated into cysteine and the amino acid at position 60 of TRBC1*01 or TRBC2*01 exon 1 was mutated into cysteine, thereby forming an artificial interchain disulfide bond.

When the amino acid at position 46 of TRAV of the above TCR was mutated into cysteine, the primers were designed as follows:

```
5'-3'
                                       (SEQ ID NO: 26)
GTGGTTTCGTCAAGATTGCGGTAAAGGTCTGACC (SEQ ID NO: 27)
GGTCAGACCTTTACCGCAATCTTGACGAAACCAC
```

When the amino acid at position 60 of TRBC1*01 or TRBC2*01 exon 1 of the above TCR was mutated into cysteine, the primers were designed as follows:

```
5'-3'
                                       (SEQ ID NO: 28)
GGTGTTTCTACCGATTGCCAGCCGCTGAAAGAAC (SEQ ID NO: 29)
GTTCTTTCAGCGGCTGGCAATCGGTAGAAACACC
```

Steps for PCR were as follows:

The expression plasmid pET28a+ (Novagene) comprising 1G4 TCR α variable domain and β chain genes was mutated with the above primers for α chain variable domain and β chain genes, respectively. In each PCR site-directed mutation reaction, 10-30 ng of plasmid DNA was mixed with 5 μL of 10×KOD plus buffer, 5 μL of 2.5 mM dNTP Mix, 3 μL of 2 mM MgSO$_4$, 1 unit of KOD plus polymerase (Toyobo Shanghai BioScience Co., Ltd.), 1 μL of 10 μM upstream and downstream primers, and finally H$_2$O was added to 50 μL. After mixing, the reaction was carried out in a Bio-Rad PCR instrument. After initial denaturation (94° C. 2 min), 18 cycles of amplification (94° C. 15 sec of denaturation, 55° C. 30 sec of annealing and 68° C. 6 min of extension) were performed. And 10 units of Dpn I restriction enzyme (New England Biolabs) was used for digestion at 37° C. for 1 hour. 10 μL of digested product was transformed into competent E. coli DH5a bacteria and grown at 37° C. for 16 hours. Single clones were picked and cultured overnight in 5 mL LB+ Kanamycin. Plasmid DNA was purified using the Zyppy plasmid kit (ZYMO RESEARCH) according to the manufacturer's instructions and sent to Invitrogen for sequencing and the correct mutation was used for downstream expression.

The amino acid sequences of α chain variable domain and β chain extracellular domain of the three-domain TCR molecule 1G4 containing the artificial inter-chain disulfide bond of the present invention are shown in FIGS. 1a and 1b, respectively, and the corresponding nucleotide sequences are shown in FIGS. 2a and 2b. The introduced cysteine residues are shown in bold and underlined letters.

The target gene sequences of the above TCRα and β chains were synthesized and inserted into expression vector pET28a+(Novagene) by the standard method described in the "Molecular Cloning a Laboratory Manual" (Third Edition, Sambrook and Russell), and the upstream and downstream cloning sites were NcoI and NotI. The inserted fragment was confirmed by sequencing.

Example 2 Expression, Refolding and Purification and Determination Results of TCR Expression of TCR Protein Expression plasmids containing TCR α chain variable domain and β chain were transformed into E. coli strain BL21 (DE3), coated on LB plates (kanamycin 50 μg/ml) and incubated overnight at 37° C. overnight. The next day, the cells were picked and inoculated into 10 ml LB liquid medium (kanamycin 50 μg/ml) and cultured for 2-3 h and then seeded at 1:100 in volume to 1 L LB medium (kanamycin 50 μg/ml), and cultured to $OD_{600}$ at 0.5-0.8. And then the expression of the target protein was induced using IPTG at a final concentration of 1 mM. After 4 hours of induction, the cells were harvested by centrifugation at 6000 rpm for 10 min. The cells were washed once with PBS buffer and were dispensed. And the cells corresponding to 200 ml of bacterial culture were digested with 5 ml BugBuster Master Mix (Novagen) and the inclusion bodies were collected by centrifugation at 6000 g for 15 min. washing with detergent was then performed for 4 times to remove cell debris and membrane fractions. The inclusion bodies are then washed with a buffer such as PBS to remove the detergent and salt. Finally, the inclusion bodies were dissolved with 6M guanidine hydrochloride buffer solution. The inclusion body was determined for its concentration and dispensed at −80° C. for cryopreservation.

Refolding of TCR Protein

The inclusion body was taken out from the −80° C. cryogenic refrigerator and dithiothreitol (DTT) was added to a final concentration of 10 mM and the inclusion body was incubated at 37° C. for 30 min to 1 hour to ensure that the disulfide bond was fully open. The inclusion body sample solution (9.2 mg α chain and 10 mg β chain) was then added dropwise into 200 ml of 4° C. pre-cooled refolding buffer (100 mM Tris pH 8.1, 400 mM L-arginine, 2 mM EDTA, 5 M urea, 6.5 mM cysteamine hydrochloride and 1.87 mM dihydrochloride) and slowly stirred at 4° C. for about 30 minutes. The refolding solution was dialyzed with 8 volumes of pre-cooled $H_2O$ for 16-20 hours and then dialyzed twice with 8 volumes of 20 mM Tris pH 8.0 and dialyzed for 4 hours at 4° C. After dialysis, the sample was filtered and purified as follows.

The First Step of Purification for TCR Protein

The dialyzed refolded product (in 20 mM Tris pH 8.0) was eluted with a GE Hitrap Q anion exchange preparative column (GE Healthcare) using a gradient elution at 0-600 mM NaCl in an AKTA Purification Instrument (GE Healthcare). Each component was analyzed by Coomassie brilliant blue staining SDS-PAGE and then combined.

The Second Step of Purification for TCR Protein

The sample solution purified and pooled in the first step was concentrated for the purification in this step, and Superdex 100 160/300 GL gel filtration pre-packed column (GE Healthcare) pre-equilibrated in PBS buffer was used to purify the protein. The elution curves of three-domain TCR molecule obtained by introducing an artificial interchain disulfide bond of the present invention at position 46 of TRAV and position 60 of TRBC1*01 or TRBC2*01 exon 1 were shown in FIG. 3. Components with peak were analyzed by Coomassie bright blue-stained SDS-PAGE, and the reducing and non-reducing gel electrophoresis were shown in lane 1 and lane 6 of FIG. 65. According to the elution peak and the gel electrophoresis, it was found that the single elution peak was a soluble TCR molecule linked by an artificial interchain disulfide bond. The molecule formed a single band and was stable in SDS gel, and formed separate α chain variable domain and β chain after reduction.

Purity Determination of TCR Protein by HPLC

Figure 4:
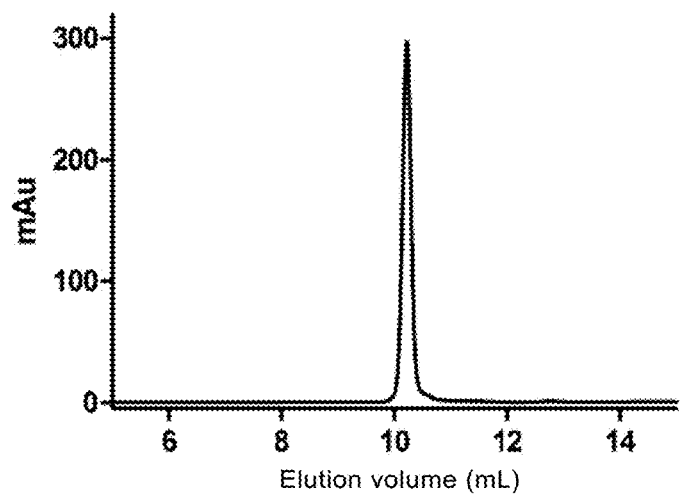
FIG. 4 shows a SEC spectrum of TCR α chain variable domain and β chain as shown in FIGS. 1a and 1b after refolding and protein purification.

The TCR protein was purified in two steps and pooled, and then the eluted fraction was tested for purity by HPLC. The condition was: Agilent 1260, column Bio SEC-3 (300 A, φ7.8×300 mm) with mobile phase of 150 mM phosphate buffer, flow rate 0.5 mL/min, column temperature 25° C., UV detection wavelength 214 nm. The SEC (spatial exclusion chromatography) spectrum of the TCR molecule is shown in FIG. 4. The HPLC elution peak of the TCR molecules containing the artificial interchain disulfide bonds of the present invention was single and symmetrical, indicating that the protein is stable in structure, there is no phenomenon, such as agglomeration or unfolding, and the purity of the protein is very high.

Calculation of Refolding Yield of TCR Protein

The refolding yield of TCR protein in the present invention is calculated as follows:

Protein refolding yield (%)=100*the amount of protein upon purification (mg)/the amount of inclusion body quantity used in refolding (mg). According to the above formula, the refolding yield of 1G4 TCR molecule forming an artificial interchain disulfide bond at position 46 of TRAV and position 60 of TRBC1*01 or TRBC2*01 exon 1 is 49%. Height yield indicates that the three-domain TCR molecule with the artificial interchain disulfide bond of the present invention at α chain variable region and β chain constant region of TCR is soluble and stable.

Figure 5:
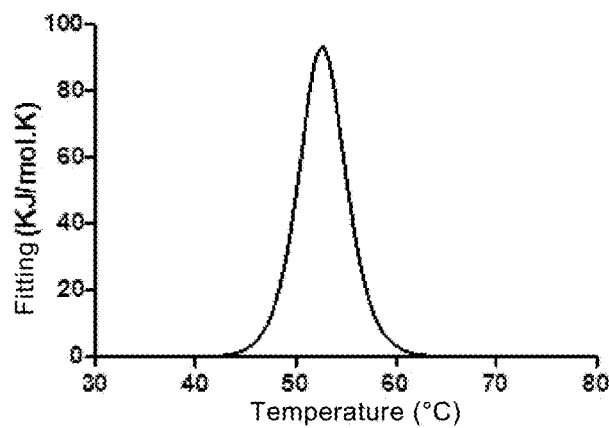
FIG. 5 shows a DSC thermogram of TCR α chain variable domain and β chain as shown in FIGS. 1a and 1b after refolding and protein purification.

Example 3 Stability Test for TCR Comprising Artificial Interchain Disulfide Bond at α Chain Variable Region and β Chain Constant Region of TCR 1 ml of 1G4 TCR protein (concentration 0.5 mg/ml) obtained in Example 2 was dialyzed against PBS and the thermostability of the TCR proteins was measured with differential scanning calorimeter (Nano DSC) of US TA company (Waters). Scanning range was 10-90° C., and heating rate was 1° C./min. Dialysis liquid PBS was used as a control, the baseline was measured for three times, and after the baseline was stable, the protein sample was examined. After collecting the data, the Tm value of the TCR was measured with the analysis software TA_DSC_NanoAnalyze and the DSC thermogram was obtained. The DSC thermogram of the TCR of the present invention comprising the artificial interchain disulfide bond at α chain variable region and β chain constant region was shown in FIG. 5 and its Tm value could reach 53° C. The thermogram could reflect that at room temperature, even at a temperature of 43-44° C., the TCR molecules comprising the artificial interchain disulfide bond of the present invention could maintain proper folding and maintain proper activity, indicating that their stability was very high.

Example 4 Binding Characterization and Specificity Detection

The binding activity of TCR protein to its corresponding antigen pMHC complex was examined using the forteBIO Oke real time analysis system.

A biotinylated pMHC complex of about 2 nm was immobilized on the surface of the SA sensor, and 0.05 mM biotin was flowed through the chip at a flow rate of 10 μL/min for 120s to block the remaining binding sites of streptavidin. The affinity of the TCR protein was determined by kinetic analysis using PBST buffer (PBS+0.005% Tween 20, pH 7.4) diluted to several different concentrations (typically 64, 32, 16, 8, 4, 0 uM). And the affinity for the corresponding pMHC was determined. The kinetic parameters were calculated using the evaluation software with a 1:1 model fit.

The preparation of the above pMHC complex was as follows:

a. Purification 100 ml of E. coli culture induced for heavy or light chains expression was collected and centrifuged at 8000 g for 10 min at 4° C. and the cells were washed once with 10 ml PBS and then the cells were resuspended vigorously with 5 ml BugBuster Master Mix Extraction Reagents (Merck) and incubated at room temperature for 20 min. After centrifugation at 4° C. 6000 g for 15 min, the supernatant was discarded and the inclusion bodies were collected.

The inclusion bodies were resuspended in 5 ml BugBuster Master Mix and incubated for 5 min at room temperature. 30 ml of BugBuster (10-fold dilution) was added and mixed, centrifuged at 4° C. 6000 g for 15 min. The supernatant was discarded and 30 ml BugBuster (10-fold dilution) was added to resuspend the inclusion body and mixed, and centrifuged at 4° C. 6000 g for 15 min, repeat twice. 30 ml 20 mM Tris-HCl pH 8.0 was added to resuspend the inclusion body, mixed and centrifuged at 4° C. 6000 g for 15 min. Finally, 20 mM Tris-HCl 8M urea was used to dissolve inclusion bodies. SDS-PAGE was used to detect the purity of inclusion body. A BCA kit was used to detect the concentration.

b. Refolding

The desired peptide was synthesized (Peking Parkson Gene Technology Co., Ltd.) and was dissolved in DMSO to a concentration of 20 mg/ml. Light chain and heavy chain inclusion bodies were dissolved with 8 M urea, 20 mM Tris pH 8.0, and 10 mM DTT. Before refolding, 3 M guanidine hydrochloride, 10 mM sodium acetate, and 10 mM EDTA were added for further denaturation. The short peptide at 25 mg/L (final concentration) was added to the refolding buffer (0.4 M L-arginine, 100 mM Tris pH 8.3, 2 mM EDTA, 0.5 mM oxidized glutathione, 5 mM reduced glutathione, 0.2 mM PMSF, and cooled to 4° C.), followed by the addition of 20 mg/L light chain and 90 mg/L heavy chain (final concentration, heavy chain was added three times, 8 h every time) refolding at 4° C. for at least 3 days to complete, and SDS-PAGE was used to detect the success of refolding.

c. Purification after Refolding

The refolding buffer was replaced with dialysis using 10 volumes of 20 mM Tris pH 8.0 and the refolding buffer was replaced at least twice to sufficiently reduce the ionic strength of the solution. After dialysis, the protein solution was filtered through a 0.45 um cellulose acetate filter and then loaded onto HiTrap Q HP (GE Universal) anion exchange column (5 ml bed volume). The protein was eluted with a linear gradient of 0-400 mM NaCl prepared at 20 mM Tris pH 8.0 using a Akta Purification Instrument (GE General Electric Co., Ltd.), and pMHC was eluted at about 250 mM NaCl and the peak components were collected and the purity was analyzed by SDS-PAGE.

d. Biotinylation

The purified pMHC molecule was concentrated by Millipore ultrafiltration tubes while the buffer was replaced with 20 mM Tris pH 8.0 followed by adding biotinylated reagent 0.05 M Bicine pH 8.3, 10 mM ATP, 10 mM MgOAc, 50 μM D-Biotin, 100 μg/ml BirA enzyme (GST-BirA). The mixture was incubated at room temperature overnight. SDS-PAGE was used to determine whether biotinylation was complete.

e. Purification of Biotinylated Complexes

The biotin labeled pMHC molecule was concentrated to 1 ml with a Millipore ultrafiltration tube, and the biotinylated pMHC was purified by gel filtration chromatography using an Akta Purification Instrument (GE General Electric Co., Ltd.). HiPrep™ 16/60 S200 HR column (GE General Electric) was pre-equilibrated with filtered PBS. 1 ml of concentrated biotinylated pMHC molecule was loaded and then eluted with PBS at a flow rate of 1 ml/min. The biotinylated pMHC molecule appeared as a single peak at about 55 ml. The protein-containing fractions were pooled, and concentrated with Millipore ultrafiltration tubes. The protein concentration was measured by BCA method (Thermo), and the biotinylated pMHC molecules were stored at −80° C. by adding a protease inhibitor cocktail (Roche).

The binding curves of the different concentrations of 1G4 TCR molecules comprising the artificial interchain disulfide bond of the present invention to their corresponding antigens were shown in FIG. 6. It can be seen from these binding curves that the decrease in concentration did not affect the binding of the TCR molecules of the present invention to their corresponding antigens. The TCR molecules at a low concentration exhibited the same binding time as that at a high concentration, which also demonstrated from another aspect that the TCR comprising the artificial interchain disulfide bond of the present invention was relatively stable.

Detection of Specificity of TCR Protein forteBIO Oke real-time analysis system was used to detect the specificity of the TCR protein to its corresponding antigen pMHC complex. The specificity of the TCR protein comprising the artificial interchain disulfide bond of the present invention was detected as follows: the corresponding antigen pMHC complex (biotinylated) of the TCR and selected several other unrelated antigen pMHC complexes (biotinylated) were loaded onto the surface of SA sensor, respectively; then interacted with each of the TCR proteins to be tested; and finally, the signals generated by the interaction were analyzed. According to the above detection method, 1G4 TCR comprising the artificial interchain disulfide bond of the present invention was only bound to its corresponding antigen pMHC complex, and did not interact with other unrelated antigens Example 5 Three-Domain TCR Molecule with an Formed Artificial Interchain Disulfide Bond Between Position 46 of TRAV and Position 60 of TRBC1*01 or TRBC2*01 Exon 1

In this example, it was further demonstrated that it is possible to obtain a soluble and stable three-domain TCR molecule after an artificial interchain disulfide bond was formed at position 46 of TRAV of the TCR molecule and position 60 of TRBC1*01 or TRBC2*01 exon 1.

The amino acids at position 46 of TRAV of TCR molecule JM22 (against antigen short peptide HLA-A2/GILGFVFTL (SEQ ID NO: 30), derived from influenza virus matrix protein) and LC13 (against antigen short peptide HLA-B4405: EEYLKAWTF (SEQ ID NO: 31)) were mutated into cysteine and the amino acid at position 60 of TRBC1*01 or TRBC2*01 exon 1 was mutated into cysteine, thereby forming an artificial interchain disulfide bond.

When the amino acid at position 46 of TRAV of the above JM22 TCR was mutated into cysteine, the primers were designed as follows:

```
                                         5'-3'
                                                              (SEQ ID NO: 32)
            GTGGTATCGTCAAGAATGCGGTGAAGGTCCGGTC (SEQ ID NO: 33)
            GACCGGACCTTCACCGCATTCTTGACGATACCAC
```

When the amino acid at position 60 of TRBC1*01 or TRBC2*01 exon 1 of the above JM22 TCR was mutated into cysteine, the primers were designed as follows:

```
                                         5'-3'
                                                              (SEQ ID NO: 34)
            GGTGTTTCTACCGATTGCCAGCCGCTGAAAGAAC (SEQ ID NO: 35)
            GTTCTTTCAGCGGCTGGCAATCGGTAGAAACACC
```

When the amino acid at position 46 of TRAV of the above LC13 TCR was mutated into cysteine, the primers were designed as follows:

```
                                         5'-3'
                                                              (SEQ ID NO: 36)
            CATTGGTACCGTCAGCTGTGCAGCCAAGGTCCGG (SEQ ID NO: 37)
            CCGGACCTTGGCTGCACAGCTGACGGTACCAATG
```

When the amino acid at position 60 of TRBC1*01 or TRBC2*01 exon 1 of the above LC13 TCR was mutated into cysteine, the primers were designed as follows:

```
                                         5'-3'
                                                              (SEQ ID NO: 38)
            GGTGTTTCTACCGATTGCCAGCCGCTGAAAGAAC (SEQ ID NO: 39)
            GTTCTTTCAGCGGCTGGCAATCGGTAGAAACACC
```

The PCR, refolding and performance tests of the TCRs were performed according to the methods described in Examples 1 to 4.

Figure 10:
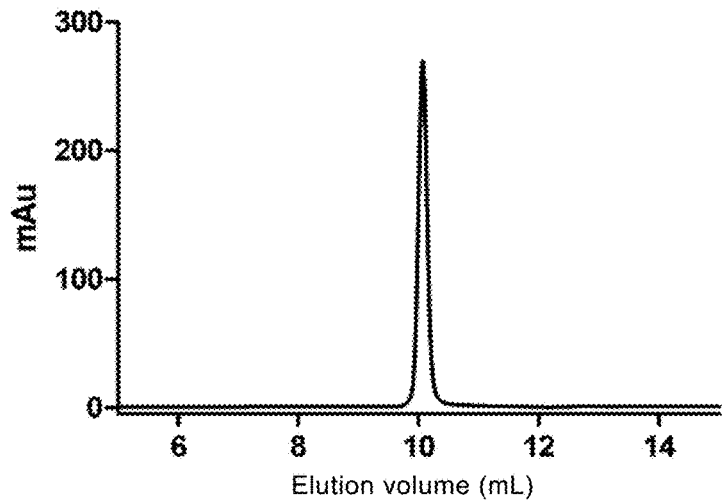
FIG. 10 shows a SEC spectrum of TCR α chain variable domain and β chain as shown in FIGS. 7a and 7b after refolding and protein purification.
Figure 11:
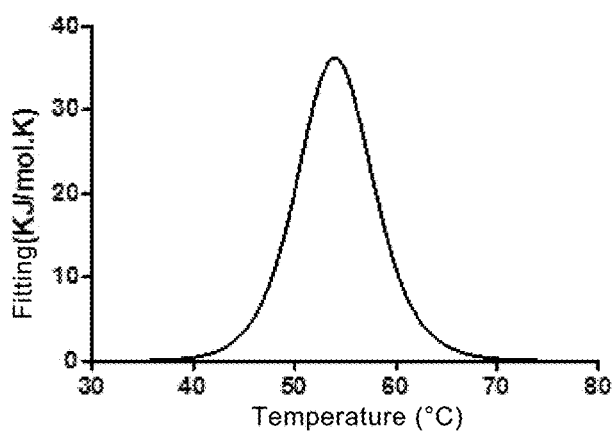
FIG. 11 shows a DSC thermogram of TCR α chain variable domain and β chain as shown in FIGS. 7a and 7b after refolding and protein purification.
Figure 12:
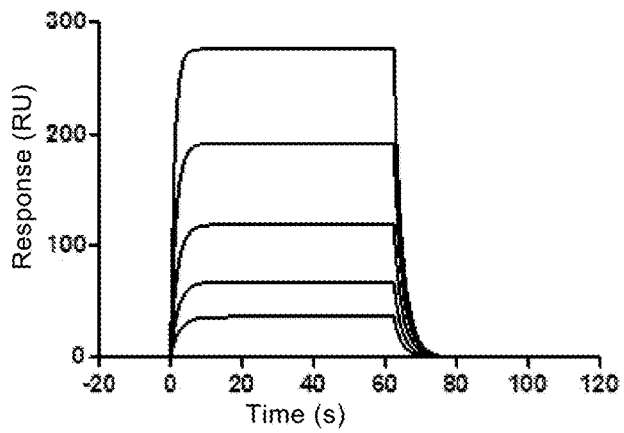
FIG. 12 shows binding curves of JM22TCR molecule obtained from TCR α chain variable domain and β chain as shown in FIGS. 7a and 7b at different concentrations with its corresponding antigen, after refolding and protein purification.
Figure 66:
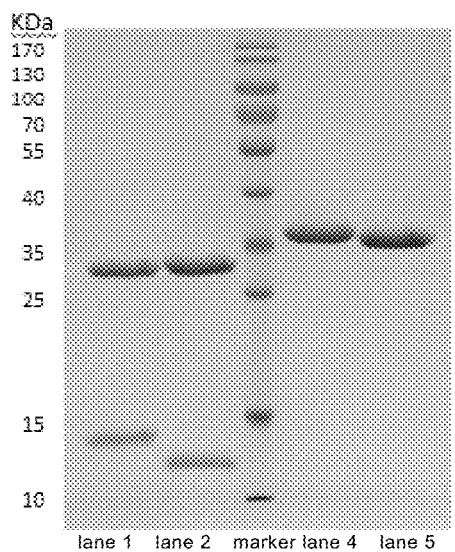
FIG. 66 shows gel electrophoresis of three-domain soluble protein containing an artificial interchain disulfide bond at different positions between α chain variable domain and chain constant domain of different TCR molecules.

The amino acid sequences of α chain variable domain and β chain extracellular domain of the three-domain TCR molecule JM22 containing the artificial inter-chain disulfide bond of the present invention are shown in FIGS. 7a and 7b, respectively, and the corresponding nucleotide sequences are shown in FIGS. 8a and 8b. The introduced cysteine residues are shown in bold and underlined letters. The elution curve and the gel pattern were shown in lane 2 (reduced gel) and lane 5 (non-reducing gel) of FIGS. 9 and 66, respectively. The single and symmetrical HPLC elution peak was shown in FIG. 10. The refolding yield of protein reached 25%, the Tm value was 54° C. and the corresponding DSC spectrum is shown in FIG. 11. The binding curve of JM22 molecule to its corresponding antigen is shown in FIG. 12.

Figure 15:
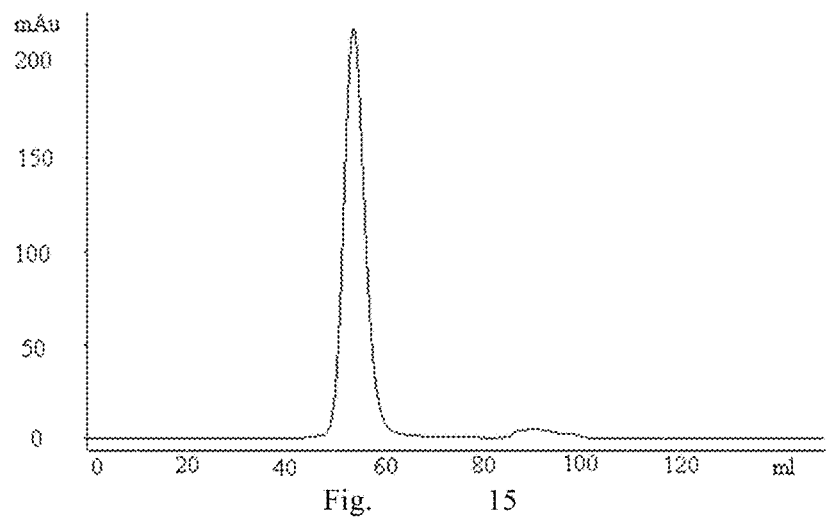
FIG. 15 shows an elution curve of gel filtration column of TCR α chain variable domain and β chain as shown in FIGS. 13a and 13b after refolding.
Figure 16:
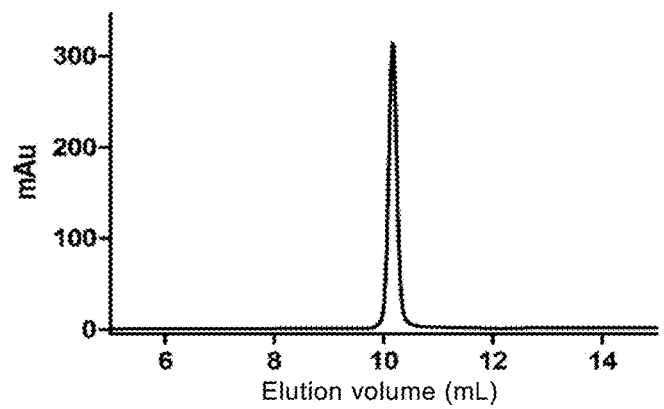
FIG. 16 shows a SEC spectrum of TCR α chain variable domain and β chain as shown in FIGS. 13a and 13b after refolding and protein purification.
Figure 17:
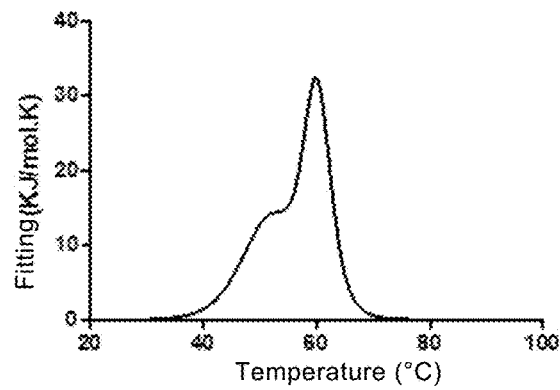
FIG. 17 shows a DSC thermogram of TCR α chain variable domain and β chain as shown in FIGS. 13a and 13b after refolding and protein purification.

The amino acid sequences of α chain variable domain and β chain extracellular domain of the three-domain TCR molecule LC13 of the present invention comprising the artificial inter-chain disulfide bond are shown in FIGS. 13a and 13b, respectively, and the corresponding nucleotide sequences are shown in FIGS. 14a and 14b. The introduced cysteine residues are shown in bold and underlined letters. The elution curve and the gel pattern were shown in lane 1 (reduced gel) and lane 4 (non-reducing gel) of FIGS. 15 and 66, respectively. The single and symmetrical HPLC elution peak was shown in FIG. 16. The refolding yield of protein was quite high (21%), the Tm value was 60° C. and the corresponding DSC spectrum is shown in FIG. 17. The binding curve of LC13 molecule to its corresponding antigen is shown in FIG. 18.

According to the elution curves and the SDS gel electrophoresis for the above molecules, it was found that the eluted peak component was the soluble TCR molecule linked by an artificial interchain disulfide bond of the present invention, which formed a single band and was stable in SDS gel, and formed separate α chain variable domain and β chain after reduction. The refolding yield of protein is relatively high. Additionally, Tm value of the TCR molecule linked by an artificial interchain disulfide bond of the present invention is high, indicating that the molecule can correctly fold at higher temperature, maintain proper activity, and thus possess high stability. Meanwhile, it can be seen from the binding curves for TCR molecules binding to their original ligands that the decrease in concentration of TCR did not affect the binding of the TCR molecules to their corresponding antigens, which also demonstrated from another aspect that the TCR comprising the interchain disulfide bond of the present invention was stable. In the specificity test, the TCR molecules of the present invention with introduced artificial interchain disulfide bonds only bind to their respective antigens and do not interact with several other unrelated antigens and thus exhibit good specificity. Therefore, the above experimental data demonstrate that a soluble and stable three-domain TCR protein of the present invention can be obtained by introducing an artificial interchain disulfide bond between position 46 of TRAV and position 60 of TRBC1*01 or TRBC2*01 exon 1.

Example 6 Four-Domain TCR Molecule with an Formed Artificial Interchain Disulfide Bond Between Position 46 of TRAV and Position 60 of TRBC1*01 or TRBC2*01 Exon 1

In this example, it was demonstrated that it is possible to obtain a soluble and stable four-domain TCR molecule after an artificial interchain disulfide bond was formed at position 46 of TRAV of the TCR molecule and position 60 of TRBC1*01 or TRBC2*01 exon 1.

The amino acids at position 46 of TRAV of TCR molecule 1G4 (against antigen short peptide HLA-A2/SLLMWITQC, NY-ESO-1 tumor-specific antigen), JM22 (against antigen short peptide HLA-A2/GILGFVFTL, derived from influenza virus matrix protein) and LC13 (against antigen short peptide HLA-B4405: EEYLKAWTF) were mutated into cysteine and the amino acid at position 60 of TRBC1*01 or TRBC2*01 exon 1 was mutated into cysteine, thereby forming an artificial interchain disulfide bond. Used primers and steps for mutation can be found in the above Examples.

The PCR, refolding and performance tests of the TCRs were performed according to the methods described in Examples 1 to 4, except that in the refolding step of TCR in Example 2, the amount of inclusion body of TCR α chain and β chain was 15 mg and 10 mg, respectively.

Figure 21:
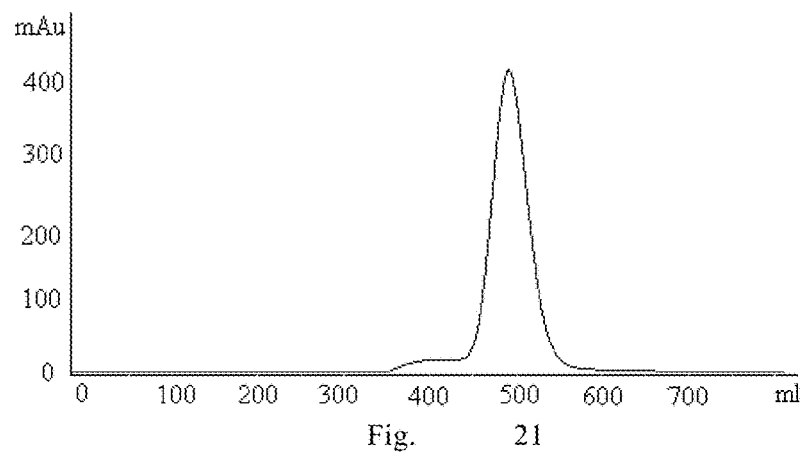
FIG. 21 shows an elution curve of gel filtration column of α chain and β chain of four-domain 1G4TCR after refolding, wherein an artificial interchain disulfide bond is formed at position 46 of TRAV and position 60 of TRBC1*01 or TRBC2*01 exon 1.
Figure 22:
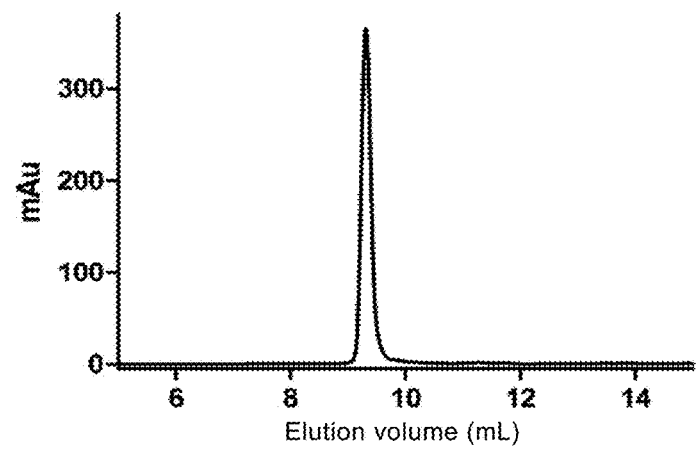
FIG. 22 shows a SEC spectrum of α chain and β chain of four-domain 1G4TCR after refolding and protein purification, wherein an artificial interchain disulfide bond is formed at position 46 of TRAV and position 60 of TRBC1*01 or TRBC2*01 exon 1.
Figure 23:
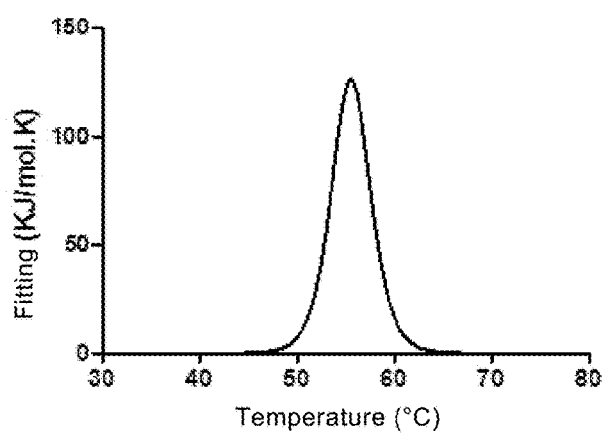
FIG. 23 shows a DSC thermogram of α chain and 13 chain of four-domain 1G4TCR after refolding and protein purification, wherein an artificial interchain disulfide bond is formed at position 46 of TRAV and position 60 of TRBC1*01 or TRBC2*01 exon 1.

The amino acid sequences of α chain and β chain extracellular domain of the four-domain TCR molecule 1G4 of the present invention containing the artificial inter-chain disulfide bond are shown in FIGS. 19 and 1b, respectively, and the corresponding nucleotide sequences are shown in FIGS. 20 and 2b. The introduced cysteine residues are shown in bold and underlined letters. The elution curve and the gel pattern were shown in lane 1 (reduced gel) and lane 6 (non-reducing gel) of FIGS. 21 and 67, respectively. The single and symmetrical HPLC elution peak was shown in FIG. 22. The refolding yield of protein reached 35%, the Tm value was 56° C. and the corresponding DSC spectrum is shown in FIG. 23. The binding curve of 1G4 molecule to its corresponding antigen is shown in FIG. 24.

Figure 27:
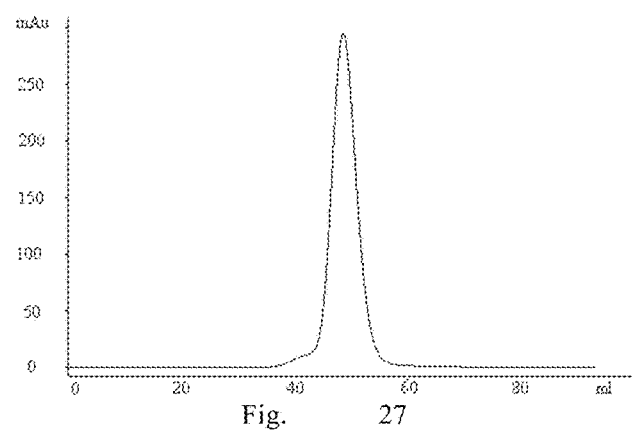
FIG. 27 shows an elution curve of gel filtration column of α chain and chain of four-domain JM22TCR after refolding, wherein an artificial interchain disulfide bond is formed at position 46 of TRAV and position 60 of TRBC1*01 or TRBC2*01 exon 1.
Figure 28:
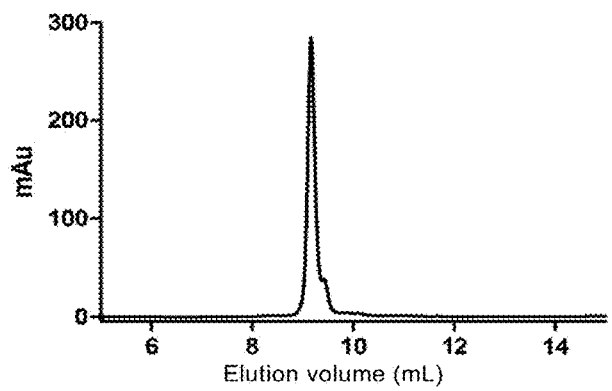
FIG. 28 shows a SEC spectrum of α chain and β chain of four-domain JM22TCR after refolding and protein purification, wherein an artificial interchain disulfide bond is formed at position 46 of TRAV and position 60 of TRBC1*01 or TRBC2*01 exon 1.
Figure 29:
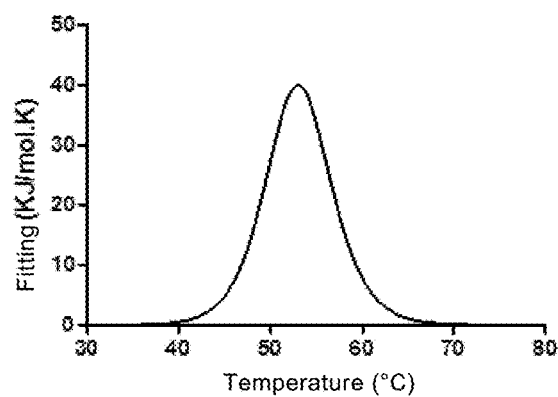
FIG. 29 shows a DSC thermogram of α chain and β chain of four-domain JM22TCR after refolding and protein purification, wherein an artificial interchain disulfide bond is formed at position 46 of TRAV and position 60 of TRBC1*01 or TRBC2*01 exon 1.
Figure 68:
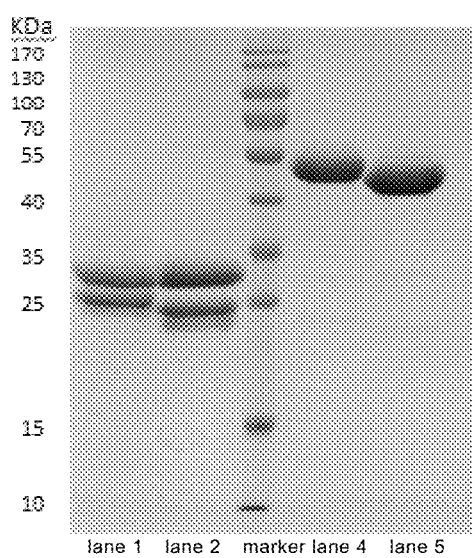
FIG. 68 shows gel electrophoresis of four-domain soluble protein containing an artificial interchain disulfide bond at different positions between α chain variable domain and chain constant domain of different TCR molecules.

The amino acid sequences of α chain and β chain extracellular domain of the four-domain TCR molecule JM22 of the present invention containing the artificial inter-chain disulfide bond are shown in FIGS. 25 and 7b, respectively, and the corresponding nucleotide sequences are shown in FIGS. 26 and 8b. The introduced cysteine residues are shown in bold and underlined letters. The elution curve and the gel pattern were shown in lane 2 (reduced gel) and lane 5 (non-reducing gel) of FIGS. 27 and 68, respectively. The single and symmetrical HPLC elution peak was shown in FIG. 28. The refolding yield of protein reached 20%, the Tm value was 53° C. and the corresponding DSC spectrum is shown in FIG. 29. The binding curve of JM22 molecule to its corresponding antigen is shown in FIG. 30.

The amino acid sequences of α chain variable domain and β chain extracellular domain of the four-domain TCR molecule LC13 of the present invention containing the artificial inter-chain disulfide bond are shown in FIGS. 31 and 13b, respectively, and the corresponding nucleotide sequences are shown in FIGS. 32 and 14b. The introduced cysteine residues are shown in bold and underlined letters. The elution curve and the gel pattern were shown in lane 1 (reduced gel) and lane 4 (non-reducing gel) of FIGS. 33 and 68, respectively. The single and symmetrical HPLC elution peak was shown in FIG. 34. The refolding yield of protein was quite high (22%), and the Tm value was 60° C. The binding curve of LC13 molecule to its corresponding antigen is shown in FIG. 36.

According to the elution curves and the SDS gel electrophoresis for the above molecules, it was found that the eluted peak component was the soluble four-domain TCR molecule linked by an artificial interchain disulfide bond of the present invention, which formed a single band and was stable in SDS gel, and formed separate α chain variable domain and β chain after reduction. The refolding yield of protein is relatively high. Additionally, Tm value of the TCR molecule linked by an artificial interchain disulfide bond of the present invention is high, indicating that the molecule can correctly fold at higher temperature, maintain proper activity, and thus possess high stability. Meanwhile, it can be seen from the binding curves for TCR molecules binding to their original ligands that the decrease in concentration of TCR did not affect the binding of the TCR molecules to their corresponding antigens, which also demonstrated from another aspect that the TCR comprising the interchain disulfide bond of the present invention was stable. In the specificity test, the TCR molecules of the present invention with introduced artificial interchain disulfide bonds only bind to their respective antigens and do not interact with several other unrelated antigens and thus exhibit good specificity. Therefore, the above experimental data demonstrate that a soluble and stable four-domain TCR protein of the present invention can be obtained by introducing an artificial interchain disulfide bond between position 46 of TRAV and position 60 of TRBC1*01 or TRBC2*01 exon 1.

Example 7 Three-Domain TCR Molecule with an Formed Artificial Interchain Disulfide Bond Between Position 47 of TRAV and Position 61 of TRBC1*01 or TRBC2*01 Exon 1

In this example, it was demonstrated that it is possible to obtain a soluble and stable three-domain TCR molecule after an artificial interchain disulfide bond was formed at position 47 of TRAV of the TCR molecule and position 61 of TRBC1*01 or TRBC2*01 exon 1.

The amino acid at position 47 of TRAV of 1G4 TCR molecule was mutated into cysteine and the amino acid at position 61 of TRBC1*01 or TRBC2*01 exon 1 was mutated into cysteine, thereby forming an artificial inter-chain disulfide bond.

When the amino acid at position 47 of TRAV of the above TCR was mutated into cysteine, the primers were designed as follows:

```
5'-3'
                                    (SEQ ID NO: 40)
GTTTCGTCAAGATCCGTGCAAAGGTCTGACCAGC (SEQ ID NO: 41)
GCTGGTCAGACCTTTGCACGGATCTTGACGAAAC
```

When the amino acid at position 61 of TRBC1*01 or TRBC2*01 exon 1 of the above TCR was mutated into cysteine, the primers were designed as follows:

```
5'-3'
                                    (SEQ ID NO: 42)
GTTTCTACCGATCCGtgcCCGCTGAAAGAACAG (SEQ ID NO: 43)
CTGTTCTTTCAGCGGgcaCGGATCGGTAGAAAC
```

The PCR, refolding and performance tests of the TCRs were performed according to the methods described in Examples 1 to 4.

The amino acid sequences of α chain variable domain and β chain extracellular domain of the three-domain TCR molecule of the present invention containing the artificial inter-chain disulfide bond are shown in FIGS. 37a and 37b, respectively, and the corresponding nucleotide sequences are shown in FIGS. 38a and 38b. The introduced cysteine residues are shown in bold and underlined letters. The elution curve and the gel pattern were shown in lane 4 (reduced gel) and lane 9 (non-reducing gel) of FIGS. 39 and 65, respectively. The single and symmetrical HPLC elution peak was shown in FIG. 40. The refolding yield of protein reached 36%, the Tm value was 52° C. and the corresponding DSC spectrum is shown in FIG. 41. The binding curve of the TCR molecule to its corresponding antigen is shown in FIG. 42.

According to the above elution curves and the SDS gel electrophoresis, it was found that the eluted peak component was the soluble three-domain TCR molecule linked by an artificial interchain disulfide bond of the present invention, which formed a single band and was stable in SDS gel, and formed separate α chain variable domain and β chain after reduction. The refolding yield of protein is relatively high. Additionally, Tm value of the TCR molecule linked by an artificial interchain disulfide bond of the present invention is high, indicating that the molecule can correctly fold at higher temperature, maintain proper activity, and thus possess high stability. Meanwhile, it can be seen from the binding curves for TCR molecules binding to their original ligands that the decrease in concentration of TCR did not affect the binding of the TCR molecules to their corresponding antigens, which also demonstrated from another aspect that the TCR comprising the interchain disulfide bond of the present invention was stable. In the specificity test, the TCR molecules of the present invention with introduced artificial interchain disulfide bonds only bind to their respective antigens and do not interact with several other unrelated antigens and thus exhibit good specificity. Therefore, the above experimental data demonstrate that a soluble and stable three-domain TCR protein of the present invention can be obtained by introducing an artificial interchain disulfide bond between position 47 of TRAV and position 61 of TRBC1*01 or TRBC2*01 exon 1.

Example 8 Four-Domain TCR Molecule with an Formed Artificial Interchain Disulfide Bond Between Position 47 of TRAV and Position 61 of TRBC1*01 or TRBC2*01 Exon 1

In this example, it was demonstrated that it is possible to obtain a soluble and stable four-domain TCR molecule after an artificial interchain disulfide bond was formed at position 47 of TRAV of the TCR molecule and position 61 of TRBC1*01 or TRBC2*01 exon 1.

The amino acid at position 47 of TRAV of TCR molecule was mutated into cysteine and the amino acid at position 61 of TRBC1*01 or TRBC2*01 exon 1 was mutated into cysteine, thereby forming an artificial interchain disulfide bond. Used primers and steps for mutation can be found in the above Examples.

The PCR, refolding and performance tests of the TCRs were performed according to the methods described in Examples 1 to 4, except that in the refolding step of TCR in Example 2, the amount of inclusion body of TCR α chain and β chain was 15 mg and 10 mg, respectively.

Figure 47:
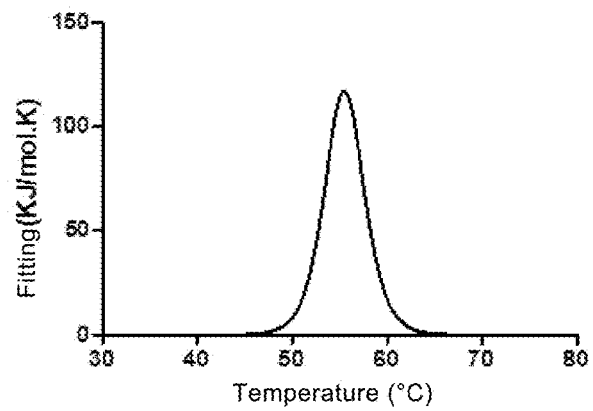
FIG. 47 shows a DSC thermogram of α chain and β chain of four-domain TCR after refolding and protein purification, wherein an artificial interchain disulfide bond is formed at position 47 of TRAV and position 61 of TRBC1*01 or TRBC2*01 exon 1.
Figure 48:
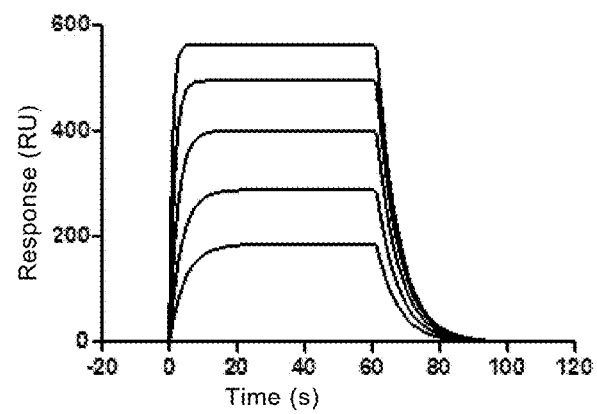
FIG. 48 shows binding curves of TCR molecule at different concentrations with its corresponding antigen, wherein the molecule is obtained from α chain and 13 chain of four-domain TCR after refolding and protein purification, and an artificial interchain disulfide bond is formed at position 47 of TRAV and position 61 of TRBC1*01 or TRBC2*01 exon 1.

The amino acid sequences of α chain and β chain extracellular domain of the four-domain TCR molecule of the present invention containing the artificial inter-chain disulfide bond are shown in FIGS. 43 and 37b, respectively, and the corresponding nucleotide sequences are shown in FIGS. 44 and 38b. The introduced cysteine residues are shown in bold and underlined letters. The elution curve and the gel pattern were shown in lane 4 (reduced gel) and lane 9 (non-reducing gel) of FIGS. 45 and 67, respectively. The single and symmetrical HPLC elution peak was shown in FIG. 46. The refolding yield of protein reached 43%, the Tm value was 56° C. and the corresponding DSC spectrum is shown in FIG. 47. The binding curve of the TCR molecule to its corresponding antigen is shown in FIG. 48.

According to the above elution curves and the SDS gel electrophoresis, it was found that the eluted peak component was the soluble four-domain TCR molecule linked by an artificial interchain disulfide bond of the present invention, which formed a single band and was stable in SDS gel, and formed separate α chain and β chain after reduction. The refolding yield of protein is relatively high. Additionally, Tm value of the TCR molecule linked by an artificial interchain disulfide bond of the present invention is high, indicating that the molecule can correctly fold at higher temperature, maintain proper activity, and thus possess high stability. Meanwhile, it can be seen from the binding curves for TCR molecules binding to their original ligands that the decrease in concentration of TCR did not affect the binding of the TCR molecules to their corresponding antigens, which also demonstrated from another aspect that the TCR comprising the interchain disulfide bond of the present invention was stable. In the specificity test, the TCR molecules of the present invention with introduced artificial interchain disulfide bonds only bind to their respective antigens and do not interact with several other unrelated antigens and thus exhibit good specificity. Therefore, the above experimental data demonstrate that a soluble and stable four-domain TCR protein of the present invention can be obtained by introducing an artificial interchain disulfide bond between position 47 of TRAV and position 61 of TRBC1*01 or TRBC2*01 exon 1.

Example 9 Three-Domain TCR Molecule with an Formed Artificial Interchain Disulfide Bond Between Position 46 of TRAV and Position 61 of TRBC1*01 or TRBC2*01 Exon 1

In this example, it was demonstrated that it is possible to obtain a soluble and stable three-domain TCR molecule after an artificial interchain disulfide bond was formed at position 46 of TRAV of the TCR molecule and position 61 of TRBC1*01 or TRBC2*01 exon 1.

The amino acid at position 46 of TRAV of 1G4 TCR molecule was mutated into cysteine and the amino acid at position 61 of TRBC1*01 or TRBC2*01 exon 1 was mutated into cysteine, thereby forming an artificial interchain disulfide bond. Used primers and steps for mutation can be found in the above Examples.

The PCR, refolding and performance tests of the TCRs were performed according to the methods described in Examples 1 to 4.

Figure 49:
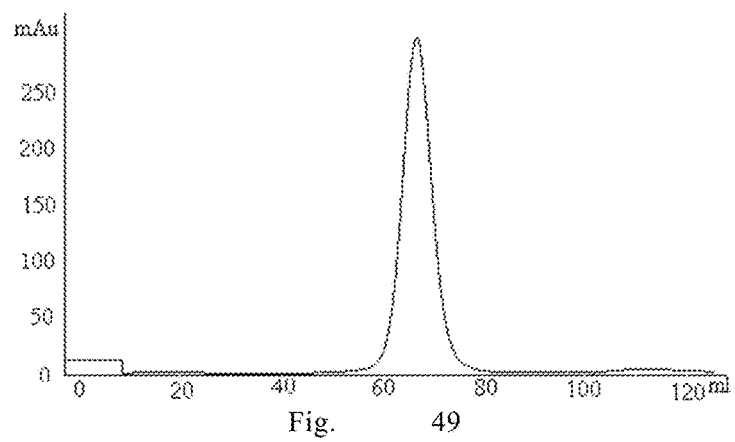
FIG. 49 shows an elution curve of gel filtration column of α chain and chain of three-domain TCR after refolding, wherein an artificial interchain disulfide bond is formed at position 46 of TRAV and position 61 of TRBC1*01 or TRBC2*01 exon 1.
Figure 50:
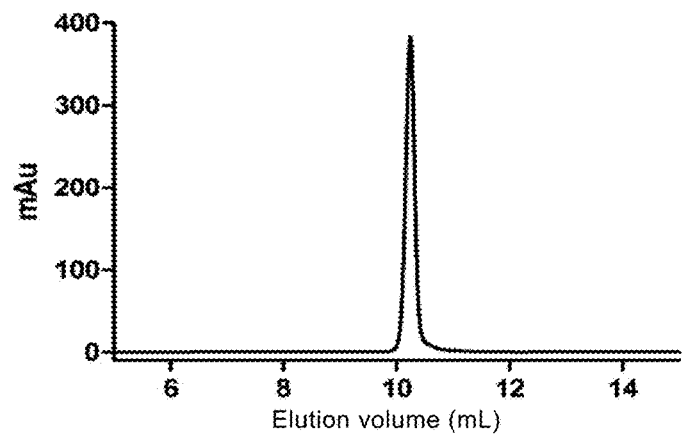
FIG. 50 shows a SEC spectrum of α chain and chain of three-domain TCR after refolding and protein purification, wherein an artificial interchain disulfide bond is formed at position 46 of TRAV and position 61 of TRBC1*01 or TRBC2*01 exon 1.
Figure 51:
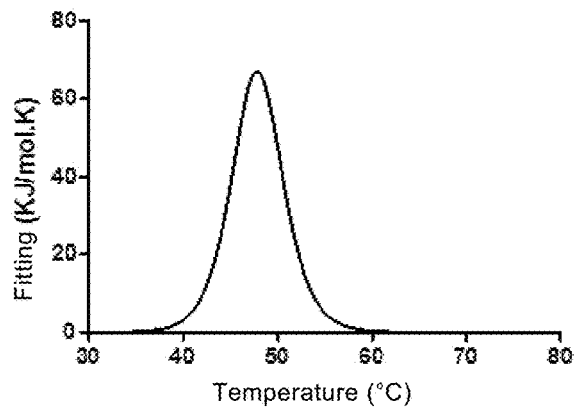
FIG. 51 shows a DSC thermogram of α chain and chain of three-domain TCR after refolding and protein purification, wherein an artificial interchain disulfide bond is formed at position 46 of TRAV and position 61 of TRBC1*01 or TRBC2*01 exon 1.
Figure 52:
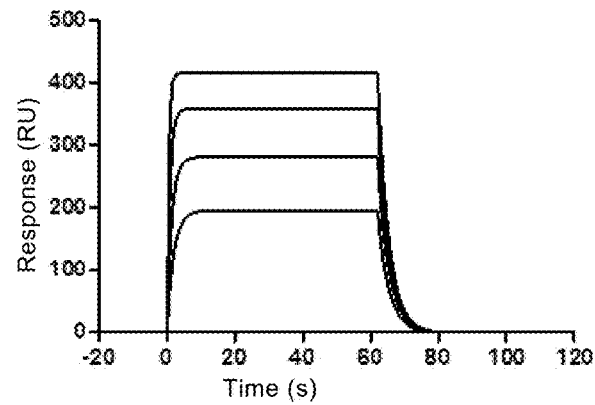
FIG. 52 shows binding curves of TCR molecule at different concentrations with its corresponding antigen, wherein the molecule is obtained from α chain and 13 chain of three-domain TCR after refolding and protein purification, and an artificial interchain disulfide bond is formed at position 46 of TRAV and position 61 of TRBC1*01 or TRBC2*01 exon 1.
Figure 65:
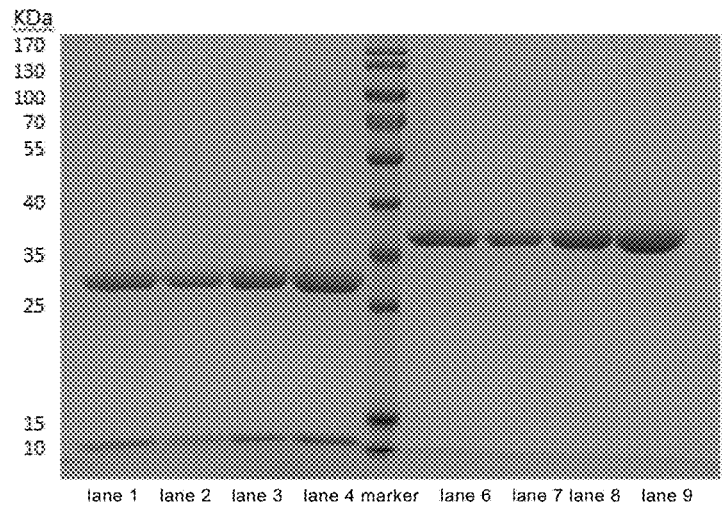
FIG. 65 shows gel electrophoresis of three-domain soluble protein containing an artificial interchain disulfide bond at different positions between α chain variable domain and chain constant domain of 1G4 TCR molecule.

The elution curve and the gel pattern of the three-domain TCR molecule of the present invention containing the artificial inter-chain disulfide bond were shown in lane 2 (reduced gel) and lane 7 (non-reducing gel) of FIGS. 49 and 65, respectively. The single and symmetrical HPLC elution peak was shown in FIG. 50. The refolding yield of protein reached 37%, the Tm value was 48° C. and the corresponding DSC spectrum is shown in FIG. 51. The binding curve of the TCR molecule to its corresponding antigen is shown in FIG. 52.

According to the above elution curves and the SDS gel electrophoresis, it was found that the eluted peak component was the soluble three-domain TCR molecule linked by an artificial interchain disulfide bond of the present invention, which formed a single band and was stable in SDS gel, and formed separate α chain variable domain and β chain after reduction. The refolding yield of protein is relatively high. Additionally, Tm value of the TCR molecule linked by an artificial interchain disulfide bond of the present invention is high, indicating that the molecule can correctly fold at higher temperature, maintain proper activity, and thus possess high stability. Meanwhile, it can be seen from the binding curves for TCR molecules binding to their original ligands that the decrease in concentration of TCR did not affect the binding of the TCR molecules to their corresponding antigens, which also demonstrated from another aspect that the TCR comprising the interchain disulfide bond of the present invention was stable. In the specificity test, the TCR molecules of the present invention with introduced artificial interchain disulfide bonds only bind to their respective antigens and do not interact with several other unrelated antigens and thus exhibit good specificity. Therefore, the above experimental data demonstrate that a soluble and stable three-domain TCR protein of the present invention can be obtained by introducing an artificial interchain disulfide bond between position 46 of TRAV and position 61 of TRBC1*01 or TRBC2*01 exon 1.

Example 10 Four-Domain TCR Molecule with an Formed Artificial Interchain Disulfide Bond Between Position 46 of TRAV and Position 61 of TRBC1*01 or TRBC2*01 Exon 1

In this example, it was demonstrated that it is possible to obtain a soluble and stable four-domain TCR molecule after an artificial interchain disulfide bond was formed at position 46 of TRAV of the TCR molecule and position 61 of TRBC1*01 or TRBC2*01 exon 1.

The amino acid at position 46 of TRAV of 1G4 TCR molecule was mutated into cysteine and the amino acid at position 61 of TRBC1*01 or TRBC2*01 exon 1 was mutated into cysteine, thereby forming an artificial interchain disulfide bond. Used primers and steps for mutation can be found in the above Examples.

The PCR, refolding and performance tests of the TCRs were performed according to the methods described in Examples 1 to 4, except that in the refolding step of TCR in Example 2, the amount of inclusion body of TCR α chain and β chain was 15 mg and 10 mg, respectively.

Figure 53:
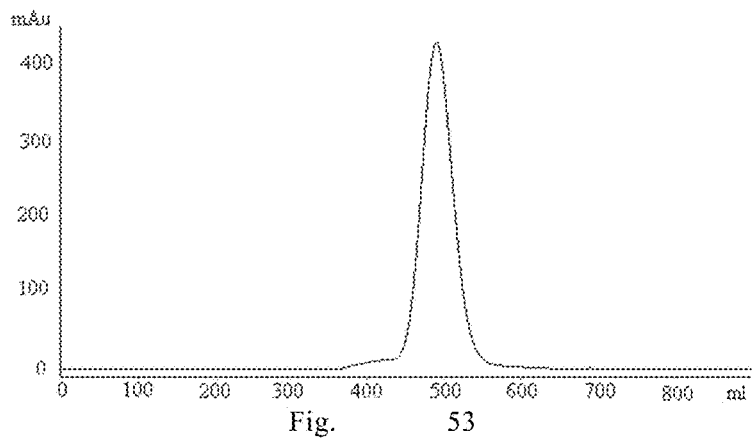
FIG. 53 shows an elution curve of gel filtration column of α chain and chain of four-domain TCR after refolding, wherein an artificial interchain disulfide bond is formed at position 46 of TRAV and position 61 of TRBC1*01 or TRBC2*01 exon 1.
Figure 54:
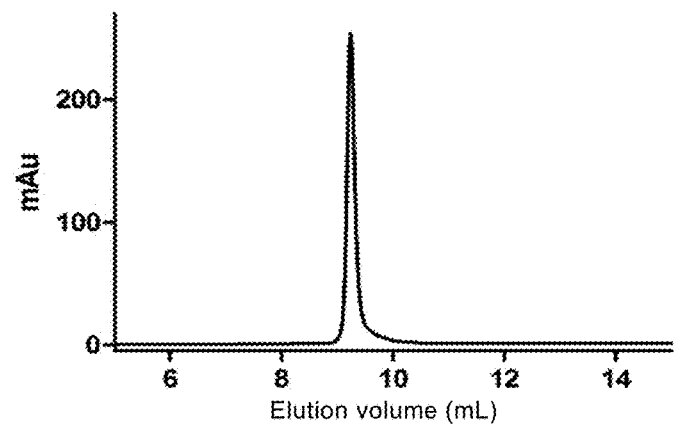
FIG. 54 shows a SEC spectrum of α chain and chain of four-domain TCR after refolding and protein purification, wherein an artificial interchain disulfide bond is formed at position 46 of TRAV and position 61 of TRBC1*01 or TRBC2*01 exon 1.
Figure 55:
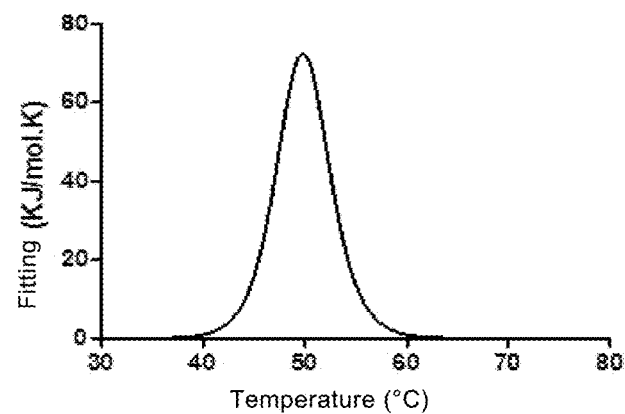
FIG. 55 shows a DSC thermogram of α chain and β chain of four-domain TCR after refolding and protein purification, wherein an artificial interchain disulfide bond is formed at position 46 of TRAV and position 61 of TRBC1*01 or TRBC2*01 exon 1.
Figure 56:
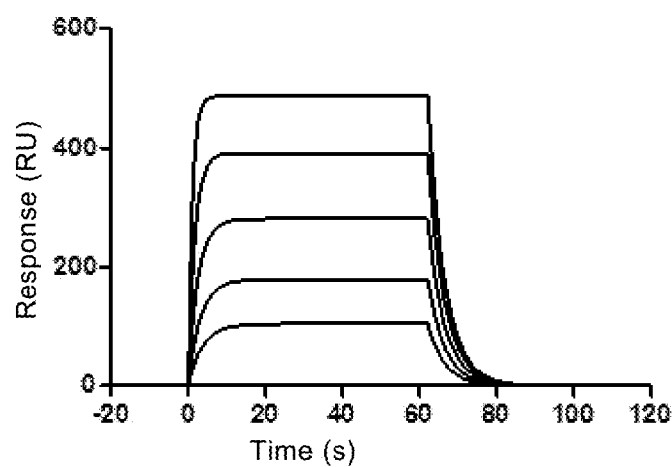
FIG. 56 shows binding curves of TCR molecule at different concentrations with its corresponding antigen, wherein the molecule is obtained from α chain and 13 chain of four-domain TCR after refolding and protein purification, and an artificial interchain disulfide bond is formed at position 46 of TRAV and position 61 of TRBC1*01 or TRBC2*01 exon 1.
Figure 67:
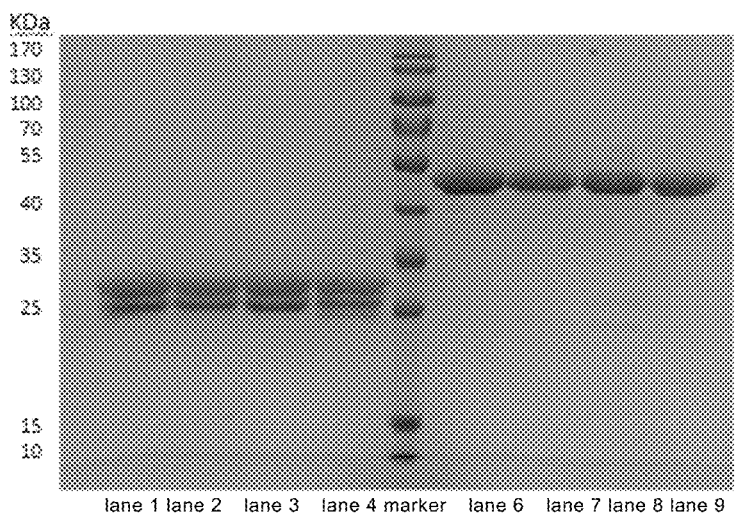
FIG. 67 shows gel electrophoresis of four-domain soluble protein containing an artificial interchain disulfide bond at different positions between α chain variable domain and chain constant domain of 1G4 TCR molecule.

The elution curve and the gel pattern of the four-domain TCR molecule of the present invention containing the artificial inter-chain disulfide bond were shown in lane 2 (reduced gel) and lane 7 (non-reducing gel) of FIGS. 53 and 67, respectively. The single and symmetrical HPLC elution peak was shown in FIG. 54. The refolding yield of protein reached 38%, the Tm value was 50° C. and the corresponding DSC spectrum is shown in FIG. 55. The binding curve of the TCR molecule to its corresponding antigen is shown in FIG. 56.

According to the above elution curves and the SDS gel electrophoresis, it was found that the eluted peak component was the soluble four-domain TCR molecule linked by an artificial interchain disulfide bond of the present invention, which formed a single band and was stable in SDS gel, and formed separate α chain and β chain after reduction. The refolding yield of protein is relatively high. Additionally, Tm value of the TCR molecule linked by an artificial interchain disulfide bond of the present invention is high, indicating that the molecule can correctly fold at higher temperature, maintain proper activity, and thus possess high stability. Meanwhile, it can be seen from the binding curves for TCR molecules binding to their original ligands that the decrease in concentration of TCR did not affect the binding of the TCR molecules to their corresponding antigens, which also demonstrated from another aspect that the TCR comprising the interchain disulfide bond of the present invention was stable. In the specificity test, the TCR molecules of the present invention with introduced artificial interchain disulfide bonds only bind to their respective antigens and do not interact with several other unrelated antigens and thus exhibit good specificity. Therefore, the above experimental data demonstrate that a soluble and stable four-domain TCR protein of the present invention can be obtained by introducing an artificial interchain disulfide bond between position 46 of TRAV and position 61 of TRBC1*01 or TRBC2*01 exon 1.

Example 11 Three-Domain TCR Molecule with an Formed Artificial Interchain Disulfide Bond Between Position 47 of TRAV and Position 60 of TRBC1*01 or TRBC2*01 Exon 1

In this example, it was demonstrated that it is possible to obtain a soluble and stable three-domain TCR molecule after an artificial interchain disulfide bond was formed at position 47 of TRAV of the TCR molecule and position 60 of TRBC1*01 or TRBC2*01 exon 1.

The amino acid at position 47 of TRAV of 1G4 TCR molecule was mutated into cysteine and the amino acid at position 60 of TRBC1*01 or TRBC2*01 exon 1 was mutated into cysteine, thereby forming an artificial interchain disulfide bond. Used primers and steps for mutation can be found in the above Examples.

The PCR, refolding and performance tests of the TCRs were performed according to the methods described in Examples 1 to 4.

Figure 57:
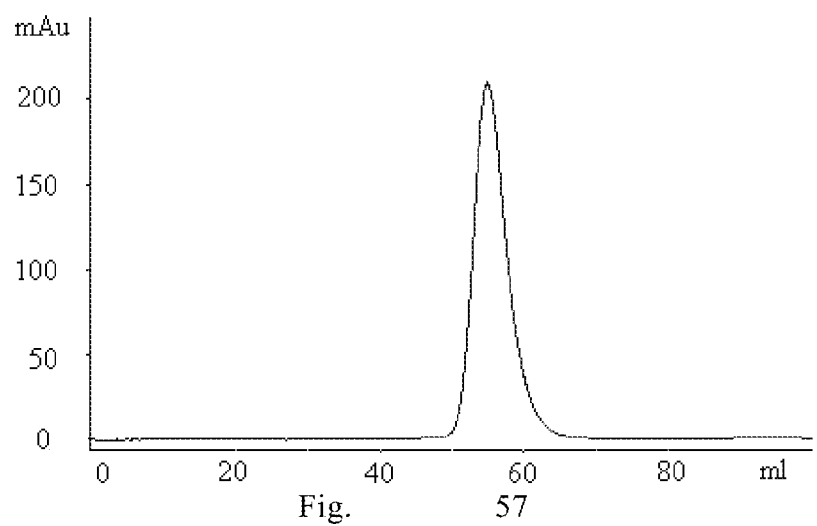
FIG. 57 shows an elution curve of gel filtration column of α chain and chain of three-domain TCR after refolding, wherein an artificial interchain disulfide bond is formed at position 47 of TRAV and position 60 of TRBC1*01 or TRBC2*01 exon 1.
Figure 58:
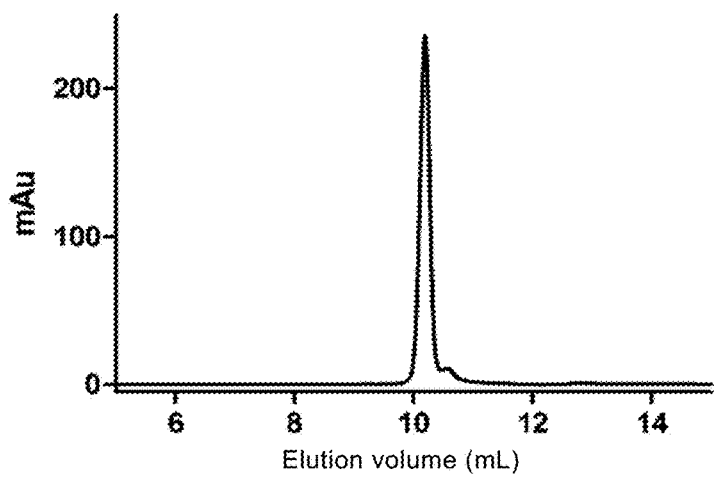
FIG. 58 shows a SEC spectrum of α chain and chain of three-domain TCR after refolding and protein purification, wherein an artificial interchain disulfide bond is formed at position 47 of TRAV and position 60 of TRBC1*01 or TRBC2*01 exon 1.
Figure 59:
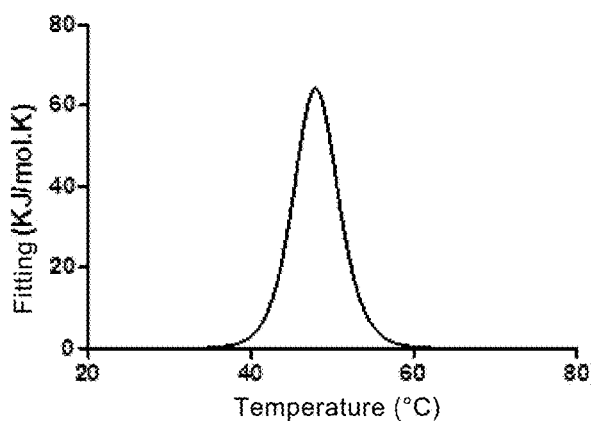
FIG. 59 shows a DSC thermogram of α chain and chain of three-domain TCR after refolding and protein purification, wherein an artificial interchain disulfide bond is formed at position 47 of TRAV and position 60 of TRBC1*01 or TRBC2*01 exon 1.
Figure 60:
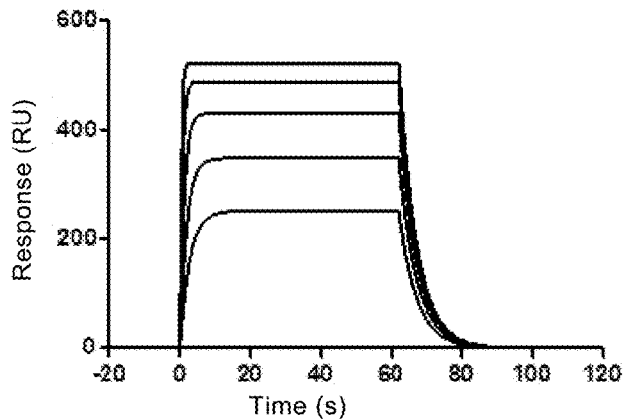
FIG. 60 shows binding curves of TCR molecule at different concentrations with its corresponding antigen, wherein the molecule is obtained from α chain and β chain of three-domain TCR after refolding and protein purification, and an artificial interchain disulfide bond is formed at position 47 of TRAV and position 60 of TRBC1*01 or TRBC2*01 exon 1.

The elution curve and the gel pattern of the three-domain TCR molecule of the present invention containing the artificial inter-chain disulfide bond were shown in lane 3 (reduced gel) and lane 8 (non-reducing gel) of FIGS. 57 and 65, respectively. The single and symmetrical HPLC elution peak was shown in FIG. 58. The refolding yield of protein reached 22%, the Tm value was 48° C. and the corresponding DSC spectrum is shown in FIG. 59. The binding curve of the TCR molecule to its corresponding antigen is shown in FIG. 60.

According to the above elution curves and the SDS gel electrophoresis, it was found that the eluted peak component was the soluble three-domain TCR molecule linked by an artificial interchain disulfide bond of the present invention, which formed a single band and was stable in SDS gel, and formed separate α chain variable domain and β chain after reduction. The refolding yield of protein is relatively high. Additionally, Tm value of the TCR molecule linked by an artificial interchain disulfide bond of the present invention is high, indicating that the molecule can correctly fold at higher temperature, maintain proper activity, and thus possess high stability. Meanwhile, it can be seen from the binding curves for TCR molecules binding to their original ligands that the decrease in concentration of TCR did not affect the binding of the TCR molecules to their corresponding antigens, which also demonstrated from another aspect that the TCR comprising the interchain disulfide bond of the present invention was stable. In the specificity test, the TCR molecules of the present invention with introduced artificial interchain disulfide bonds only bind to their respective antigens and do not interact with several other unrelated antigens and thus exhibit good specificity. Therefore, the above experimental data demonstrate that a soluble and stable three-domain TCR protein of the present invention can be obtained by introducing an artificial interchain disulfide bond between position 47 of TRAV and position 60 of TRBC1*01 or TRBC2*01 exon 1.

Example 12 Four-Domain TCR Molecule with an Formed Artificial Interchain Disulfide Bond Between Position 47 of TRAV and Position 60 of TRBC1*01 or TRBC2*01 Exon 1

In this example, it was demonstrated that it is possible to obtain a soluble and stable four-domain TCR molecule after an artificial interchain disulfide bond was formed at position 47 of TRAV of the TCR molecule and position 60 of TRBC1*01 or TRBC2*01 exon 1.

The amino acid at position 46 of TRAV of 1G4 TCR molecule was mutated into cysteine and the amino acid at position 61 of TRBC1*01 or TRBC2*01 exon 1 was mutated into cysteine, thereby forming an artificial interchain disulfide bond. Used primers and steps for mutation can be found in the above Examples.

The PCR, refolding and performance tests of the TCRs were performed according to the methods described in Examples 1 to 4, except that in the refolding step of TCR in Example 2, the amount of inclusion body of TCR α chain and β chain was 15 mg and 10 mg, respectively.

The elution curve and the gel pattern of the four-domain TCR molecule of the present invention containing the artificial inter-chain disulfide bond were shown in lane 3

Figure 61:
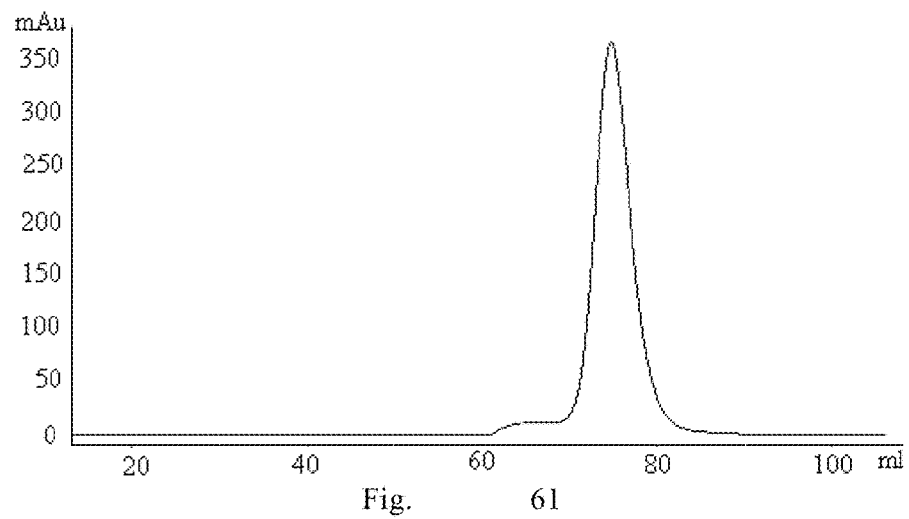
FIG. 61 shows an elution curve of gel filtration column of α chain and chain of four-domain TCR after refolding, wherein an artificial interchain disulfide bond is formed at position 47 of TRAV and position 60 of TRBC1*01 or TRBC2*01 exon 1.
Figure 62:
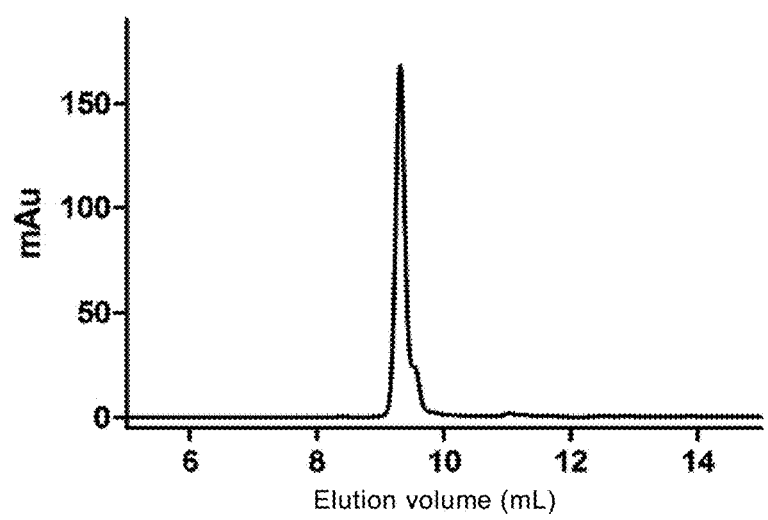
FIG. 62 shows a SEC spectrum of α chain and chain of four-domain TCR after refolding and protein purification, wherein an artificial interchain disulfide bond is formed at position 47 of TRAV and position 60 of TRBC1*01 or TRBC2*01 exon 1.
Figure 63:
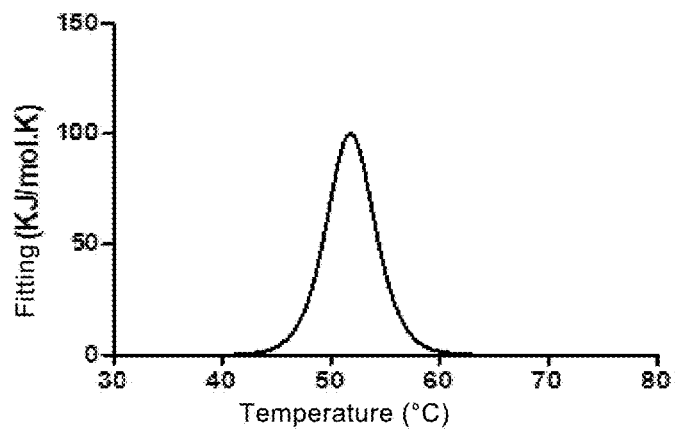
FIG. 63 shows a DSC thermogram of α chain and chain of four-domain TCR after refolding and protein purification, wherein an artificial interchain disulfide bond is formed at position 47 of TRAV and position 60 of TRBC1*01 or TRBC2*01 exon 1.
Figure 64:
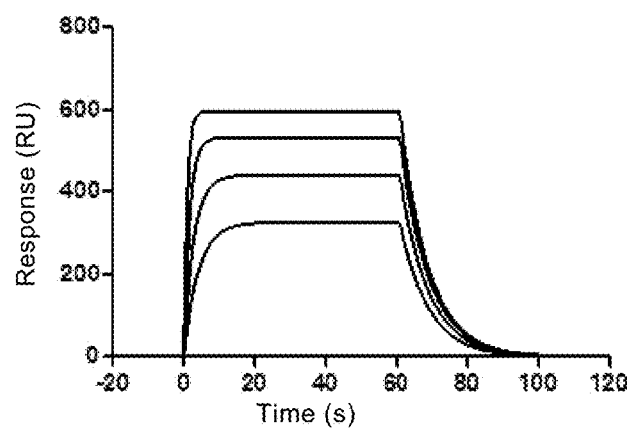
FIG. 64 shows binding curves of TCR molecule at different concentrations with its corresponding antigen, wherein the molecule is obtained from α chain and 13 chain of four-domain TCR after refolding and protein purification, and an artificial interchain disulfide bond is formed at position 47 of TRAV and position 60 of TRBC1*01 or TRBC2*01 exon 1.

(reduced gel) and lane 8 (non-reducing gel) of FIGS. 61 and 67, respectively. The single and symmetrical HPLC elution peak was shown in FIG. 62. The refolding yield of protein reached 31%, the Tm value was 52° C. and the corresponding DSC spectrum is shown in FIG. 63. The binding curve of the TCR molecule to its corresponding antigen is shown in FIG. 64.

According to the above elution curves and the SDS gel electrophoresis, it was found that the eluted peak component was the soluble four-domain TCR molecule linked by an artificial interchain disulfide bond of the present invention, which formed a single band and was stable in SDS gel, and formed separate α chain and β chain after reduction. The refolding yield of protein is relatively high. Additionally, Tm value of the TCR molecule linked by an artificial interchain disulfide bond of the present invention is high, indicating that the molecule can correctly fold at higher temperature, maintain proper activity, and thus possess high stability. Meanwhile, it can be seen from the binding curves for TCR molecules binding to their original ligands that the decrease in concentration of TCR did not affect the binding of the TCR molecules to their corresponding antigens, which also demonstrated from another aspect that the TCR comprising the interchain disulfide bond of the present invention was stable. In the specificity test, the TCR molecules of the present invention with introduced artificial interchain disulfide bonds only bind to their respective antigens and do not interact with several other unrelated antigens and thus exhibit good specificity. Therefore, the above experimental data demonstrate that a soluble and stable four-domain TCR protein of the present invention can be obtained by introducing an artificial interchain disulfide bond between position 47 of TRAV and position 60 of TRBC1*01 or TRBC2*01 exon 1.

All documents referred to in the present invention are incorporated by reference as if each reference is cited alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A αβ heterodimeric TCR, wherein an artificial interchain disulfide bond is contained between α chain variable region and β chain constant region of the TCR; and
cysteine residues that form the artificial interchain disulfide bond of the TCR substitute for:
an amino acid residue at position 46 of TRAV and an amino acid residue at position 60 of TRBC1*01 or TRBC2*01 exon 1;
an amino acid residue at position 47 of TRAV and an amino acid residue at position 61 of TRBC1*01 or TRBC2*01 exon 1;
an amino acid residue at position 46 of TRAV and an amino acid residue at position 61 of TRBC1*01 or TRBC2*01 exon 1; or
an amino acid residue at position 47 of TRAV and an amino acid residue at position 60 of TRBC1*01 or TRBC2*01 exon 1.

2. The TCR of claim 1, wherein the TCR is soluble.

3. The TCR of claim 1, wherein the TCR comprises α chain variable domain and β chain variable domain as well as all or part of β chain constant domains other than its transmembrane domain, however it does not comprise α chain constant domain, and α chain variable domain and β chain of the TCR form a heterodimer.

4. The TCR of claim 3, wherein the cysteine residue in β chain constant domain for forming a natural interchain disulfide bond is replaced with another amino acid.

5. The TCR of claim 4, wherein the cysteine residue in β chain constant domain for forming a natural interchain disulfide bond is replaced with alanine or serine.

6. The TCR of claim 3, wherein the β chain constant domain of the TCR is truncated at C-terminus, thereby removing cysteine residues for forming natural interchain disulfide bonds.

7. The TCR of claim 1, wherein the TCR comprises: (i) all or part of the TCR α chain other than its transmembrane domain, and (ii) all or part of the TCR β chain other than its transmembrane domain, wherein both of (i) and (ii) comprise variable domain and at least a portion of constant domains of TCR chain.

8. The TCR of claim 7, wherein there is no natural interchain disulfide bond between α and β chain constant domain of the TCR.

9. The TCR of claim 8, wherein the α chain and/or β chain constant region of the TCR are truncated at C-terminus, thereby removing cysteine residues for forming natural interchain disulfide bonds.

10. The TCR of claim 8, wherein the cysteine residue in α chain and/or β chain constant region of the TCR for forming a natural interchain disulfide bond is substituted with another residue.

11. The TCR of claim 7, wherein there is an artificial interchain disulfide bond between α chain constant region and β chain constant region of the TCR.

12. The TCR of claim 11, wherein cysteine residues that form the artificial interchain disulfide bond between α chain constant region and β chain constant region of the TCR substitute for:

48T of TRAC1*01 exon 1 and 57S of TRBC1*01 or TRBC2*01 exon 1;

45T of TRAC1*01 exon 1 and 77S of TRBC1*01 or TRBC2*01 exon 1;

10Y of TRAC1*01 exon 1 and 17S of TRBC1*01 or TRBC2*01 exon 1;

45T of TRAC1*01 exon 1 and 59D of TRBC1*01 or TRBC2*01 exon 1;

15S of TRAC1*01 exon 1 and 15E of TRBC1*01 or TRBC2*01 exon 1;

53R of TRAC1*01 exon 1 and 54S of TRBC1*01 or TRBC2*01 exon 1;

89P of TRAC1*01 exon 1 and 19A of TRBC1*01 or TRBC2*01 exon 1; or 10Y of TRAC1*01 exon 1 and 20E of TRBC1*01 or TRBC2*01 exon 1.

13. The TCR of claim 1, wherein a conjugate is bound with C- or N-terminus of the TCR α chain and/or β chain.

14. The TCR of claim 13, wherein the conjugate bound with the TCR is selected from a group consisting of: a detectable marker; a therapeutic agent; a PK modifying moiety and a combination thereof.

15. The TCR of claim 14, wherein the therapeutic agent bound with the TCR is anti-CD3 antibody which is linked at C- or N-terminus of α and/or β chains of the TCR.

16. A T-cell receptor complex, comprising one or more TCR molecules of claim 1.

17. A pharmaceutical composition, comprising a pharmaceutically acceptable carrier and a safe and effective dosage of the TCR of claim 1.

* * * * *

```
                        SEQUENCE LISTING

<160> NUMBER OF SEQ ID NOS: 45

<210> SEQ ID NO 1
<211> LENGTH: 115
<212> TYPE: PRT
<213> ORGANISM: Artificial sequence
<220> FEATURE:
<223> OTHER INFORMATION: Synthetic construct

<400> SEQUENCE: 1

Ala Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Cys Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
                100                 105                 110

His Pro Tyr
        115

<210> SEQ ID NO 2
<211> LENGTH: 241
<212> TYPE: PRT
<213> ORGANISM: Artificial sequence
<220> FEATURE:
<223> OTHER INFORMATION: Synthetic construct

<400> SEQUENCE: 2

Gly Val Thr Gln Thr Pro Lys Phe Gln Val Leu Lys Thr Gly Gln Ser
1               5                   10                  15

Met Thr Leu Gln Cys Ala Gln Asp Met Asn His Glu Tyr Met Ser Trp
                20                  25                  30
```

Tyr Arg Gln Asp Pro Gly Met Gly Leu Arg Leu Ile His Tyr Ser Val
            35                  40                  45

Gly Ala Gly Ile Thr Asp Gln Gly Glu Val Pro Asn Gly Tyr Asn Val
 50                  55                  60

Ser Arg Ser Thr Thr Glu Asp Phe Pro Leu Arg Leu Leu Ser Ala Ala
 65                  70                  75                  80

Pro Ser Gln Thr Ser Val Tyr Phe Cys Ala Ser Ser Tyr Val Gly Asn
                 85                  90                  95

Thr Gly Glu Leu Phe Phe Gly Glu Gly Ser Arg Leu Thr Val Leu Glu
            100                 105                 110

Asp Leu Lys Asn Val Phe Pro Pro Glu Val Ala Val Phe Glu Pro Ser
        115                 120                 125

Glu Ala Glu Ile Ser His Thr Gln Lys Ala Thr Leu Val Cys Leu Ala
130                 135                 140

Thr Gly Phe Tyr Pro Asp His Val Glu Leu Ser Trp Trp Val Asn Gly
145                 150                 155                 160

Lys Glu Val His Ser Gly Val Ser Thr Asp Cys Gln Pro Leu Lys Glu
                165                 170                 175

Gln Pro Ala Leu Asn Asp Ser Arg Tyr Ala Leu Ser Ser Arg Leu Arg
            180                 185                 190

Val Ser Ala Thr Phe Trp Gln Asn Pro Arg Asn His Phe Arg Cys Gln
        195                 200                 205

Val Gln Phe Tyr Gly Leu Ser Glu Asn Asp Glu Trp Thr Gln Asp Arg
    210                 215                 220

Ala Lys Pro Val Thr Gln Ile Val Ser Ala Glu Ala Trp Gly Arg Ala
225                 230                 235                 240

Asp

<210> SEQ ID NO 3
<211> LENGTH: 348
<212> TYPE: DNA
<213> ORGANISM: Artificial sequence
<220> FEATURE:
<223> OTHER INFORMATION: Synthetic construct

<400> SEQUENCE: 3
gcacaagaag ttactcaaat tccggcggcg ctgagcgttc cggaaggtga aaacctggtg      60
ctgaactgca gctttaccga tagcgcgatc tataacctgc agtggtttcg tcaagattgc     120
ggtaaaggtc tgaccagcct gctgctgatt cagagcagcc agcgtgaaca gaccagcggt     180
cgtctgaatg cgagcctgga taaaagcagc ggtcgtagca ccctgtatat tgcggcgagc     240
cagccgggtg atagcgcaac ctatctgtgt gcggttcgtc cgaccagcgg tggtagctat     300
attccgacct tggtcgtggg caccagcctg attgtgcatc cgtattaa                 348

<210> SEQ ID NO 4
<211> LENGTH: 726
<212> TYPE: DNA
<213> ORGANISM: Artificial sequence
<220> FEATURE:
<223> OTHER INFORMATION: Synthetic construct

<400> SEQUENCE: 4
ggcgtcacac aaaccccgaa atttcaggtg ctgaaaacgg gtcagagcat gaccctgcag      60
tgtgcgcagg atatgaacca cgaatacatg agctggtatc gtcaagatcc gggtatgggt     120
ctgcgtctga tccattatag cgtgggtgcg ggcattaccg atcagggtga agtgccgaac     180

-continued

```
ggttataatg ttagccgtag caccaccgaa gattttccgc tgcgtctgct gagcgcggcg      240
ccgagccaga ccagcgttta ttttttgcgcg agcagctatg ttggtaacac cggcgaactg     300 tttttggtg aaggcagccg tctgaccgtt ctggaagatc tgaaaaacgt gtttccgccg       360
gaagttgcgg tttttgaacc gagcgaagcg gaaattagcc ataccagaa agcgaccctg       420 gtttgtctgg cgaccggttt ttatccggat catgtggaac tgtcttggtg ggtgaacggc     480
aaagaagtgc atagcggtgt ttctaccgat tgccagccgc tgaaagaaca gccggcgctg     540
aatgatagcc gttatgcgct gtctagccgt ctgcgtgtta gcgcgacctt ttggcaaaat    600
ccgcgtaacc attttcgttg ccaggtgcag ttttatggcc tgagcgaaaa cgatgaatgg    660
acccaggatc gtgcgaagcc ggttacccag attgttagcg cggaagcctg gggccgcgca    720
gattaa                                                                726
```

```
<210> SEQ ID NO 5
<211> LENGTH: 111
<212> TYPE: PRT
<213> ORGANISM: Artificial sequence
<220> FEATURE:
<223> OTHER INFORMATION: Synthetic construct

<400> SEQUENCE: 5

Gly Gln Leu Leu Glu Gln Ser Pro Gln Phe Leu Ser Ile Gln Glu Gly
1               5                   10                  15

Glu Asn Leu Thr Val Tyr Cys Asn Ser Ser Val Phe Ser Ser Leu
            20                  25                  30

Gln Trp Tyr Arg Gln Glu Cys Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Ala Gly Ser Gln Gly
                85                  90                  95

Asn Leu Ile Phe Gly Lys Gly Thr Lys Leu Ser Val Lys Pro Asn
            100                 105                 110
```

```
<210> SEQ ID NO 6
<211> LENGTH: 243
<212> TYPE: PRT
<213> ORGANISM: Artificial sequence
<220> FEATURE:
<223> OTHER INFORMATION: Synthetic construct

<400> SEQUENCE: 6

Val Asp Gly Gly Ile Thr Gln Ser Pro Lys Tyr Leu Phe Arg Lys Glu
1               5                   10                  15

Gly Gln Asn Val Thr Leu Ser Cys Glu Gln Asn Leu Asn His Asp Ala
            20                  25                  30

Met Tyr Trp Tyr Arg Gln Asp Pro Gly Gln Gly Leu Arg Leu Ile Tyr
        35                  40                  45

Tyr Ser Gln Ile Val Asn Asp Phe Gln Lys Gly Asp Ile Ala Glu Gly
    50                  55                  60

Tyr Ser Val Ser Arg Glu Lys Lys Glu Ser Phe Pro Leu Thr Val Thr
65                  70                  75                  80

Ser Ala Gln Lys Asn Pro Thr Ala Phe Tyr Leu Cys Ala Ser Ser Ser
                85                  90                  95
```

Arg Ser Ser Tyr Glu Gln Tyr Phe Gly Pro Gly Thr Arg Leu Thr Val
            100                 105                 110

Thr Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Cys Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp

<210> SEQ ID NO 7
<211> LENGTH: 333
<212> TYPE: DNA
<213> ORGANISM: Artificial sequence
<220> FEATURE:
<223> OTHER INFORMATION: Synthetic construct

<400> SEQUENCE: 7
ggccaactgc tggaacaatc cccgcaattc ctgagtattc aagaaggcga aaatctgacg    60
gtctactgta attcatcatc ggtctttagc tctctgcagt ggtatcgtca agaatgcggt   120
gaaggtccgg tcctgctggt gaccgtggtt acgggcggtg aagtgaaaaa gctgaaacgt   180
ctgacctttc agttcggcga tgcgcgcaag gacagttccc tgcatattac cgcagcacag   240
ccgggtgata cgggtctgta cctgtgcgca ggcgctggta gccaaggtaa cctgattttt   300
ggcaagggta cgaagctgag cgttaaaccg aac                                333

<210> SEQ ID NO 8
<211> LENGTH: 729
<212> TYPE: DNA
<213> ORGANISM: Artificial sequence
<220> FEATURE:
<223> OTHER INFORMATION: Synthetic construct

<400> SEQUENCE: 8
gtggacggcg gcattaccca aagcccgaag tacctgtttc gcaaggaagg ccaaaatgtg    60
accctgtcgt gtgaacaaaa tctgaaccat gatgcgatgt attggtaccg tcaggacccg   120
ggtcaaggtc tgcgtctgat ttattacagc cagatcgtga atgattttca aaaaggcgac   180
attgcagaag gttatagcgt gagccgtgaa aagaaagaat cttttccgct gaccgtcacg   240
tccgctcaga gaaccccgac cgcgttctac ctgtgcgcga gcagcagccg tagcagctat   300
gaacaatact ttggtccggg tacgcgtctg accgtcacgg aagatctgaa aaacgtgttt   360
ccgccggaag ttgcggtttt tgaaccgagc gaagcggaaa ttagccatac ccagaaagcg   420
accctggttt gtctggcgac cggttttat ccggatcatg tggaactgtc ttggtgggtg   480
aacggcaaag aagtgcatag cggtgttct accgattgcc agccgctgaa agaacagccg   540

```
gcgctgaatg atagccgtta tgcgctgtct agccgtctgc gtgttagcgc gacctttggg    600
caaaatccgc gtaaccattt tcgttgccag gtgcagtttt atggcctgag cgaaaacgat    660
gaatggaccc aggatcgtgc gaagccggtt acccagattg ttagcgcgga agcctggggc    720
cgcgcagat                                                            729
```

<210> SEQ ID NO 9
<211> LENGTH: 113
<212> TYPE: PRT
<213> ORGANISM: Artificial sequence
<220> FEATURE:
<223> OTHER INFORMATION: Synthetic construct

<400> SEQUENCE: 9

```
Gly Lys Thr Thr Gln Pro Asn Ser Met Glu Ser Asn Glu Glu Glu Pro
1               5                   10                  15

Val His Leu Pro Cys Asn His Ser Thr Ile Ser Gly Thr Asp Tyr Ile
            20                  25                  30

His Trp Tyr Arg Gln Leu Cys Ser Gln Gly Pro Glu Tyr Val Ile His
        35                  40                  45

Gly Leu Thr Ser Asn Val Asn Asn Arg Met Ala Ser Leu Ala Ile Ala
    50                  55                  60

Glu Asp Arg Lys Ser Ser Thr Leu Ile Leu His Arg Ala Thr Leu Arg
65                  70                  75                  80

Asp Ala Ala Val Tyr Tyr Cys Ile Leu Pro Leu Ala Gly Gly Thr Ser
                85                  90                  95

Tyr Gly Lys Leu Thr Phe Gly Gln Gly Thr Ile Leu Thr Val His Pro
            100                 105                 110

Asn
```

<210> SEQ ID NO 10
<211> LENGTH: 241
<212> TYPE: PRT
<213> ORGANISM: Artificial sequence
<220> FEATURE:
<223> OTHER INFORMATION: Synthetic construct

<400> SEQUENCE: 10

```
Gly Val Ser Gln Ser Pro Arg Tyr Lys Val Ala Lys Arg Gly Gln Asp
1               5                   10                  15

Val Ala Leu Arg Cys Asp Pro Ile Ser Gly His Val Ser Leu Phe Trp
            20                  25                  30

Tyr Gln Gln Ala Leu Gly Gln Gly Pro Glu Phe Leu Thr Tyr Phe Gln
        35                  40                  45

Asn Glu Ala Gln Leu Asp Lys Ser Gly Leu Pro Ser Asp Arg Phe Phe
    50                  55                  60

Ala Glu Arg Pro Glu Gly Ser Val Ser Thr Leu Lys Ile Gln Arg Thr
65                  70                  75                  80

Gln Gln Glu Asp Ser Ala Val Tyr Leu Cys Ala Ser Ser Leu Gly Gln
                85                  90                  95

Ala Tyr Glu Gln Tyr Phe Gly Pro Gly Thr Arg Leu Thr Val Thr Glu
            100                 105                 110

Asp Leu Lys Asn Val Phe Pro Pro Glu Val Ala Val Phe Glu Pro Ser
        115                 120                 125

Glu Ala Glu Ile Ser His Thr Gln Lys Ala Thr Leu Val Cys Leu Ala
    130                 135                 140

Thr Gly Phe Tyr Pro Asp His Val Glu Leu Ser Trp Trp Val Asn Gly
```

```
                145                 150                 155                 160
Lys Glu Val His Ser Gly Val Ser Thr Asp Cys Gln Pro Leu Lys Glu
                    165                 170                 175

Gln Pro Ala Leu Asn Asp Ser Arg Tyr Ala Leu Ser Ser Arg Leu Arg
                180                 185                 190

Val Ser Ala Thr Phe Trp Gln Asn Pro Arg Asn His Phe Arg Cys Gln
                    195                 200                 205

Val Gln Phe Tyr Gly Leu Ser Glu Asn Asp Glu Trp Thr Gln Asp Arg
                210                 215                 220

Ala Lys Pro Val Thr Gln Ile Val Ser Ala Glu Ala Trp Gly Arg Ala
225                 230                 235                 240

Asp

<210> SEQ ID NO 11
<211> LENGTH: 339
<212> TYPE: DNA
<213> ORGANISM: Artificial sequence
<220> FEATURE:
<223> OTHER INFORMATION: Synthetic construct

<400> SEQUENCE: 11
ggcaaaacca cccagccgaa ctcaatggaa agcaacgaag aagaaccggt ccacctgccg      60
tgtaatcaca gcaccatctc aggcaccgat tatattcatt ggtaccgtca gctgtgcagc     120
caaggtccgg aatatgtgat ccacggtctg accagtaacg ttaacaatcg tatggcatcc     180
ctggcaattg ctgaagatcg caaaagctct accctgatcc tgcatcgtgc aacgctgcgt     240
gacgcagccg tttattactg cattctgccg ctggccggcg gtaccagcta cggcaagctg     300
acgtttggcc agggtaccat tctgacggtc caccgaac                              339

<210> SEQ ID NO 12
<211> LENGTH: 723
<212> TYPE: DNA
<213> ORGANISM: Artificial sequence
<220> FEATURE:
<223> OTHER INFORMATION: Synthetic construct

<400> SEQUENCE: 12
ggcgtgtccc aaagcccgcg ttacaaagtt gccaagcgtg gtcaagatgt tgctctgcgt      60
tgcgatccga ttagtggtca tgttagcctg ttttggtatc agcaagcgct gggccagggt     120
ccggaatttc tgacctactt ccagaacgaa gcacaactgg ataaatcagg cctgccgtcg     180
gaccgtttct ttgctgaacg cccggaaggt agtgtttcca ccctgaagat tcagcgtacg     240
cagcaagaag attctgcggt ctatctgtgc gccagctctc tgggccaggc gtatgaacaa     300
tactttggtc cgggtacgcg tctgaccgtc acgaagatc tgaaaaacgt gtttccgccg      360
gaagttgcgg ttttgaacc gagcgaagcg gaaattagcc atacccagaa agcgaccctg     420
gtttgtctgg cgaccggttt ttatccggat catgtggaac tgtcttggtg ggtgaacggc     480
aaagaagtgc atagcggtgt ttctaccgat tgccagccgc tgaaagaaca gccggcgctg     540
aatgatagcc gttatgcgct gtctagccgt ctgcgtgtta gcgcgacctt ttggcaaaat     600
ccgcgtaacc atttcgttg ccaggtgcag ttttatggcc tgagcgaaaa cgatgaatgg      660
acccaggatc gtgcgaagcc ggttacccag attgttagcg cggaagcctg ggccgcgca     720 gat                                                                    723

<210> SEQ ID NO 13
```

<211> LENGTH: 208
<212> TYPE: PRT
<213> ORGANISM: Artificial sequence
<220> FEATURE:
<223> OTHER INFORMATION: Synthetic construct

<400> SEQUENCE: 13

Ala Gln Glu Val Thr Gln Ile Pro Ala Ala Leu Ser Val Pro Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Cys Gly Lys Gly Leu Thr Ser Leu Leu
        35                  40                  45

Leu Ile Gln Ser Ser Gln Arg Glu Gln Thr Ser Gly Arg Leu Asn Ala
50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
130                 135                 140

Gln Thr Asn Val Ser Gln Ser Lys Asp Ser Asp Val Tyr Ile Thr Asp
145                 150                 155                 160

Lys Thr Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

<210> SEQ ID NO 14
<211> LENGTH: 624
<212> TYPE: DNA
<213> ORGANISM: Artificial sequence
<220> FEATURE:
<223> OTHER INFORMATION: Synthetic construct

<400> SEQUENCE: 14
gcacaagaag ttactcaaat tccggcggcg ctgagcgttc cggaaggtga aaacctggtg      60
ctgaactgca gctttaccga tagcgcgatc tataacctgc agtggtttcg tcaagattgc     120
ggtaaaggtc tgaccagcct gctgctgatt cagagcagcc agcgtgaaca gaccagcggt     180
cgtctgaatg cgagcctgga taaaagcagc ggtcgtagca ccctgtatat tgcggcgagc     240
cagccgggtg atagcgcaac ctatctgtgt gcggttcgtc cgaccagcgg tggtagctat     300
attccgacct ttggtcgtgg caccagcctg attgtgcatc cgtatatcca gaatccggat     360
ccggccgttt atcagctgcg tgatagcaaa agcagcgata aaagcgtgtg cctgttcacc     420
gattttgata gccagaccaa cgtgagccag agcaaagata gcgatgtgta catcaccgat     480
aaaaccgtgc tggatatgcg cagcatggat ttcaaaagca atagcgcggt tgcgtggagc     540
aacaaaagcg attttgcgtg cgcgaacgcg tttaacaaca gcatcatccc ggaagatacg     600
ttcttcccca gcccagaaag ttcc                                            624

<210> SEQ ID NO 15
<211> LENGTH: 204
<212> TYPE: PRT
<213> ORGANISM: Artificial sequence
<220> FEATURE:
<223> OTHER INFORMATION: Synthetic construct

<400> SEQUENCE: 15

Gly Gln Leu Leu Glu Gln Ser Pro Gln Phe Leu Ser Ile Gln Glu Gly
1               5                   10                  15

Glu Asn Leu Thr Val Tyr Cys Asn Ser Ser Val Phe Ser Ser Leu
            20                  25                  30

Gln Trp Tyr Arg Gln Glu Cys Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Ala Gly Ser Gln Gly
                85                  90                  95

Asn Leu Ile Phe Gly Lys Gly Thr Lys Leu Ser Val Lys Pro Asn Ile
            100                 105                 110

Gln Asn Pro Asp Pro Ala Val Tyr Gln Leu Arg Asp Ser Lys Ser Ser
        115                 120                 125

Asp Lys Ser Val Cys Leu Phe Thr Asp Phe Asp Ser Gln Thr Asn Val
    130                 135                 140

Ser Gln Ser Lys Asp Ser Asp Val Tyr Ile Thr Asp Lys Thr Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser
        195                 200

<210> SEQ ID NO 16
<211> LENGTH: 612
<212> TYPE: DNA
<213> ORGANISM: Artificial sequence
<220> FEATURE:
<223> OTHER INFORMATION: Synthetic construct

<400> SEQUENCE: 16
ggccaactgc tggaacaatc cccgcaattc ctgagtattc aagaaggcga aaatctgacg      60
gtctactgta attcatcatc ggtctttagc tctctgcagt ggtatcgtca agaatgcggt     120
gaaggtccgg tcctgctggt gaccgtggtt acgggcggtg aagtgaaaaa gctgaaacgt     180
ctgacctttc agttcggcga tgcgcgcaag gacagttccc tgcatattac cgcagcacag     240
ccgggtgata cgggtctgta cctgtgcgca ggcgctggta gccaaggtaa cctgattttt     300
ggcaagggta cgaagctgag cgttaaaccg aacatccaga tcccggatcc ggccgtttat     360
cagctgcgtg atagcaaaag cagcgataaa agcgtgtgcc tgttcaccga ttttgatagc     420
cagaccaacg tgagccagag caaagatagc gatgtgtaca tcaccgataa aaccgtgctg     480
gatatgcgca gcatggattt caaaagcaat agcgcggttg cgtggagcaa caaaagcgat     540
tttgcgtgcg cgaacgcgtt taacaacagc atcatcccgg aagatacgtt cttccccagc     600
ccagaaagtt cc                                                                612

<210> SEQ ID NO 17
<211> LENGTH: 206
<212> TYPE: PRT
<213> ORGANISM: Artificial sequence
<220> FEATURE:
<223> OTHER INFORMATION: Synthetic construct

<400> SEQUENCE: 17

Gly Lys Thr Thr Gln Pro Asn Ser Met Glu Ser Asn Glu Glu Pro
1               5                   10                  15

Val His Leu Pro Cys Asn His Ser Thr Ile Ser Gly Thr Asp Tyr Ile
            20                  25                  30

His Trp Tyr Arg Gln Leu Cys Ser Gln Gly Pro Glu Tyr Val Ile His
        35                  40                  45

Gly Leu Thr Ser Asn Val Asn Asn Arg Met Ala Ser Leu Ala Ile Ala
    50                  55                  60

Glu Asp Arg Lys Ser Ser Thr Leu Ile Leu His Arg Ala Thr Leu Arg
65                  70                  75                  80

Asp Ala Ala Val Tyr Tyr Cys Ile Leu Pro Leu Ala Gly Gly Thr Ser
                85                  90                  95

Tyr Gly Lys Leu Thr Phe Gly Gln Gly Thr Ile Leu Thr Val His Pro
            100                 105                 110

Asn Ile Gln Asn Pro Asp Pro Ala Val Tyr Gln Leu Arg Asp Ser Lys
        115                 120                 125

Ser Ser Asp Lys Ser Val Cys Leu Phe Thr Asp Phe Asp Ser Gln Thr
    130                 135                 140

Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
        195                 200                 205

<210> SEQ ID NO 18
<211> LENGTH: 618
<212> TYPE: DNA
<213> ORGANISM: Artificial sequence
<220> FEATURE:
<223> OTHER INFORMATION: Synthetic construct

<400> SEQUENCE: 18
ggcaaaacca cccagccgaa ctcaatggaa agcaacgaag aagaaccggt ccacctgccg      60
tgtaatcaca gcaccatctc aggcaccgat tatattcatt ggtaccgtca gctgtgcagc     120
caaggtccgg aatatgtgat ccacggtctg accagtaacg ttaacaatcg tatggcatcc     180
ctggcaattg ctgaagatcg caaaagctct accctgatcc tgcatcgtgc aacgctgcgt     240
gacgcagccg tttattactg cattctgccg ctggccggcg gtaccagcta cggcaagctg     300
acgtttggcc aggtaccat tctgacggtc acccgaaca tccagaatcc ggatccggcc      360
gtttatcagc tgcgtgatag caaaagcagc gataaaagcg tgtgcctgtt caccgatttt     420
gatagccaga ccaacgtgag ccagagcaaa gatagcgatg tgtacatcac cgataaaacc     480
gtgctggata tgcgcagcat ggatttcaaa agcaatagcg cggttgcgtg gagcaacaaa     540

-continued

```
agcgattttg cgtgcgcgaa cgcgtttaac aacagcatca tcccggaaga tacgttcttc    600
cccagcccag aaagttcc                                                  618
```

<210> SEQ ID NO 19
<211> LENGTH: 115
<212> TYPE: PRT
<213> ORGANISM: Artificial sequence
<220> FEATURE:
<223> OTHER INFORMATION: Synthetic construct

<400> SEQUENCE: 19

```
Ala Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Cys Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr
        115
```

<210> SEQ ID NO 20
<211> LENGTH: 241
<212> TYPE: PRT
<213> ORGANISM: Artificial sequence
<220> FEATURE:
<223> OTHER INFORMATION: Synthetic construct

<400> SEQUENCE: 20

```
Gly Val Thr Gln Thr Pro Lys Phe Gln Val Leu Lys Thr Gly Gln Ser
1               5                   10                  15

Met Thr Leu Gln Cys Ala Gln Asp Met Asn His Glu Tyr Met Ser Trp
            20                  25                  30

Tyr Arg Gln Asp Pro Gly Met Gly Leu Arg Leu Ile His Tyr Ser Val
        35                  40                  45

Gly Ala Gly Ile Thr Asp Gln Gly Glu Val Pro Asn Gly Tyr Asn Val
    50                  55                  60

Ser Arg Ser Thr Thr Glu Asp Phe Pro Leu Arg Leu Ser Ala Ala
65                  70                  75                  80

Pro Ser Gln Thr Ser Val Tyr Phe Cys Ala Ser Ser Tyr Val Gly Asn
                85                  90                  95

Thr Gly Glu Leu Phe Phe Gly Glu Gly Ser Arg Leu Thr Val Leu Glu
            100                 105                 110

Asp Leu Lys Asn Val Phe Pro Pro Glu Val Ala Val Phe Glu Pro Ser
        115                 120                 125

Glu Ala Glu Ile Ser His Thr Gln Lys Ala Thr Leu Val Cys Leu Ala
    130                 135                 140

Thr Gly Phe Tyr Pro Asp His Val Glu Leu Ser Trp Trp Val Asn Gly
145                 150                 155                 160

Lys Glu Val His Ser Gly Val Ser Thr Asp Pro Cys Pro Leu Lys Glu
```

```
                    165                 170                 175
Gln Pro Ala Leu Asn Asp Ser Arg Tyr Ala Leu Ser Ser Arg Leu Arg
            180                 185                 190

Val Ser Ala Thr Phe Trp Gln Asn Pro Arg Asn His Phe Arg Cys Gln
        195                 200                 205

Val Gln Phe Tyr Gly Leu Ser Glu Asn Asp Glu Trp Thr Gln Asp Arg
    210                 215                 220

Ala Lys Pro Val Thr Gln Ile Val Ser Ala Glu Ala Trp Gly Arg Ala
225                 230                 235                 240

Asp

<210> SEQ ID NO 21
<211> LENGTH: 345
<212> TYPE: DNA
<213> ORGANISM: Artificial sequence
<220> FEATURE:
<223> OTHER INFORMATION: Synthetic construct

<400> SEQUENCE: 21
gcacaagaag ttactcaaat tccggcggcg ctgagcgttc cggaaggtga aaacctggtg    60
ctgaactgca gctttaccga tagcgcgatc tataacctgc agtggtttcg tcaagatccg   120
tgcaaaggtc tgaccagcct gctgctgatt cagagcagcc agcgtgaaca gaccagcggt   180
cgtctgaatg cgagcctgga taaaagcagc ggtcgtagca ccctgtatat tgcggcgagc   240
cagccgggtg atagcgcaac ctatctgtgt gcggttcgtc cgaccagcgg tggtagctat   300
attccgacct tggtcgtgg caccagcctg attgtgcatc cgtat                    345

<210> SEQ ID NO 22
<211> LENGTH: 723
<212> TYPE: DNA
<213> ORGANISM: Artificial sequence
<220> FEATURE:
<223> OTHER INFORMATION: Synthetic construct

<400> SEQUENCE: 22
ggcgtcacac aaaccccgaa atttcaggtg ctgaaaacgg gtcagagcat gaccctgcag    60
tgtgcgcagg atatgaacca cgaatacatg agctggtatc gtcaagatcc gggtatgggt   120
ctgcgtctga tccattatag cgtgggtgcg ggcattaccg atcagggtga agtgccgaac   180
ggttataatg ttagccgtag caccaccgaa gattttccgc tgcgtctgct gagcgcggcg   240
ccgagccaga ccagcgttta ttttgcgcg agcagctatg ttggtaacac cggcgaactg   300
ttttttggtg aaggcagccg tctgaccgtt ctggaagatc tgaaaaacgt gtttccgccg   360
gaagttgcgg tttttgaacc gagcgaagcg gaaattagcc ataccagaa agcgaccctg   420 gtttgtctgg cgaccggttt ttatccggat catgtggaac tgtcttggtg ggtgaacggc   480
aaagaagtgc atagcggtgt ttctaccgat ccgtgcccgc tgaaagaaca gccggcgctg   540
aatgatagcc gttatgcgct gtctagccgt ctgcgtgtta gcgcgacctt ttggcaaaat   600
ccgcgtaacc attttcgttg ccaggtgcag ttttatggcc tgagcgaaaa cgatgaatgg   660
acccaggatc gtgcgaagcc ggttacccag attgttagcg cggaagcctg gggccgcgca   720
gat                                                                 723

<210> SEQ ID NO 23
<211> LENGTH: 208
<212> TYPE: PRT
<213> ORGANISM: Artificial sequence
```

<220> FEATURE:
<223> OTHER INFORMATION: Synthetic construct

<400> SEQUENCE: 23

```
Ala Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Cys Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Thr Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205
```

<210> SEQ ID NO 24
<211> LENGTH: 627
<212> TYPE: DNA
<213> ORGANISM: Artificial sequence
<220> FEATURE:
<223> OTHER INFORMATION: Synthetic construct

<400> SEQUENCE: 24

```
atggcacaag aagttactca aattccggcg gcgctgagcg ttccggaagg tgaaaacctg    60
gtgctgaact gcagctttac cgatagcgcg atctataacc tgcagtggtt tcgtcaagat   120
ccgtgcaaag gtctgaccag cctgctgctg attcagagca gccagcgtga acagaccagc   180
ggtcgtctga tgcgagcct ggataaaagc agcggtcgta gcaccctgta tattgcggcg   240
agccagccgg gtgatagcgc aacctatctg tgtgcggttc gtccgaccag cggtggtagc   300
tatattccga cctttggtcg tggcaccagc ctgattgtgc atccgtatat ccagaatccg   360
gatccggccg tttatcagct gcgtgatagc aaaagcagcg ataaaagcgt gtgcctgttc   420
accgattttg atagccagac caacgtgagc cagagcaaag atagcgatgt gtacatcacc   480
gataaaaccg tgctggatat gcgcagcatg gatttcaaaa gcaatagcgc ggttgcgtgg   540
agcaacaaaa gcgattttgc gtgcgcgaac gcgtttaaca acagcatcat cccggaagat   600
acgttcttcc ccagcccaga aagttcc                                      627
```

<210> SEQ ID NO 25
<211> LENGTH: 9

```
<212> TYPE: PRT
<213> ORGANISM: Homo sapiens

<400> SEQUENCE: 25

Ser Leu Leu Met Trp Ile Thr Gln Cys
1               5

<210> SEQ ID NO 26
<211> LENGTH: 34
<212> TYPE: DNA
<213> ORGANISM: Artificial sequence
<220> FEATURE:
<223> OTHER INFORMATION: Synthetic construct

<400> SEQUENCE: 26
gtggtttcgt caagattgcg gtaaaggtct gacc                                  34

<210> SEQ ID NO 27
<211> LENGTH: 34
<212> TYPE: DNA
<213> ORGANISM: Artificial sequence
<220> FEATURE:
<223> OTHER INFORMATION: Synthetic construct

<400> SEQUENCE: 27
ggtcagacct ttaccgcaat cttgacgaaa ccac                                  34

<210> SEQ ID NO 28
<211> LENGTH: 34
<212> TYPE: DNA
<213> ORGANISM: Artificial sequence
<220> FEATURE:
<223> OTHER INFORMATION: Synthetic construct

<400> SEQUENCE: 28
ggtgtttcta ccgattgcca gccgctgaaa gaac                                  34

<210> SEQ ID NO 29
<211> LENGTH: 34
<212> TYPE: DNA
<213> ORGANISM: Artificial sequence
<220> FEATURE:
<223> OTHER INFORMATION: Synthetic construct

<400> SEQUENCE: 29
gttctttcag cggctggcaa tcggtagaaa cacc                                  34

<210> SEQ ID NO 30
<211> LENGTH: 9
<212> TYPE: PRT
<213> ORGANISM: Homo sapiens

<400> SEQUENCE: 30

Gly Ile Leu Gly Phe Val Phe Thr Leu
1               5

<210> SEQ ID NO 31
<211> LENGTH: 9
<212> TYPE: PRT
<213> ORGANISM: Homo sapiens

<400> SEQUENCE: 31

Glu Glu Tyr Leu Lys Ala Trp Thr Phe
1               5
```

<210> SEQ ID NO 32
<211> LENGTH: 34
<212> TYPE: DNA
<213> ORGANISM: Artificial sequence
<220> FEATURE:
<223> OTHER INFORMATION: Synthetic construct

<400> SEQUENCE: 32
gtggtatcgt caagaatgcg gtgaaggtcc ggtc         34

<210> SEQ ID NO 33
<211> LENGTH: 34
<212> TYPE: DNA
<213> ORGANISM: Artificial sequence
<220> FEATURE:
<223> OTHER INFORMATION: Synthetic construct

<400> SEQUENCE: 33
gaccggacct tcaccgcatt cttgacgata ccac         34

<210> SEQ ID NO 34
<211> LENGTH: 34
<212> TYPE: DNA
<213> ORGANISM: Artificial sequence
<220> FEATURE:
<223> OTHER INFORMATION: Synthetic construct

<400> SEQUENCE: 34
ggtgtttcta ccgattgcca gccgctgaaa gaac         34

<210> SEQ ID NO 35
<211> LENGTH: 34
<212> TYPE: DNA
<213> ORGANISM: Artificial sequence
<220> FEATURE:
<223> OTHER INFORMATION: Synthetic construct

<400> SEQUENCE: 35
gttctttcag cggctggcaa tcggtagaaa cacc         34

<210> SEQ ID NO 36
<211> LENGTH: 34
<212> TYPE: DNA
<213> ORGANISM: Artificial sequence
<220> FEATURE:
<223> OTHER INFORMATION: Synthetic construct

<400> SEQUENCE: 36
cattggtacc gtcagctgtg cagccaaggt ccgg         34

<210> SEQ ID NO 37
<211> LENGTH: 34
<212> TYPE: DNA
<213> ORGANISM: Artificial sequence
<220> FEATURE:
<223> OTHER INFORMATION: Synthetic construct

<400> SEQUENCE: 37
ccggaccttg gctgcacagc tgacggtacc aatg         34

<210> SEQ ID NO 38
<211> LENGTH: 34
<212> TYPE: DNA
<213> ORGANISM: Artificial sequence
<220> FEATURE:
<223> OTHER INFORMATION: Synthetic construct

<400> SEQUENCE: 38
ggtgtttcta ccgattgcca gccgctgaaa gaac                                34

<210> SEQ ID NO 39
<211> LENGTH: 34
<212> TYPE: DNA
<213> ORGANISM: Artificial sequence
<220> FEATURE:
<223> OTHER INFORMATION: Synthetic construct

<400> SEQUENCE: 39
gttctttcag cggctggcaa tcggtagaaa cacc                                34

<210> SEQ ID NO 40
<211> LENGTH: 34
<212> TYPE: DNA
<213> ORGANISM: Artificial sequence
<220> FEATURE:
<223> OTHER INFORMATION: Synthetic construct

<400> SEQUENCE: 40
gtttcgtcaa gatccgtgca aaggtctgac cagc                                34

<210> SEQ ID NO 41
<211> LENGTH: 34
<212> TYPE: DNA
<213> ORGANISM: Artificial sequence
<220> FEATURE:
<223> OTHER INFORMATION: Synthetic construct

<400> SEQUENCE: 41
gctggtcaga cctttgcacg gatcttgacg aaac                                34

<210> SEQ ID NO 42
<211> LENGTH: 33
<212> TYPE: DNA
<213> ORGANISM: Artificial sequence
<220> FEATURE:
<223> OTHER INFORMATION: Synthetic construct

<400> SEQUENCE: 42
gtttctaccg atccgtgccc gctgaaagaa cag                                 33

<210> SEQ ID NO 43
<211> LENGTH: 33
<212> TYPE: DNA
<213> ORGANISM: Artificial sequence
<220> FEATURE:
<223> OTHER INFORMATION: Synthetic construct

<400> SEQUENCE: 43
ctgttctttc agcgggcacg gatcggtaga aac                                 33

<210> SEQ ID NO 44
<211> LENGTH: 129
<212> TYPE: PRT
<213> ORGANISM: Homo sapiens

<400> SEQUENCE: 44

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn

```
                35                  40                  45
Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
            115                 120                 125

Ala

<210> SEQ ID NO 45
<211> LENGTH: 129
<212> TYPE: PRT
<213> ORGANISM: Homo sapiens

<400> SEQUENCE: 45

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
            115                 120                 125

Ala
```